US005589174A

United States Patent [19]

Okuno et al.

[11] Patent Number: 5,589,174
[45] Date of Patent: Dec. 31, 1996

[54] ANTI-HUMAN INFLUENZA VIRUS ANTIBODY

[75] Inventors: Yoshinobu Okuno, Toyonaka; Yuji Isegawa, Takatsuki; Fuyoko Sasao, Ibaraki; Shigeharu Ueda, Nishinomiya, all of Japan

[73] Assignee: Takara Shuzo Co., Ltd., Kyoto-fu, Japan

[21] Appl. No.: 229,781

[22] Filed: Apr. 19, 1994

Related U.S. Application Data

[63] Continuation-in-part of Ser. No. 054,016, Apr. 29, 1993, abandoned.

[30] Foreign Application Priority Data

| | | | |
|---|---|---|---|
| Sep. 17, 1992 | [JP] | Japan | 4-272538 |
| Apr. 20, 1993 | [JP] | Japan | 5-115216 |
| Mar. 16, 1994 | [JP] | Japan | 6-070194 |

[51] Int. Cl.$^6$ .......... A61K 39/395; C07K 16/08; C12N 5/20; C12N 15/06

[52] U.S. Cl. .......... 424/147.1; 435/240.27; 530/387.9; 530/388.2; 530/388.3; 530/389.1; 530/389.4; 935/104; 935/103

[58] Field of Search .......... 530/388.1, 388.22, 530/388.3, 389.1, 389.4, 387.1, 390.1, 387.9, 388.2; 435/240.27; 424/147.1; 935/103, 104

[56] References Cited

FOREIGN PATENT DOCUMENTS 228737 8/1986 Germany .

OTHER PUBLICATIONS

WPI Abstract of Japanese Patent Publication No. 59–501714 dated Oct. 11, 1994.
Green et al., Cell, 28, 477–487 (1982) "Immunogenic Structure of the Influenza Virus Hemagglutinin".
Okuno et al., Report on 1st China –Japan International Congress of Virology, pp. 47–48, (May 26–28, 1992), "Characterization of A Monoclonal Antibody Which Cross–Neutralized H1 and H2 Subtypes of Influenza A Virus".
Okuno et al., J. Virology, 67, No. 5, pp. 2552–2558, (May 1993) "A Common Neutralizing Epitope Conserved between the Hemagglutinins of Influenza A Virus H1 and H2 Strains".
Harns et al., Tibtech, 11:42, 1993.
Osband et al., Immunol. Today, 11:93, 1990.

*Primary Examiner*—Frank C. Eisenschenk
*Attorney, Agent, or Firm*—Wenderoth, Lind & Ponack

[57] ABSTRACT

An anti-human influenza virus antibody is provided which recognizes the stem regions of haemagglutinin molecules of the H1N1 and H2N2 subtypes and has a neutralization activity, but does not recognize the stem region of the H3N2 subtype and has no neutralization activity. Also provided is an immunogenic artificial polypeptide having an antigenicity substantially the same as the stem regions of haemagglutinin molecules. Provided further is an immunogenic artificial polypeptide having an antigenicity substantially the same as the stem regions of haemagglutinin molecule and lacking the globular head region of haemagglutinin molecules. The antibody is useful in the diagnosis and treatment of influenza A virus, while the polypeptides are useful as a vaccine.

10 Claims, 6 Drawing Sheets

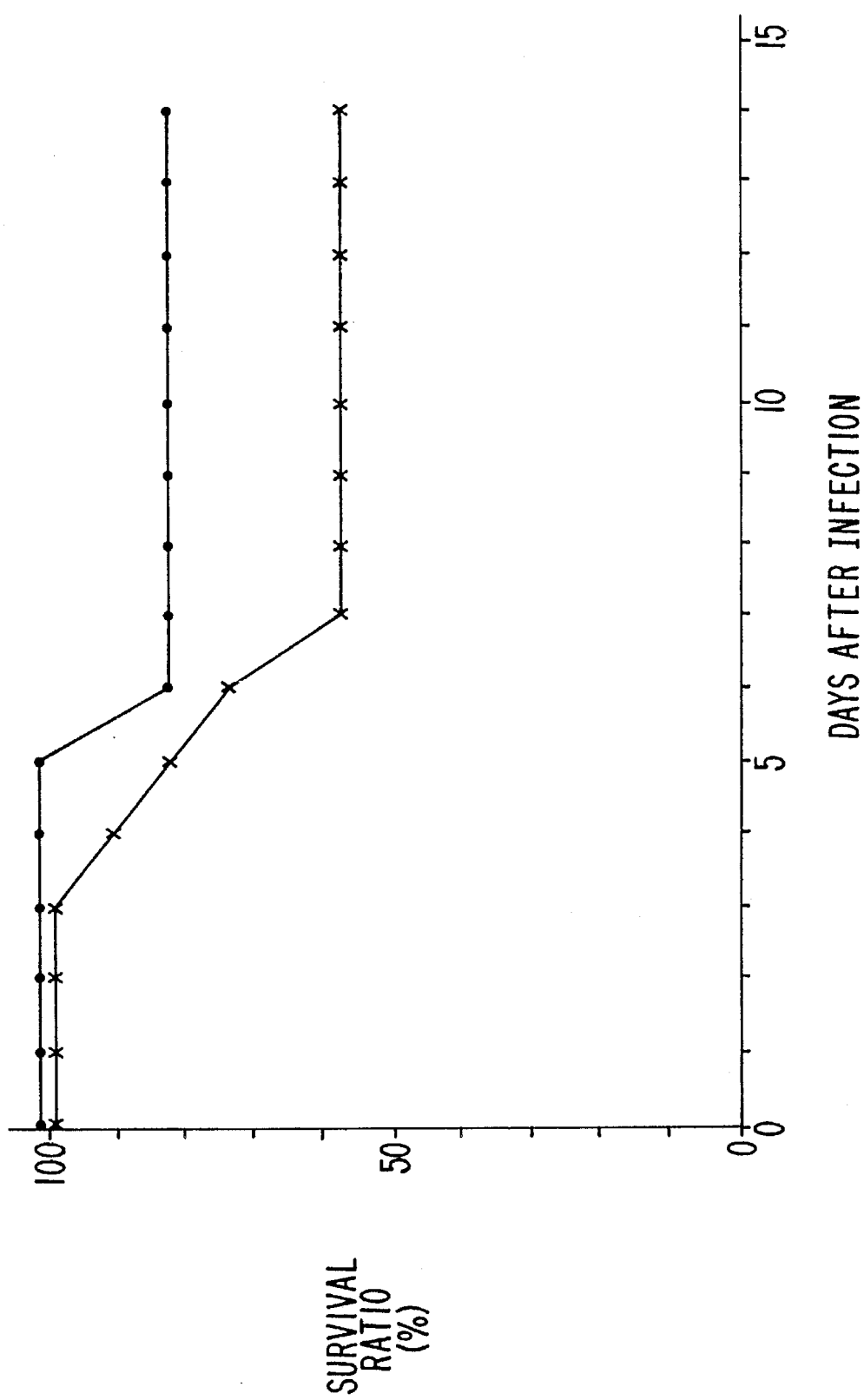

ANTI-HUMAN INFLUENZA VIRUS ANTIBODY

This application is a continuation-in-part of now abandoned application Ser. No. 08/054,016 filed Apr. 29, 1993.

BACKGROUND OF THE INVENTION

1. Field of the Invention

This invention relates to an antibody against hemagglutinin of human influenza A virus, a polypeptide containing an antigen site recognized by the antibody, and a gene coding for said polypeptide.

2. Description of Related Art

There are three types (A, S and C) of influenza viruses and the worldwide prevalence of influenza causing a large number of deaths is caused by human influenza A virus.

Influenza A virus is further classified into various subtypes depending on the antigenicities of hemagglutinin (hereinafter referred to simply as HA) and neuraminidase (hereinafter referred to simply as NA) which are vital surface proteins. There have been known so far three subtypes of human influenza A viruses, namely, the H1N1, H2N2 and H3N2 subtypes.

The HA of influenza A virus comprises two structurally distinct regions, namely, a globular head region and a stem region. The globular head region contains a receptor binding site which is responsible for virus attachment to a target cell and participates in the hemagglutination activity of HA. On the other hand, the stem region contains a fusion peptide which is necessary for membrane fusion between the viral envelope and an endosomal membrane of the cell and thus relates to fusion activity [Wiley et al., Ann. Rev. Biochem., 56, 365–394 (1987)].

All of anti-HA antibodies, which have been obtained hitherto as an antibody capable of recognizing the H1N1 and H2N2 subtypes, recognize the globular head region of HA. However, this region most frequently undergoes antigen mutation. Therefore, these antibodies are not common to the subtypes of human infleunza A virus and, further, lose the recognizing ability with antigenic changes in the HA of the virus.

On the other hand, Green et al. have synthesized a polypeptide based on an amino acid sequence in the stem region of HA of the H3N2 subtype and obtained antibodies against this polypeptide. However, these antibodies have a low neutralization activity (Published Japanese Translation of PCT Patent Applications from Other Countries, No. 501714/1984). Furthermore, the polypeptide per se employed as an antigen does not react with rabbit antiviral serum obtained by immunizing with the H3N2 subtype, which suggests that there is a problem from the viewpoint of antigenicity too [Cell, 28, 477–487 (1982)].

The infectivity of the HA of influenza A virus is activated when the HA is cleaved at one site with a protease. The larger polypeptide thus obtained is called HA1 while the smaller one HA2. It is believed that between these polypeptide HA2 will undergo less antigen mutation due to the subtype.

In East German Patent Laid-Open No. 228737, H. Glathe et. al. describe that HA2 is taken out by treating viral particles successively with an acid and trypsin or with a reducing agent alone.

By these treatments, however, HA molecules are destroyed in the stereostructure and irreversibly denatured. As a result, the HA2 thus obtained does not have its inherent stereostructure. In addition, the above-mentioned patent is silent whether the efficacy of the obtained HA2 as a vaccine has been specifically confirmed or not.

Human influenza A virus periodically changes types of HA and NA and thus causes wide prevalence. It is often observed that vaccinization before winter, i.e, the season of prevalence, produces no effect, since the prevalence is caused by a virus of a different type. If an antibody, which is common to virus subtypes in HA and NA molecules and capable of recognizing an antigen site hardly undergoing antigenic mutation, in particular, the configuration, and has neutralization activity for viruses, can be acquired, this antibody is usable in the diagnosis, prevention and treatment of infection with the A virus. Furthermore, the antigen site per se is useful as a vaccine.

SUMMARY OF THE INVENTION

It is an object of the present invention to provide an antibody which has a cross recognizing ability for influenza A virus subtypes and has a virus neutralization activity, an antigen site polypeptide which is usable as a vaccine, and a gene coding for said polypeptide.

To sum up, the first invention relates to an anti-human influenza virus antibody characterized by having the characteristics (a) and (b) specified below:

(a) recognizing the stem region of HA molecule of the H1N1 and H2N2 Subtypes of human influenza A virus but not recognizing the stem region of a HA molecule of the H3N2 subtype thereof; and (b) having neutralization activity for the H1N1 and H2N2 subtypes of human influenza A virus but no neutralization activity for the H3N2 subtype thereof.

The second invention relates to an immunogenic artificial polypeptide characterized by having an antigenicity substantially the same as that of the stem region in HA molecule of human influenza A virus.

The third invention relates to an immunogenic artificial polypeptide characterized by having an antigenicity substantially the same as that of the stem region in HA molecule of human influenza A virus and lacking a globular head region of HA molecule.

The fourth invention relates to a gene coding for the immunogenic artificial polypeptide of the second invention.

The fifth invention relates to a gene coding for the immunogenic artificial polypeptide of the third invention.

The present inventors have conducted extensive studies and consequently found out that an antibody against an antigen site, which is conserved commonly in the stem regions of HA molecule of H1N1 and H2N2 subtypes of human influenza A virus, has a potent neutralization activity for viruses of the H1N1 and H2N2 subtypes, that this antibody is highly useful in the treatment and prevention of influenza and that a polypeptide having an antigen site which is conserved commonly in the stem region of HA molecule of human influenza A virus is useful as a vaccine. And the present inventors have found out that a polypeptide having an antigen site, which is conserved commonly in the stem regions of HA molecule of human influenza A virus, and lacking the globular head region of HA molecule of human influenza A virus is highly useful as a vaccine. And then the present inventors have created a gene coding for said polypeptides which is useful for manufacture of said polypeptides by the genetic recombination technology. Thus the present invention was completed.

Examples of the immunogenic artificial polypeptide of the present invention, which has an antigenicity substantially the same as the stem region of HA molecule of the influenza A viruses and lacks a globular head region of HA molecules, includes polypeptide which lacks a globular head region of HA molecules by artificial proteolysis, and which is expressed by the HA gene lacking specifically a globular head region of HA molecules. These polypeptides should only have the configuration which the antibody recognizing an antigen site common to the stem regions of HA molecule specifically can recognize, may lack some part of the molecule or also may have the additional amino acid sequence.

Furthermore, these polypeptides may be partially digested with a protease in the process for producing the same by the protein engineering or genetic engineering technique.

Namely, the expression "having an antigenicity substantially the same as that of the stem region in HA molecule" as used herein means that the polypeptide has an antigenicity of both of the HA1 and HA2 in the stem region of HA molecule which is efficiently usable as a vaccine. Therefore such a polypeptide comprising HA2 alone, the inherent stereostructure of which has been destroyed due to denaturation, as the one reported by H. Glathe et. al. as cited above, is excluded from the scope of the present invention.

As examples of the immunogenic artificial polypeptide of the present invention which is the most effective as a vaccine, the following ones may be cited.

(1) An immunogenic artificial polypeptide which contains at least a TGLRN polypeptide sequence represented by the SEQ ID No. 1 in the sequence listing and a GITNKVNS-VIEK polypeptide sequence represented by the SEQ ID No. 2 in the sequence listing in the molecule and has an antigenicity wherein the configuration of these sequences is substantially the same as that of the stem region of hemagglutinin molecule of the H1N1 and H2N2 subtypes (2) An immunogenic artificial polypeptide which contains at least a TGMRN polypeptide sequence represented by the SEQ ID No. 3 in the sequence listing and a QINGKLNR (L/V) IEK polypeptide sequence represented by the SEQ ID No. 4 in the sequence listing in the molecule and has an antigenicity wherein the configuration of these sequences is substantially the same as that of the stem region of hemagglutinin molecule of the H3N2 subtype.

(3) An immunogenic artificial polypeptide of the third invention of the present invention separated from hemaglutinin molecule of human influenza A virus which has been treated with a protease.

The antibody according to the present invention, which recognizes a site common to the stem regions in HA molecules of the H1N1 and H2N2 subtypes of human influenza A virus and has a neutralization activity for the H1N1 and H2N2 subtypes of human influenza A virus, can be prepared as a monoclonal antibody in the following manner. A mammal such as mouse, guinea pig or rabbit is immunized with an antigen. As the antigen, viral particles selected from among those of the H1N1 and H2N2 subtypes may be used. Examples of virus strains of the H1N1 subtype include A/Bangkok/10/83, A/Yamagata/120/86, A/Osaka/930/88, A/Suita/1/89 (each being a stock of the Research Institute for Microbial Diseases, Osaka University), A/PR/8/34 [influenza (H1N1), ATCC VR-95], A1/FM/1/47 [influenza A (H1N1), ATCC VR-97], A/New Jersey/8/76 [influenza A (H1N1), ATCC VR-897], A/NWS/33 [influenza A (H1N1), ATCC VR-219], A/Weiss/43 [influenza A (H1N1), ATCC VR-96] and A/WS/33 [influenza A (H1N1), ATCC VR-825]. Examples of strains of the H2N2 subtype include A/Okuda/57, A/Adachi/2/57, A/Kumamoto/1/65, A/Kaizuka/2/65, A/Izumi/5/65 (each being a stock of the Research Institute for Microbial Diseases, Osaka University) and A2/Japan/305/57 [influenza A (H2N2), ATCC VR-100]. Alternately, the mammal can be immunized with an HA molecule obtained from these viruses, an HA polypeptide prepared by using the genetic recombination technology, a recombinant polypeptide containing the recognition site of the antibody of the present invention, namely, the antigen site of the stem region of an HA molecule therein or a synthetic polypeptide containing the antigen site of the stem region of an HA molecule therein. Next, spleen cells obtained from the animal thus immunized are fused with myeloma cells. From the hybridomas thus obtained, cells which produce an antibody having the characteristics (A) to (C) as will be specified below are selected and incubated to thereby give the target antibody according to the present invention.

(A) It has an avidity and a neutralization activity for viruses of the above-mentioned H1N1 and H2N2 subtypes.

(B) It has neither any avidity nor any neutralization activity for viruses of the H3N2 subtype such as A/Fukuoka/C29/85, A/Sichuan/2/87, A/Ibaraki/1/90, A/Suita/1/90, A/Kitakyushu/159/93 (each being a stock of the Research Institute for Microbial Diseases, Osaka University), A/Port Chalmers/1/73 [influenza A (H3N2), ATCC VR-810] and A2/Aichi/2/68 [influenza A, ATCC VR547] and influenza B virus strains such as B/Nagasaki/1/87 (a stock of the Research Institute for Microbial Diseases, Osaka University) and B/Allen/45 [influenza B, ATCC VR-102].

(c) It recognizes HA molecules of the H1N1 and H2N2 subtypes, does not inhibit the hemagglutination activity for which the globular head region of the HA molecule is responsible, but inhibits the membrane fusion activity for which the stem region of the HA molecule is responsible.

These hybridomas are prepared in accordance with the description of Nature, 256, 495–497 (1975). As a mouse to be immunized, a Balb/c mouse and an F1 mouse obtained by mating a Balb/c mouse with another mouse of a different series may be used. The immunization is effected, for example, thrice within 2 to 5 months by using 100 to 1000 HAU/animal of viral particles as an antigen. The feeding of the mouse and the collection of its spleen cells are carried out in a conventional manner.

As the myeloma cells, SP2/0-Ag14 (ATCC CRL1581), p3x63Ag8U.1 (ATCC CRL1597), p3x63Ag8 (ATCC TIB9) or p3x63-Ag8. 653 (ATCC CRL1580) may be suitably employed. The spleen cells and the myeloma cells are mixed together at a ratio of from 1:1 to 10:1. The fusion is effected by maintaining the mixture of these cells at 35° to 37° C. in a phosphate buffer solution (pH 7.2–7.4) containing NaCl (about 0.85%), dimethyl sulfoxide [10–20% (v/v)] and polyethylene glycol of a molecular weight of 1000 to 6000 for 1 to 5 minutes. By using an HAT medium, cells growing thereon are selected as fused cells. The fused cells are cloned by repeating the limiting dilution procedure at least thrice.

The hybridomas are incubated by a method commonly used for incubating animal cells. Thus the antibody of the present invention can be obtained in the medium. Alternately, the hybridomas may be transplanted into the peritoneal cavity of a nude mouse or a Balb/c mouse treated with pristane and grown therein. As a result, the antibody of the present invention can be accumulated in the ascites. Namely, 0.5 to 1 mg of pristans is inoculated into the peritoneal cavity of the mouse. Two to 3 weeks thereafter, $5 \times 10^6$ to $1 \times 10^7$ hybridomas are transplanted into the peritoneal cavity of the animal. Then the ascites, which is usually accumulated after 7 to 10 days, is taken out. The monoclonal antibody contained in the culture and the ascites may be purified by a conventional method.

The monoclonal antibody thus obtained recognizes the stem regions of HA molecules of the H1N1 and H2N2 subtypes and inhibits the membrane fusion activity of these viruses to thereby neutralize these viruses. Now the properties of this antibody will be described in greater detail.

(a) The results of the staining test indicate that the antibody of the present invention recognizes MDCK cells. (ATCC CCL34) infected with the H1N1 and H2N2 subtypes but does not recognize MDCK cells infected with the H3N2 subtype. The staining test is effected in accordance with the method described in J. Clin. Microbiol., 28, 1308–1313 (1990) by using four antibodies, namely, the monoclonal antibody of the present invention, rabbit anti-mouse immunoglobulin G serum, goat anti-rabbit immunoglobulin G serum, and peroxidase-rabbit anti-peroxidase complex.

(b) The results of the immunoprecipitation test indicate that the antibody of the present invention recognizes HA molecules of the H1N1 and H2N2 subtypes but does not recognize an HA molecule of the H3N2 subtype.

(c) In the hemagglutination test, the antibody of the present invention does not inhibit the hemagglutination activities of the H1N1, H2N2 and H3N2 subtypes.

(d) The antibody of the present invention recognizes a common conserved region characteristic of the stem regions of HA molecules of the H1N1 and H2N2 subtypes, which is specified by analyzing genes coding for the HA molecules, but does not recognize a common conserved region characteristic of the stem region of an HA molecule of the H3N2 subtype.

A gene coding for the HA molecule (hereinafter referred to simply as HA gene) is analyzed by the following method.

MDCK cells are infected with viral particles and the infected cells are harvested on the following day. Vital RNAs in the cells are extracted by using guanidine isothiocyanate. Next, an oligonucleotide primer complementary to the 3' terminus of the negative strand RNA of each of the H1N1, H2N2 and H3N2 subtypes (for example, the primer 5 represented by the SEQ ID No. 5 in the sequence listing) is prepared and cDNAs are synthesized by using this primer. To amplify these cDNAs, another oligonucleotide primer complementary to the 3' terminus of the positive strand RNA of each of the H1N1, H2N2 and H3N2 subtypes (for example, the primer 6 represented by the SEQ ID No. 6 in the sequence listing) is prepared. Then the cDNAs can be efficiently amplified by the polymerase chain reaction (PCR) method with the use of the primers 5 and 6. An HA gene of about 1.7 kbp contained in an amplified DNA is separated by agarose gel electrophoresis and then the second PCR is effected by using, for example, the primers 5 and 6. The DNA thus amplified is centrifuged by using 20% (w/v) polyethylene glycol 6000/2.5M NaCl to thereby give a purified precipitate fraction. Subsequently, sequence primers selected from among HA gene sequences of the subclasses of viruses are prepared. After labeling these primers with [$\gamma$-$^{32}$P]ATP, the labeled primers are annealed with the above-mentioned purified fraction, followed by sequencing by the dideoxy method with the use of a thermal cycler [BioTechniques, 9, 66–72 (1990)].

For example, the primers 7 to 14 represented respectively by the SEQ ID Nos. 7 to 14 in the sequence listing are sequence primers for the H1N1 subtype, the primers 15 to 23 represented respectively by the SEQ ID Nos. 15 to 23 in the sequence listing are sequence primers for the H2N2 subtype, and the primers 24 to 26 represented respectively by the SEQ ID Nos. 24 to 26 in the sequence listing are sequence primers for the H3N2 subtype. A part of the gene coding for the stem region of the HA molecule of the H1N1 subtype can be amplified and analyzed at a high efficiency by using the primers 9 and 13 as PCR primers and the primers 11 and 12 as sequence primers. A part of the gene coding for the stem region of the HA molecule of the H2N2 subtype can be amplified and analyzed at a high efficiency by using the primers 17 and 21 as PCR primers and the primers. 19 and 20 as sequence primers. Further, a part of the gene coding for the stem region of the HA molecule of the H3N2 subtype can be amplified and analyzed at a high efficiency by using the primers 24 and 26 as PCR primers and the primers 25 and 26 as sequence primers.

As common conserved regions in HA molecules of H1N1 and H2N2 subtypes, the TGLRN polypeptide sequence represented by the SEQ ID No. 1 in the sequence listing and the GITNKVNSVIEK polypeptide sequence represented by the SEQ ID No. 2 in the sequence listing in the stem regions in the HA molecules of the. H1N1 and H2N2 subtypes, which have been found out by the present inventors, can be cited. FIG. 1 is a schematic view of the tertiary structure of an HA molecule [Wiley et al., Nature, 289, 373–378 (1981)] and shows the position of the common conserved regions in HA molecules of H1N1 and H2N2 subtypes. As FIG. 1 shows, these polypeptide sequences, represented by the A region and the B region in the figure, are close to each other at the center of the stem region of the HA molecule. A monoclonal antibody C179, which is an example of the antibody of the present invention and produced by Hybridoma C179 (FERM BP-4517), recognizes A region (the TGLRN polypeptide sequence represented by the SEQ ID No. 1 in the sequence listing) and B region (the GITNKVNSVIEK polypeptide sequence represented by the SEQ ID No. 2 in the sequence listing) in the stem region of this HA molecule.

(e) In the neutralization activity test, the antibody of the present invention inhibits the plaque- or focus-forming abilities of the H1N1 and H2N2 subtypes but does not inhibit the plaque- or focus-forming ability of the H3N2 subtype. The neutralization activity test is carried out by the plaque reduction neutralization test or the influenza virus rapid focus reduction neutralization test described in the above-mentioned Journal of Clinical Microbiology. More specifically, the antibody is mixed with a virus and kept warm for a given period of time. Then MDCK cells are infected therewith and the neutralization activity is judged based on the reduction in the plaques or loci.

(f) In the fusion activity test, the antibody of the present invention inhibits the membrane fusion activities of the H1N1 and H2N2 subtypes but does not inhibit that of the H3N2 subtype. The fusion activity test is effected in accordance with a method described in Nature, 300, 658–659 (1982). Specifically, CV-1 cells (ATCC CCL70) are infected with a virus and treated with an antibody. Then the ability to inhibit the fusion activity is determined by examining the formation of polykaryons.

The antibody according to the present invention binds to the stem regions of HA molecules, inhibits the membrane fusion activities of the H1N1 and H2N2 subtypes and markedly neutralizes the infectious powers of these virus strains. Accordingly, the antibody of the present invention is usable in the prevention and treatment of influenza caused by the H1N1 and H2N2 subtypes. Usually, this antibody may be administered to an adult in a dose of from about 0.5 to 5000 mg, preferably from 5 to 500 mg. The antibody of the present invention may be formulated into preparations by mixing with, for example, common fillers, physiological saline, glucose solution, mannitol, methylcellulose or gelatin. This preparation may be in the form of a freeze-dried product which can be re-dissolved in an isotonic liquid such as physiological saline, a 5% glucose solution or ringers solution immediately before use. When the antibody of the present invention is to be administered to man, it is preferably used in the form of a chimetic antibody which is hardly recognized as a foreign substance in the human body. It is still preferable to use it as an artificial antibody obtained by transplanting the antigen recognition site alone into a human type antibody.

The antibody of this invention for example the monoclonal antibody C179 can bind to the stem regions of HA molecules, inhibit the membrane fusion activity of the H1N1 and H2N2 subtypes and markedly neutralize the infectious powers of these virus strains. Accordingly, the polypeptide capable of inducing the antibody which binds to the stem regions of HA molecules of H1N1 and H2N2 subtypes, inhibits the membrane fusion activities of the H1N1 and H2N2 subtypes and markedly neutralizes the infectious powers of these viruses (hereinafter this type antibody is referred to simply as C179 type antibody) is usable as a vaccine for influenza. Namely, the prevalence of influenza caused by the H1N1 and H2N2 subtypes can be prevented and treated by using a polypeptide, which has an antigenicity substantially the same as the stem regions of HA molecules of the H1N1 and H2N2 subtypes, as an immunogen. Examples of the immunogenic polypeptide include HA molecules prepared from the H1N1 and H2N2 subtypes and an HA polypeptide constructed by the genetic recombination technology. However, the globular head region of HA molecule is easy to become antigenic epitope and most frequently undergoes antigen mutation. So, a polypeptide having a stem region of HA molecule and lacking the globular head region of HA molecule is more effective as an antigen polypeptide which can induce C179 type antibody.

The polypeptide having an antigenicity which is substantially the same as that of the stem region of HA molecule and lacking the globular head region of HA modecule (hereinafter this polypeptide is referred to simply as stem region polypeptide) is obtained by enzymatic digestion and deletion of a globular head region of HA molecule or an HA polypeptide.

For example, the stem region polypeptide can be prepared by limitedly digesting HA molecules purified from vital particles of the H1N1 or H2N2 subtype with a protease. Alternately, the stem region polypeptide prepared by treating each of viral particles, a split vaccine obtained by inactivating vital particles, or an extract obtained by treating viral particles with a surfactant with a protease may be used. As the protease to be used herein, proteinases which can digest the globular head region in HA molecules without causing the loss of the antigenicity of the stem region are desirable. As an example of the proteinase usable in the present invention, proteinase K (EC 3.4.21.14; manufactured by Boehringer), which is an alkaline proteinase produced by *Tritirachium album*, may be cited. By using a proteinase which is comparable to this Proteinase K in the achievement of the digestion results, the stem region polypeptide of the present invention can be prepared. It is also possible to combine a proteinase with a peptidase and conduct the treatment with the-peptidase after the completion of the treatment with the proteinase. Since HA molecules exist in the form of rigid trimers in a solution, they are hardly digested with a protease. Accordingly HA molecules can be efficiently treated with the protease in the presence of a modifier such as guanidine hydrochloride or urea. The modifier may be used at such a concentration as to allow the digestion by the protease without causing irreversible denaturation of the target stem region polypeptide. When urea is used as the modifier, the digestion with the protease may be effected in the presence of from 0.1 to 8M, preferably from 1 to 3M of urea. This protease-treatment can be performed by using a resin such as Sepharose on which the protease has been mobilized. After the completion of the reaction, the protease-mobilized resin can be easily eliminated by centrifugation. The modifier and low molecular weight matters in the reaction mixture can be eliminated by dialysis. Thus protease-treated HA molecules can be prepared. The molecular weight of the protease-treated HA molecules can be measured by gel electrophoresis. Further, the target stem region polypeptide can be confirmed by measuring the avidity of the protease-treatment product for C179 type antybody and its haemagglutination activity.

The stem region polypeptide obtained by the protease-treatment is a polypeptide having an antigenicity substantially the same as that of the stem region in HA molecule (an avidity for C179 type antibody) and lacking the biological activity of the globular head region thereof (a hemagglutination activity). It consists of a polypeptide part originating in the HA1 stem region in HA molecule and another polypeptide part originating in HA2 therein. In this point, this polypeptide essentially differs from the above-mentioned vaccine of H. Glathe et. al. which consists of a polypeptide originating in HA2 alone.

The polypeptide having an antigenicity which is substantially the same as that of the stem region of HA molecule and lacking the globular head region of HA modecule is obtained by genetic recombination or by chemical synthesis. For example it is possible to get the polypeptide as follows. HA gene is prepared from a viral RNA, and a gene encoding a globular head region is deleted from HA gene by using some restriction enzyme or using PCR method. Then this HA gene, which is lacking a coding region of globular head region of HA molecule, is integrated into a vector and expressed in animal cell such as CV-1 cells. Then the antigenic activity of the stem region polypeptides can be detected by binding activity to C179 type antibody. The example of stem region polypeptide should have a common conserved region for stem region of HA molecule of H1N1 subtype and H2N2 subtype in its molecule and have the ability of inducing C179 type antibody. As the example of the stem region polypeptide, a polypeptide having a TGLRN polypeptide sequence represented by SEQ ID No. 1 in the sequence listing and a GITNKVNSVIEK polypeptide sequence represented by SEQ ID No. 2 in the sequence listing and having an antigenicity wherein the configuration of these sequence is substantially the same as that of the natural HA molecule of H1N1 and H2N2 subtypes can be obtained, isolated and used.

The example of stem region polypeptide may be the polypeptide having deletion, substitution, addetion, insertion, inversion, or replacement of amino acid, and it doesn't alter the antigenicity and C179 type antibody inducible activity. It may be the polypeptide deleting some part of C terminal and/or N terminal of stem region polypeptide or having a signal polypeptide of HA molecule at C terminal of stem region polypeptide or some part of globular head region in the stem region polypeptide.

When such a polypeptide is used as a vaccine, its antigenicity can be elevated by selecting an appropriate carrier. Examples of the carrier include albumin and polyamino acids. The vaccine of the present invention can be administered by the conventional active immunization method. More specifically, it can be administered in such an amount as to give an immunogenicity effective for the prevention or treatment one or more times by a method suitable for the preparation. The vaccine may be formulated into a pharmaceutical preparation by a conventional method. It may further contain an adjuvant for improving immune response.

The antibody, which recognizes a site common to the stem regions in HA molecules of the H3N2 subtype of human influenza A virus, can be prepared as a monoclonal antibody in the following manner. A mammal such as mouse, guinea pig or rabbit is immunized with an antigen. As the antigen, viral particles selected from among those of the H3N2 subtype may be used. Alternately, the mammal can be immunized with an HA molecule obtained from these viruses, an HA polypeptide prepared by using the genetic recombination technology, a recombinant polypeptide containing the recognition site of the antibody, namely, the antigen site of the stem region of an HA molecule therein or a synthetic polypeptide containing the antigen site of the stem region of an HA molecule therein. Next, spleen cells obtained from the animal thus immunized are fused with myeloma cells. From the hybridomas thus obtained, cells which produce an antibody having the characteristics (D) to (F) as will be specified below are selected and incubated to thereby give the target antibody.

(D) It has an avidity for virus of H3N2 subtype.

(E) It has no avidity for viruses of the H1N1 and H2N2 subtypes, and influenza B virus strains.

(F) It recognizes HA molecules of the H3N2 subtype, does not inhibit the hemagglutination activity for which the globular head region of the HA molecule is responsible.

These hybridomas are prepared in accordance with above description. As a mouse to be immunized, a Balb/c mouse and an F1 mouse obtained by mating a Balb/c mouse with another mouse of a different series may be used. The immunization is effected, for example, thrice within 2 to 5 months by using 100 to 1000 HAU/animal of viral particles as an antigen. The feeding of the mouse and the collection of its spleen cells are carried out in a conventional manner.

As the myeloma cells, SP2/0-Ag14, p3x63Ag8U.1, p3x63Ag8 or p3x63-Ag8.653 may be suitably employed. The spleen cells and the myeloma cells are mixed together at a ratio of from 1:1 to 10:1. The fusion is effected by maintaining the mixture of these cells at 35° to 37° C. in a phosphate buffer solution (pH 7.2–7.4) containing NaCl (about 0.85%), dimethyl sulfoxide [10–20% (v/v)] and polyethylene glycol of a molecular weight of 1000 to 6000 for 1 to 5 minutes. By using an HAT medium, cells growing thereon are selected as fused cells. The fused cells are cloned by repeating the limiting dilution procedure at least thrice.

The hybridomas are incubated by a method commonly used for incubating animal cells. Thus the antibody of the present invention can be obtained in the medium. Alternately, the hybridomas may be transplanted into the peritoneal cavity of a nude mouse or a Balb/c mouse treated with pristane and grown therein. As a result, the antibody of the present invention can be accumulated in the ascites. Namely, 0.5 to 1 mg of pristans is inoculated into the peritoneal cavity of the mouse. Two to 3 weeks thereafter, $5\times10^6$ to $1\times10^7$ hybridomas are transplanted into the peritoneal cavity of the animal. Then the ascites, which is usually accumulated after 7 to 10 days, is taken out. The monoclonal antibody contained in the culture and the ascites may be purified by a conventional method.

The monoclonal antibody thus obtained recognizes the stem regions of HA molecules of the H3N2 subtype. Now the properties of this antibody will be described in greater detail.

(g) The results of the staining test indicate that the antibody recognizes MDCK cells infected with the H3N2 subtype but does not recognize MDCK cells infected with the H1N1 subtype or H2N2 subtype.

(h) The results of the immunoprecipitation test indicate that the antibody recognizes HA molecules of the H3N2 subtype but does not recognize an HA molecule of the H1N1 and H2N2 subtypes.

(i) In the hemagglutination test, the antibody does not inhibit the hemagglutination activities of the H1N1, H2N2 and H3N2 subtypes.

(j) The antibody recognizes a common conserved region characteristic of the stem regions of HA molecules of the H3N2 subtype, which is specified by analyzing genes coding for the HA molecules, but does not recognize a common conserved region characteristic of the stem region of an HA molecule of the H1N1 and H2N2 subtypes.

As common conserved regions in HA molecules of H3N2 subtype, the TGMRN polypeptide sequence represented by the SEQ ID No. 3 in the sequence listing and the QINGKLNR(L/V)IEK polypeptide sequence represented by the SEQ ID No. 4 in the sequence listing in the stem regions in the HA molecules of the H3N2 subtype, which have been found out by the present inventors, can be cited. FIG. 2 is a schematic view of the tertiary structure of an HA molecule [Wiley et al., Nature, 289, 373–378 (1981)] and shows the position of the common conserved regions in the HA molecules of H3N2 subtype. As FIG. 2 shows, these polypeptide sequences, represented by the A' region and the B' region in the figure, are close to each other at the center of the stem region of the HA molecule. A monoclonal antibody AI3C, which is an example of the antibody which binds the conserved regions and is prodced by Hybridoma AI3C (FERM BP-4516), recognizes A' region (the TGMRN polypeptide sequence represented by the SEQ ID No. 3 in the sequence listing) and B' region [the GINGKLNR(L/V)IEK polypeptide sequence represented by the SEQ ID No. 4 in the sequence listing] in the stem region of this HA molecule.

The monoclonal antibody AI3C can bind specifically to the stem regions of HA molecules of H3N2 subtype (hereinafter this type antibody is referred to simply as AI3C type antibody). Accordingly, the polypeptide capable of inducing the AI3C type antibody is usable as a vaccine for influenza. Namely, the prevalence of influenza caused by the H3N2 subtype can be prevented and treated by using a polypeptide, which has an antigenicity substantially the same as the stem regions of HA molecules of the H3N2 subtype, as an immunogen. Examples of the immunogenic polypeptide include HA molecules prepared from the H3N2 subtype and an HA polypeptide constructed by the genetic recombination technology. However, the globular head region of HA molecule is easy to become antigenic epitope and most frequently undergoes antigen mutation. So, a stem region polypeptide is more effective as an antigen polypeptide which can induce AI3C type antibody.

The stem region polypeptide having an antigenicity which is substantially the same as that of the stem region of HA molecule of H3N2 subtype is obtained by enzymatic digestion and deletion of a globular head region of HA molecule or an HA polypeptide.

For example, the stem region polypeptide can be prepared by limitedly digesting HA molecules purified from vital particles of the H3N2 subtype with a protease. Alternately, the stem region polypeptide prepared by treating each of vital particles, a split vaccine obtained by inactivating viral particles, or an extract obtained by treating viral particles with a surfactant with a protease may be used. As the protease to be used herein, proteinase which can digest the globular head region in HA molecules without causing the loss of the antigenicity of the stem region are desirable. As an example of the proteinase usable in the present invention, Proteinase K may be cited. By using a proteinase which is comparable to this Proteinase K in the achievement of the digestion results, the stem region polypeptide of the present invention can be prepared. It is also possible to combine a proteinase with a peptidase and conduct the treatment with the peptidase after the completion of the treatment with the proteinase. Since HA molecules exist in the form of rigid trimers in a solution, they are hardly digested with a protease. Accordingly HA molecules can be efficiently treated with the protease in the presence of a modifier such as guanidine hydrochloride or urea. The modifier may be used at such a concentration as to allow the digestion by the protease without causing irreversible denaturation of the target stem region polypeptide. When urea is used as the modifier, the digestion with the protease may be effected in the presence of from 0.1 to 8M, preferably from 1 to 3M of urea. This protease-treatment can be performed by using a resin such as Sepharose on which the protease has been mobilized. After the completion of the reaction, the Protease-immobilized resin can be easily eliminated by centrifugation. The modifier and low molecular weight matters in the reaction mixture can be eliminated by dialysis. Thus protease-treated HA molecules can be prepared. The molecular weight the protease-treated HA molecules can be measured by gel electrophoresis. Further, the target stem region polypeptide can be confirmed by measuring the avidity of the protease-treatment, product for AI3C type antibody and its haemagglutination activity.

The stem region Polypeptide obtained by the protease-treatment is a polypeptide having an antigenicity substantially the same as that of the stem region in HA molecule (an avidity for AI3C type antibody) and lacking the biological activity of the globular head region thereof (a hemagglutination activity ). It consists of a polypeptide part originating in the HA1 stem region in HA molecule and another polypeptide part originating in HA2 therein. In this point, this polypeptide essentially differs from the above-mentioned vaccine of H. Glathe et. al. which consists of a Polypeptide originating in HA2 alone.

The stem region polypeptide having an antigenicity which is substantially the same as that of the stem region of HA molecule of H3N2 subtype is obtained by genetic recombination or by chemical synthesis. For example it is possible to get the polypeptide as follows. HA gene is prepared from a viral RNA of H3N2 subtype, and a gene encoding a globular head region is deleted from HA gone by using some restriction enzyme or using PCR method. Then this HA gene, which is lacking a coding region for globular head region of HA molecule, is integrated into a vector and expressed in animal cell such as CV-1 cells. Then the antigenic activity of these stem region polypeptides can be detected by binding activity to AI3C type antibody. The example of stem region polypeptide should have a common conserved region for stem region of HA molecule of H3N2 subtype in its molecule and have the ability of inducing AI3C type antibody. As the example of the stem region polypeptide, a polypeptide having a TGMRN polypeptide sequence represented by SEQ ID No. 3 in the sequence Listing and a QINGKLNR(L/V)IEK polypeptide sequence represented by SEQ ID No. 4 in the sequence listing and exhibiting an antigenicity wherein the configuration of these sequence is substantially same as that natural HA molecule of H3N2 subtype can be obtained, isolated and used.

The example of stem region polypeptide may be the polypeptide having deletion, substitution, addtion, insertion, inversion, or replacement of amino acid, and it doesn't alter the antigenicity and AI3C type antibody inducible activity. It may be the polypeptide deleting some part of C terminal and/or N terminal of stem region polypeptide or having a signal polypeptide of HA molecule at C terminal of stem region polypeptide or some part of globular head region in the stem region polypeptide.

When such a polypeptide is used as a vaccine, its antigenicity can be elevated by selecting an appropriate carrier. Examples of the carrier include albumin and polyamino acids. The vaccine of the present invention can be administered by the conventional active immunization method. More specifically, it can be administered in such an amount as to give an immunogenicity effective for the prevention or treatment one or more times by a method suitable for the preparation. The vaccine may be formulated into a pharmaceutical preparation by a conventional method. It may further contain an adjuvant for improving immune response.

The dose of the stem region polypeptide of this invention to be administered depends on, for example, the properties of the vaccine employed, the concentration of the polypeptide in a preparation and the administration route. Usually it may be administered to an adult in a dose of from 1 μg to 100 mg, preparably from 10 μg to 10 mg.

FIG. 6 is a graph showing the survival ratio of a group infected with influenza virus.

DETAILED DESCRIPTION OF THE PREFERRED EMBODIMENT

Figure 1:
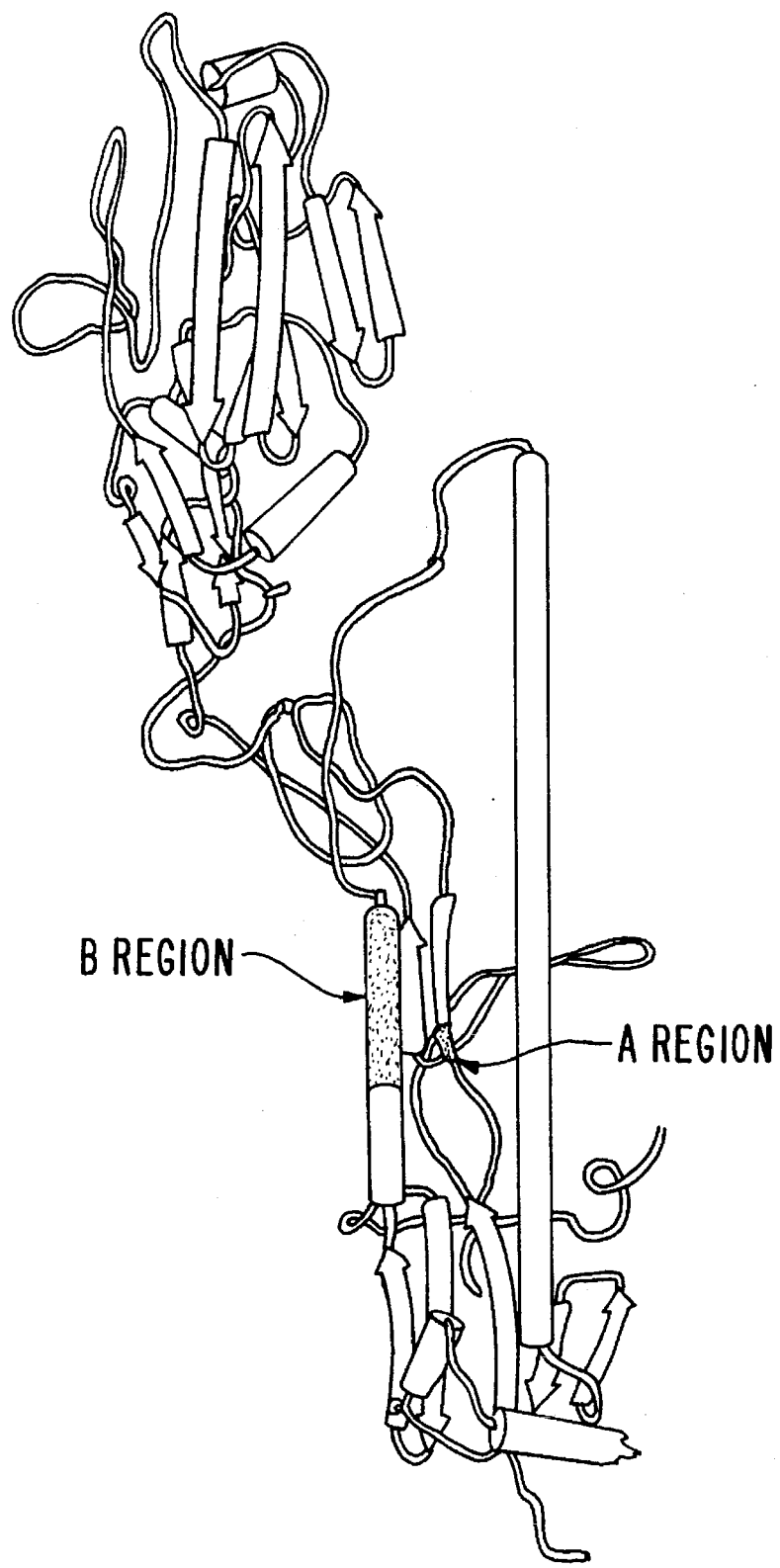
FIG. 1 is a schematic view of the tertiary structure of a HA molecule and shows the position of common conserved regions in HA molecules of H1N1 and H2N2 subtypes.

To further illustrate the present invention in greater detail, and not by way of limitation, the following Examples will be given.

EXAMPLE 1

Preparation of viruses:

Virus strains of the H1N1 subtype used included A/PR/8/34, A/Bangkok/10/83, A/Yamagata/120/86, A/Osaka/930/88, A/Suita/1/89 and A1/FM/1/47 were used. Virus strains of the H2N2 subtype used included A/Okuda/57, A/Adachi/2/57, A/Kumamoto/1/65, A/Kaizuka/2/65 and A/Izumi/5/65 were used. Virus strains of the H3N2 subtype, used included A2/Aichi/2/68, A/Fukuoka/C29/85, A/Sichuan/2/87, A/Ibaraki/1/90,A/Suita/1/90 and A/Kitakyushu/59/93 were used. A strain of influenza B virus used was B/Nagasaki/1/87. Each strain was inoculated into the allantoic cavity of an embryonated hen egg aged 11 days, incubated at 34° C. for 4 days and then harvested.

EXAMPLE 2

Preparation of monoclonal antibodies:

(1) Balb/c mice were immunized with two doses of A/Okuda/57 strain (320 HAU) prepared in the above Example 1, which had been suspended in Freund's complete adjuvant before use, via intraperitoneal injection one month apart. One month thereafter, the mice were boosted by intraperitoneally injecting a suspension of the same antigen (320 HAU) in PBS. Three days thereafter, the spleen of each animal was taken out and thus spleen cells were prepared.

Mouse myeloma cells were prepared by incubating p3x63Ag8 cells in a DME medium containing 10% of fetal bovine serum for 2 days after passage and then washing with physiological saline before cell fusion. The spleen cells were mixed with the myeloma cells at a ratio by cell count of 1:5. After centrifuging and removing the supernatant, the precipitated cell clusters were thoroughly loosened and then added to 1 ml of a mixture [polyethylene glycol 4000 (2 g), MEM (2 ml), and dimethyl sulfoxide] under stirring. After maintaining at 37° C. for 5 minutes, MEM was slowly added thereto so as to adjust the total amount to 10 ml. After the mixture was centrifuged, the supernatant was removed and the cell clusters were gently loosened. 30 ml of a normal medium (PRMI-1640 containing 10% of fetal bovine serum) was added thereto and the cells were slowly suspended with the use of a measuring piper.

The suspension was pipetted into a 96-well incubation plate and incubated in an incubator containing 5% of $CO_2$ at 37° C. for 24 hours. Then HAT medium was added thereto and the incubation was continued for 10 to 14 days. Subsequently, a part of the culture supernatant was sampled and subjected to hybridoma screening.

(2) To obtain a monoclonal antibody undergoing a cross reaction between influenza A virus subtypes, the above-mentioned culture supernatant, which had not been diluted, was used as a primary antibody and a staining test on MDCK cells infected with the three subtypes (H1N1, H2N2 and H3N2) was effected. The staining test was carried out in accordance with the abovementioned method described in Journal of Clinical Microbiology. Specifically, the MDCK cells infected with the human influenza virus subtype strains (H1N1: A/Yamagata/120/86, H2N2: A/Okuda/57, H3N2: A/Fukuoka/C29/85) were rinsed with PBS (pH 7.4) on 96-well microtiter plates (Falcon 3072; manufactured by Becton Dickinson Labware) and fixed with absolute ethanol at room temperature for 10 minutes. Then these cells were continuously treated with 4 antibodies [the above-mentioned culture supernatant containing the monoclonal antibody, rabbit anti-mouse immunoglobulin G serum (manufactured by Organon Teknika) diluted 1000-fold, goat anti-rabbit immunoglobulin G serum (manufactured by Organon Teknika) diluted 500-fold, and peroxidase-rabbit Anti-peroxidase complex (manufactured by Organon Teknika) diluted 1000-fold, each for 40 minutes, and the cells thus treated were washed with PBS. Finally, the peroxidase reaction was effected by the method of Graham and Karnovsky [see J. Histochem. Cytochem., 14, 291–302 (1966)] with the use of 0.01% $H_2O_2$ and 0.3 mg/ml of 3,3'-diaminobenzidine tetrahydrochloride in PBS. The stained cells were observed under an ordinary light microscope to sort antibodies recognizing respectively the H1N1 subtype-infected MDCK cells and the H2N2 subtype-infected MDCK cells. Next, the cells in the wells where the production of these antibodies had been confirmed were taken out and treated by the limiting dilution thrice to thereby clone the target cells. The hybridoma strain thus cloned was named Hybridoma C179, while the monoclonal antibody produced thereby was named monoclonal antibody C179.

The Hybridoma C179 has been deposited on Jan. 28, 1993 with National Institute of Bioscience and Human-Technology, Agency of Industrial Science and Technology (1–3, Higashai 1 chome Tsukuba-shi Ibaraki-ken,305 JAPAN), under accession number FERM P-13388, and on Dec. 27, 1993 this deposit was converted to deposit at National Institute of Bioscience and Human-Technology, Agency of Industrial Science and Technology in accordance with the Budapest Treaty under the accession number FERM BP-4517.

(3) $5\times10^6$/animal of the above-mentioned hybridomas were intraperitoneally administered to Balb/c mice treated with pristane. Ten to 21 days thereafter, the ascites of a mouse having ascites cancer thus induced was sampled and centrifuged at 3000 rpm for 5 minutes to thereby remove solid components and give an ascites fluid. This fluid contained about 5 mg/ml of the monoclonal antibody C179 (hereinafter referred to simply as C179). After purifying with Protein A-Sepharose 4B (manufactured by Pharmacia), C179 was confirmed as an antibody of the IgG2a type.

EXAMPLE 3

Properties of monoclonal antibody:

(1) A 100-fold dilution of the ascites fluid as described in the above Example 2-(3) was diluted stepwise and the staining test as described in the above Example 2-(2) was effected to examine the antigen recognizing characteristics of C179. The H1N1 subtype strains used included A/PR/8/34, A/Bangkok/10/83, A/Yamagata/120/86, A/Osaka/930/88,A/Suita/1/89 and A1/FM/1/47. The H2N2 subtype strains used included A/Okuda/57, A/Adachi/2/57, A/Kumamoto/1/65, A/Kaizuka/2/65 and A/Izumi/5/65. The H3N2 subtype strains used included A/Aichi/2/68, A/Fukuoka/C29/85, A/Sichuan/2/87, A/Ibaraki/1/90, A/Suita/1/90, A/Kitakyushu/159/93. Further, B/Nagasaki/I/87 was used as an influenza B virus strain.

C179 recognized all of the H1N1 subtype and H2N2 subtype strains but did not recognize the H3N2 subtype strains and the influenza virus B strain.

(2) The neutralization activity of the antibody was determined by effecting the above-mentioned influenza virus rapid focus reduction neutralization test in accordance with the description of Arch. Virol., 86, 129–135 (1985) and Microbiol. Immunol., 29, 327–335 (1985). The ascites fluid of the above Example 2-(3) was used as an antibody, to which was added thrice by volume as much a receptor destroying enzyme (RDE: manufactured by Takeda Chemical Industries, Ltd.) solution before the use. After reacting at 37° C. for 18 hours, the RDE was inactivated by heating at 56° C. for 45 minutes. Finally, a 16-fold dilution of the ascites fluid was prepared and subjected as a test sample to the determination as will be described hereinbelow.

Namely, 10/well of MDCK cells were pipetted into 96-well microplates. On the next day, the abovementioned antibody (16-fold dilution) diluted in 4 steps was mixed with the equal amount of the suspension of each virus strain of 30 focus-forming units/well prepared in the above Example 3-(1), and the mixture was kept at 37° C for 1 hour. Then 25 µl of this mixture was pipetted into the wells of the microtiter plates containing the above-mentioned MDCK cells and kept at 37° C. for 30 minutes. Then the solution in each well was removed and the well was rinsed with PBS. Next, MEM containing 0.5% of tragacanth gum (manufactured by Wako Pure Chemical Industries, Ltd.) and 5 µg/ml of trypsin was added thereto. After being kept at 37° C. for 20 to 24 hours, the solution added above was removed and each well was rinsed with PBS. Then the cells were fixed by treating with absolute ethanol at room temperature for 10 minutes. Then these cells were dried and stained in accordance with the staining test as described in the above Example 2-(2). After the completion of the staining, the cells were rinsed with tap water and dried. Then the stained foci were counted under a light microscope.

C179 inhibited the focus formation of all of the H1N1 subtype and H2N2 subtype strains and had a potent virus neutralization activity. On the other hand, it exerted no effect on the focus formation by the H3N2 subtype strains and the influenza B virus strain. The plaque reduction neutralization test gave similar results.

(3) The hemagglutination inhibition (HI) activity of the antibody was examined by the following method. The antibody (32-fold dilution) which had been treated with RDE in the same manner as the one described in the above Example 3-(2) was diluted stepwise and mixed with each virus strains (16 HAU) as described in the above Example 3-(1) to effect reaction at room temperature for 30 minutes. After adding avian erythrocytes and well mixing, the effect of the antibody on the haemagglutination activity of each virus strain was examined. It was found that the hemagglutination activity of none of the virus strains was affected by C179.

(4) The fusion inhibition activity of the antibody was determined by the above method as described in Nature, 300, 658–659 (1982) with a few slight modifications. Namely, monolayer cultures of CV-1 cells were infected with each of the virus strains as described in the above Example 3-(1). 24 hours after the inoculation, the cells were washed twice with DMEM and then kept at 37° C. in DMEM containing 10 μg/ml of trypsin for 15 minutes. Subsequently, the cells were washed twice with DMEM and kept at 37° C. in the ascites fluid of the above Example 2-(3) diluted with DMEM for 30 minutes. Thereafter, the cells were treated for 2 minutes at 37° C. with a fusion medium (RPMI free from $Na_2CO_3$, containing 0.2% bovine serum albumin, 10 mM MES and 10 mM HEPES) adjusted to pH 5.0. Then the cells were washed twice with DMEM to remove the fusion medium, and then kept at 37° C. for 3 hours in DMEM containing 2% of fetal bovine serum. Next, the cells were fixed with absolute methanol and subjected to Giemsa's staining. Then the formation of polykaryons was examined under a light microscope.

C179 inhibited the polykaryon formation by all of the H1N1 and H2N2 subtype strains but did not inhibit the formation by the H3N2 subtype strain and the influenza B virus strain. As discussed above, C179 is an antibody which specifically recognizes the H1N1 and H2N2 subtypes, inhibits membrane fusion of viruses and exhibits a neutralization activity. Table 1 summarizes these results.

TABLE 1

| Virus | Antibody titers of C179 measured by | | | |
|---|---|---|---|---|
| | Staining[a] | Neutralization[b] | HI[c] | Fusion inhibition[d] |
| H1N1 | | | | |
| A/PR/8/34 | 1,638,400 | 512 | <32 | + |
| A/Bangkok/10/83 | 1,638,400 | 512 | <32 | + |
| A/Yamagata/120/86 | 409,600 | 1,024 | <32 | + |
| A/Osaka/930/88 | 409,600 | 512 | <32 | + |
| A/Suita/1/89 | 409,600 | 1,024 | <32 | + |
| A1/FM/1/47 | 409,600 | 512 | <32 | + |
| H2N2 | | | | |
| A/Okuda/57 | 1,638,400 | 1,024 | <32 | + |
| A/Adachi/2/57 | 1,638,400 | 1,024 | <32 | + |
| A/Kumamoto/1/65 | 409,600 | 1,024 | <32 | + |
| A/Kaizuka/2/65 | 409,600 | 2,048 | <32 | + |
| A/Izumi/5/65 | 409,600 | 1,024 | <32 | + |
| H3N2 | | | | |
| A2/Aichi/2/68 | <100 | <16 | <32 | – |
| A/Fukuoka/C29/85 | <100 | <16 | <32 | – |
| A/Sichuan/2/87 | <100 | <16 | <32 | – |
| A/Ibaraki/1/90 | <100 | <16 | <32 | – |
| A/Suita/1/90 | <100 | <16 | <32 | – |
| A/Kitakyushu/159/93 | <100 | <16 | <32 | – |
| B | | | | |
| B/Nagasaki/1/87 | <100 | <16 | <32 | – |

[a]Staining test.
[b]Neutralization test.
[c]Hemagglutination inhibition test.
[d]Fusion inhibition test.

In the above Table 1, each number represents the dilution ratio of the ascites fluid of the Example 2-(3), a staining titer is expressed in the maximum dilution ratio of the ascites fluid whereby cells can be stained in the staining test, while a neutralization activity is expressed in the maximum dilution ratio of the ascites fluid whereby the formation of foci can be suppressed up to a level corresponding to one half of the focus count in the control lot wherein no antibody is added. Symbol + means that polykaryon formation is completely inhibited by a 1000-fold dilution of the ascites fluid, while symbol – means that polykaryon formation is not inhibited even by using a 10-fold dilution of the ascites fluid. A 32-fold dilution of the ascites fluid shows no HI activity.

EXAMPLE 4

Determination of epitope:

(1) It was determined by immunoprecipitation that the protein recognized by C179 was HA molecules. Specifically, MDCK cells were infected with an H2N2 subtype strain A/Okuda/57 via adsorption for 30 minutes and then incubated in MEM wherein methionine was replaced with 10 μCi of [$^{35}$S]methionine for 24 hours to thereby label the infected cells. Next, the cells were harvested and suspended again in an RIPA buffer solution [50 mM Tris (pH 7.4), 150 mM NaCl, 1 mM EDTA, 1% Nonidet P-40, 1% deoxycholate and 0.1% SDS]. After removing the insoluble matters by centrifuging, a supernatant was obtained. Then this supernatant was mixed with C179 and kept at 4° C. for 1 hour. Protein A-Sepharose CL4B beads were added thereto and kept at room temperature for 2 hours to thereby allow the beads to adsorb the immunoprecipitate. These beads were collected, washed 5 times with an RIPA buffer solution and boiled to thereby liberate the protein binding to C179. Then this protein was electrophoresed on an SDS-12.5% polyacrylamide gel. The gel was fixed, soaked in a 1M sodium salicylate solution and dried to effect autoradiography. The labeled protein binding to C179 was thus identified with the HA molecule of A/Okuda/57 based on its electrophoretic pattern. The H1N1 subtype strains, other H2N2 subtype strains and the H3N2 subtype strain were also tested in the same manner. It was found that C179 underwent immunoprecipitation specifically together with all of the H1N1 and H2N2 Subtype strains but showed no avidity on the HA molecule of the H3N2 subtype.

(2) In the presence of C179, MDCK cells infected with the H1N1 subtype or the H2N2 subtype were incubated to thereby give an antigen variant having no sensitivity to C179. More specifically, A/Suita/1/89 of the H1N1 subtype and A/Izumi/5/65 of the H2N2 subtype were used each as a parent strain. MDCK cells infected with each of these virus strains were incubated in the presence of C179. Thus variants capable of growing in the presence of C179 were separately isolated in a pure state from plaques of the MDCK cells. A variant of A/Suita/1/89 was named A/Suita/1/89(R) while a variant of A/Izumi/5/65 was named A/Izumi/5/65(R). These two variants had no reactivity with C179 both in the staining test and in the neutralization test. Each of these variants was a mild infection strain having a low plaque forming ability, having no pathogenicity to mice used as test animals and capable of growing only in cultured cells.

(3) In order to specify the antigen recognition site of the antibody, a HA gene was analyzed.

(a) Synthesis of primers: Primers 5 to 26 were synthesized with a DNA synthesizer, freed from the protective group and purified by ion exchange HPLC (TSK Gel, DEAE-2SW Column). After desalting with Sep-pack C18, about 50 μg portions of DNAs were obtained.

(b) MDCK cells infected with A/Suita/1/89 were harvested and guanidine isothiocyanate was added thereto. The mixture was repeatedly sucked and discharged 5 times with the use of a syringe to thereby dissolve the cells. After the completion of the dissolution, the cell extract was layered over a cesium chloride solution and ultracentrifuged. The precipitate on the bottom of a centrifuging tube was dissolved in a buffer solution, treated with phenol and chloroform, and precipitated from ethanol. The RNA thus recovered was used as a sample of virus genome RNA. Next, cDNAs were synthesized by using the primer 5 and the cDNAs thus synthesized were amplified by the PCR method with the use of the primers 5 and 6. The cDNAs thus amplified were next separated by agarose gel electrophoresis to thereby elute a cDNA band of 1.7 kbp corresponding to the HA gene. This cDNA was further amplified by the PCR method with the use of the primers 5 and 6. To the amplified fragment was added. 20% (w/v) of polyethylene glycol in 60% (v/v) of a 2.5M NaCl solution. After centrifuging, a purified precipitate fraction was obtained.

Next, the base sequence of the gene thus purified was determined by the dideoxy method with the use of a thermal cycler as described in the above-mentioned Bio-Techniques wherein primers 7 to 14 which were sequencing primers for the H1N1 subtype labeled with [γ-$^{32}$p] were employed. More specifically, 2 pml of a primer was annealed with 1 pmol of the purified fragment by heating to 95° C. for 3 minutes and then quenching. After adding Taq polymerase, the mixture was kept at 72° C. for 10 minutes in a buffer solution containing deoxynucleotide and dideoxynucleotide, thus effecting a polymerase extension reaction. To complete the extension reaction, the reaction mixture was transferred into the thermal cycler, where a cycle of heating at 90° C. for 1 minute, at 55° C. for 2 minutes and at 72° C. for 3 minutes was repeated 10 times. After the completion of the cycling, the reaction mixture was heated to 95° C. for 3 minutes in the presence of formamide, quenched in ice and then electrophoresed on an 8% denatured polyacrylamide gel. After the completion of the electrophoresis, the gel was dried and exposed with the use of an X-ray film. Then the base sequence was read out to thereby determine the base sequence of the whole HA gene represented by the SEQ ID No. 27 in the sequence listing.

(c) The base sequence of the HA gene of A/Suita/1/89(R) was analyzed in accordance with the method as described in the above Example 4-(3)-(b). Thus the base sequence of the whole HA gene was determined and compared with the HA gene of the parent strain. As a result, it was found out that the HA gene of the variant underwent nucleotide replacement at three positions. More precisely, G of the base No. 627, G of the base No. 736 and C of the base No. 1018 in the HA gene of the parent strain mutated respectively into A, A and A. When an HA molecule was cleaved with a protease at one site, its vital infectivity was activated. After the cleavage, the larger polypeptide was called HA1 while the smaller one was called HA2. These polypeptides were bound to each other via an S—S bond. This mutation was accompanied by amino acid replacements at the 189-, 225- and 318-positions in HA1. Amino acid residues at the 189- and 225-positions were located in a highly variable region and the replacement at the 318-position (Thr→Lys; ACA→AAA on the nucleotide level) was responsible for the C179 nonreactivity of the variant. In the present specification, amino acid position in HA molecule are assigned in accordance with the H3 numbering method as described in Virus, 11, 257–266 (1961).

(d) The base sequences of HA genes of A/Izumi/5/65 and A/Izumi/5/65(R) were analyzed in accordance with the method as described in the above Example 4-(3)-(b), except that primers 15 to 23 which were sequencing primers for the H2N2 subtype were used. The base sequence of the HA gene of A/Izumi/5/65 is represented by the SEQ ID No. 28 in the sequence listing. The HA gene of this variant underwent nucleotide replacement at one position. Namely, T of the base No. 1197 in the HA gene of the parent strain mutated into A. This mutation was accompanied by an amino acid replacement at the 52-position of HA2. This replacement at the 52-position (Val→Glu; GTA→GAA on the nucleotide level) was responsible for the C179 nonreactivity of the variant.

(e) In order to specify the amino acid sequence around the 318-position of HA1 and the amino acid sequence around the 52-position of HA2 of the HA molecule of each of A/PR/8/34, A/Bangkok/10/83, A/Yamagata/120/86 and A/Osaka/930/88 of the H1N1 subtype, A/Okuda/57, A/Adachi/2/57, A/Kumamoto/1/65 and A/Kaizuka/2/65 of the H2N2 type and A2/Aichi/2/68, A/Fukuoka/C29/85, A/Sichuan/2/87, A/Ibaraki/1/90 and A/Suita/1/90 of the H3N2 subtype, a part of each HA gene was sequenced.

In the case of the strains of the H1N1 subtype, cDNA of the RNA genome of each virus was synthesized in accordance with the method as described in the above Example 4-(3)-(b) and this cDNA was amplified by PCR with the use of the primers 9 and 13. By using the DNA fragment thus obtained as a template, the base sequence was determined by the dideoxy method with the use of a thermal cycler and the primers 11 and 12.

In the case of the strains of the H2N2 subtype, cDNA of the RNA genome of each virus was synthesized in accordance with the method as described in the above Example 4-(3)-(b) and this cDNA was amplified by PCR with the use of the primers 17 and 21. By using the DNA fragment thus obtained as a template, the base sequence was determined similarly by the dideoxy method with the use of the primers 19 and 20.

In the case of the strains of the H3N2 subtype, cDNA of the RNA genome of each virus was synthesized in accordance with the method as described in the above Example 4-(3)-(b) and this cDNA was amplified by PCR with the use of the primers 24 and 26. By using the DNA fragment thus obtained as a template, the base sequence was determined similarly by the dideoxy method with the use of the primers 25 and 26.

In the H1N1 and H2N2 subtypes, the TGLRN polypeptide sequence at the 318- to 322-positions in the HA1 region (A region) represented by the SEQ ID No. 1 in the sequence listing and a the GITNKVNSVIEK polypeptide sequence at the 47- to 58-positions in the HA2 region (B region) represented by the SEQ ID No. 2 in the sequence listing are conserved. In the H3N2 subtype, on the other hand, the TGMRN polypeptide sequence at the 318- to 322-position in the HA1 region (A' region) represented by the SEQ ID No. 3 in the sequence listing and the QINGKLNR(L/V)IEK polypeptide sequence at the 47- to 58-positions in the HA2 region (B' region) represented by the SEQ ID No. 4 in the sequence listing are conserved. The A region differs from the A' region by one amino acid, while the B region differs from the B' region by 5 or 6 amino acid residues. The differences among these regions are responsible for the difference in-the antigen recognition of the antibody. Thus the antibody could not react with the H3N2 subtype in the serological and fusion inhibition tests.

As FIG. 1 shows, the TGLRN polypeptide sequence of the A region represented by the SEQ ID No. 1 in the sequence listing and the GITNKVNSVIEK polypeptide sequence of the B region represented by the SEQ ID No. 2 in the sequence listing are close to each other at the center of the stem region of the HA molecule. C179 recognizes both of these sequences and thus this site corresponds to the epitope of C179. C179 binds to the stem region of the HA molecule and thus inhibits the membrane fusion action of the HA molecule and neutralizes the virus.

H1N1 subtype: The sequence of the base Nos. 1017 to 1031 of the HA gene of the A/Suita/1/89 represented by the SEQ ID No. 27 in the sequence listing codes for the A region, while the sequence of the base Nos. 1191 to 1226 thereof codes for the B region. The SEQ ID No. 29 in the sequence listing shows a part of the HA gene of A/PR/8/34, wherein the sequence of the base Nos. 76 to 90 codes for the A region while the sequence of the base Nos. 250 to 285 codes for the B region. The SEQ ID No. 30 in the sequence listing shows a part of the HA gene of A/Bangkok/10/83, wherein the sequence of the base Nos. 76 to 90 codes for the A region while the sequence of the base Nos. 250 to 285 codes for the B region. The SEQ ID No. 31 in the sequence listing shows a part of the HA gene of A/Yamagata/120/86 wherein the sequence of the base Nos. 76 to 90 codes for the A region while the sequence of the base Nos. 250 to 285 codes for the B region. The SEQ ID No. 32 in the sequence listing shows a part of the HA gene of A/Osaka/930/88 wherein the sequence of the base Nos. 76 to 90 codes for the A region while the sequence of the base Nos. 250 to 285 codes for the B region.

H2N2 subtype: The sequence of the base Nos. 1007 to 1021 of the HA gene of the A/Izumi/5/65 represented by the SEQ ID No. 28 in the sequence listing codes for the A region, while the sequence of the base Nos. 1181 to 1216 thereof codes for the B region. The SEQ ID No. 33 in the sequence listing shows a part of the HA gene of A/Okuda/57, wherein the sequence of the base Nos. 94 to 108 codes for the A region while the sequence of the base Nos. 268 to 303 codes for the B region. The SEQ ID No. 34 in the sequence listing shows a part of the HA gene of A/Adachi/2/57, wherein the sequence of the base Nos. 103 to 117 codes for the A region while the sequence of the base Nos. 277 to 312 codes for the B region. The SEQ ID No. 35 in the sequence listing shows a part of the HA gene of A/Kumamoto/1/65, wherein the sequence of the base Nos. 104 to 118 codes for the A region while the sequence of the base Nos. 278 to 313 codes for the B region. The SEQ ID No. 36 in the sequence listing shows a part of the HA gene of A/Kaizuka/2/65, wherein the sequence of the base Nos. 88 to 102 codes for the A region while the sequence of the base Nos. 262 to 297 codes for the B region.

H3N2 subtype: The SEQ ID Nos. 37, 38, 39, 40 and 41 in the sequence listing respectively show a part of HA genes of A2/Aichi/2/68, A/Fukuoka/C29/85, A/Sichuan/2/87, A/Ibaraki/1/90 and A/Suita/1/90. In each case, the sequence of the base Nos. 84 to 98 codes for the A' region while the sequence of the base Nos. 258 to 293 codes for the B' region.

Figure 2:
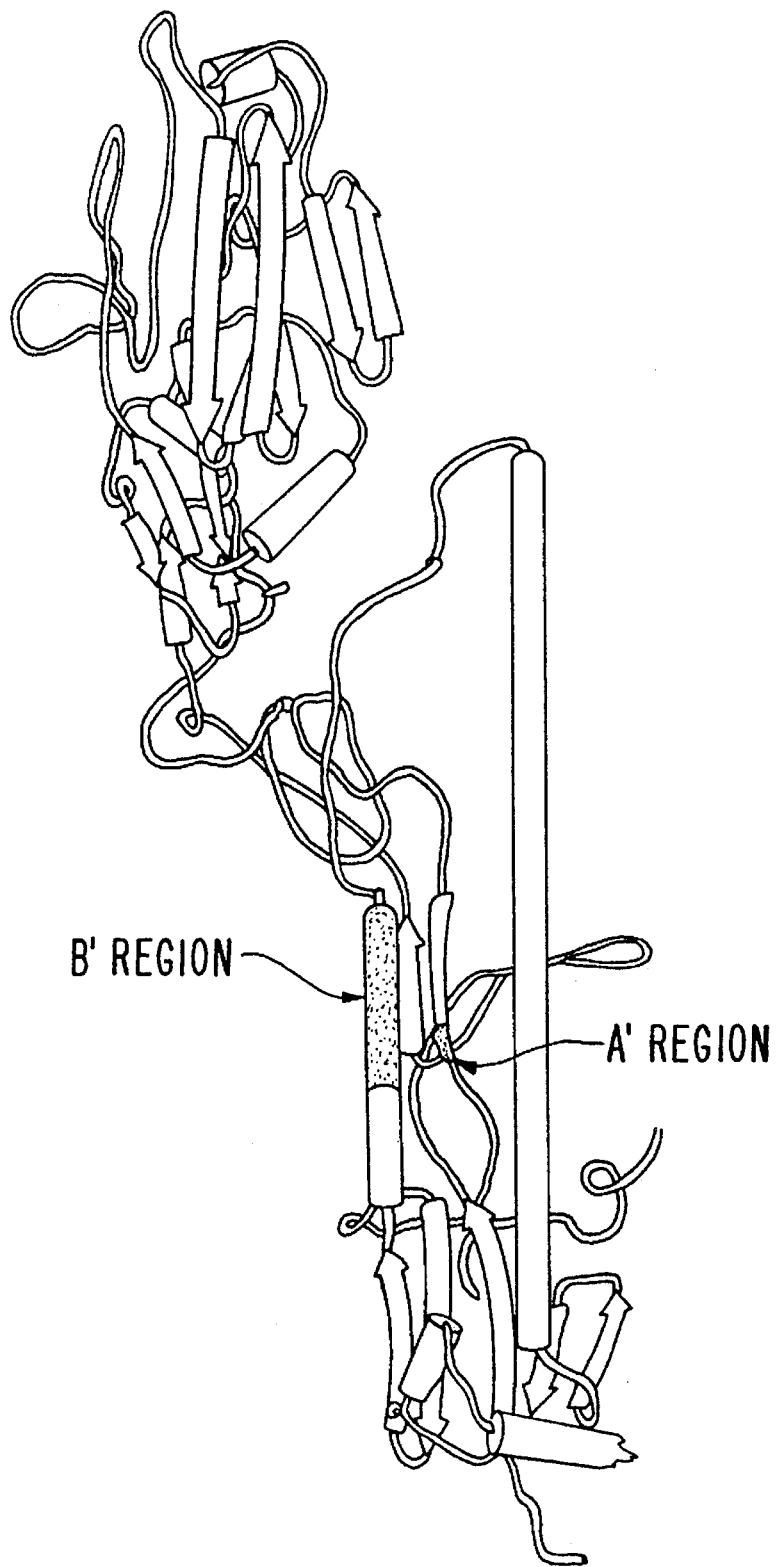
FIG. 2 is a schematic view of the tertiary structure of a HA molecule and shows the position of common conserved regions in HA molecules of H3N2 subtype.

As FIG. 2 shows, the TGMRN polypeptide sequence of the A' region represented by the SEQ ID No. 3 in the sequence listing and the QINGKLNR(L/V)IEK polypeptide sequence of the B' region represented by the SEQ ID No. 4 in the sequence listing are close to each other at the center of the stem region of the HA molecule.

EXAMPLE 5

Preventive effect on influenza virus:

In order to examine the preventive effect of C179, an influenza virus infection test was carried out by using mice. One ml/animal of a C179 solution (1 mg/ml in PBS) was intraperitoneally administered to 10 Balb/c mice. After 1 day, 25 μl of a 1000-fold dilution of A1/FM/1/47 (4000 HAU) of the H1N1 subtype was intranasally administered. As a control, 12 mice were inoculated with the virus alone.

Figure 3:
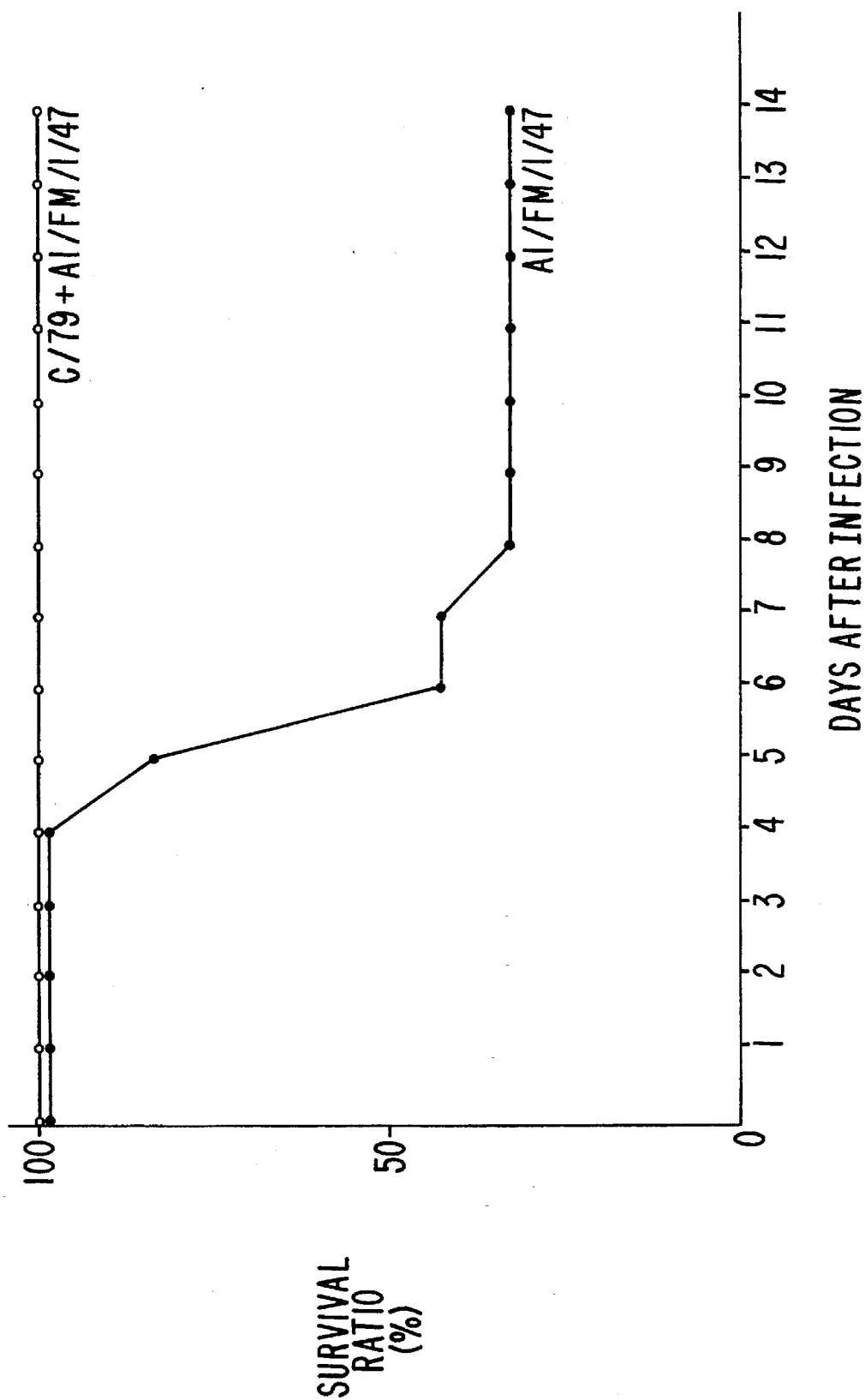
FIG. 3 is a graph showing the survival ratio of a group infected with influenza virus.

As FIG. 3 shows, 8 mice in the control group died (two mice after 5 days, five after 6 days and one after 8 days). Other surviving mice in this group were extremely weakened. In contrast, the mice administered with C179 showed no abnormality and all remained healthy even after 14 days.

FIG. 3 is a graph showing the survival ratios of the C179-administered group and the control group wherein the ordinate indicates the survival ratio while the abscissa indicates the time (days) after the infection with the virus.

Reference 1

1. Preparation of viruses:

A strain of H5N3 subtype used was A/whistling swan/Shimane/476/83. A strain of H6N6 subtype used was A/whistling swan/Shimane/37/80. A strain of H7N7 subtype used was A/turfted duck/Shimane/124R/80. A strain of HSN4 subtype used was A/turky/Ontario/6118/68. A strain of H10N7 subtype used was A/chicken/Germany"N"/49. Each strain is a stock of the Research Institute for Microbial Diseases. A/chicken/Germany"N"/49 has the amino acid sequences represented respectively by SEQ ID No. 3 and SEQ ID No. 4 in the HA molecule, but other strain lack these sequences.

Each strain was inoculated into the allantoic cavity of an embryonated hen egg aged 11 days, incubated at 34° C. for 4 days and then harvested.

2. Preparation of monoclonal antibodies:

(1) Balb/c mice were immunized with two doses of A2/Aichi/57 strain (320 HAU) prepared in the above Example 1, which had been suspended in Freund's complete adjuvant before use, via intraperitoneal injection one month apart. One month thereafter, the mice were boosted by intraperitoneally injecting a suspension of the same antigen (320 HAU) in PBS. Three days thereafter, the spleen of each animal was taken out and thus spleen cells were prepared.

Mouse myeloma cells were prepared by incubating p3x63Ag8 cells in a DME medium containing 10% of fetal bovine serum for 2 days after passage and then washing with physiological saline before cell fusion. The spleen cells were mixed with the myeloma cells at a ratio by cell count of 1:5. After centrifuging and removing the supernatant, the precipitated cell clusters were thoroughly loosened and then added to 1 ml of a mixture [polyethylene glycol 4000 (2 g), MEM (2 ml), and dimethyl sulfoxide] under stirring. After maintaining at 37° C. for 5 minutes, MEM was slowly added thereto so as to adjust the total amount to 10 ml. After the mixture was centrifuged, the supernatant was removed and the cell clusters were gently loosened. 30 ml of a normal medium (PRMI-1640 containing 10% of fetal bovine serum) was added thereto and the cells were slowly suspended with the use of a measuring piper.

The suspension was pipetted into a 96-well incubation plate and incubated in an incubator containing 5% of $CO_2$ at 37° C. for 24 hours. Then HAT medium was added thereto and the incubation was continued for 10 to 14 days. Subsequently, a part of the culture supernatant was sampled and subjected to hybridoma screening.

(2) To obtain a monoclonal antibody undergoing a cross reaction between H3N2 subtype and H10N7 subtype, the abovementioned culture supernatant, which had not been diluted, was used as a primary antibody and a staining test on MDCK cells infected with the three subtypes (H3N2, H10N7 and H1N1) was effected. The staining test was carried out in accordance with the above-mentioned method described in example 2-(2). Specifically, the MDCK cells infected with the influenza virus subtype strains (H3N2: A2/Aichi/2/68, H10N7: A/chicken/Germany"N"/49, H1N1: A/PR/8/34) were rinsed with PBS (pH 7.4) on 96-well microtiter plates (Falcon 3072) and fixed with absolute ethanol at room temperature for 10 minutes. Then these cells were continuously treated with 4 antibodies [the abovementioned culture supernatant containing the monoclonal antibody, rabbit anti-mouse immunoglobulin G serum diluted 1000-fold, goat anti-rabbit immunoglobulin G serum diluted 500-fold, and peroxidase-rabbit anti-peroxidase complex diluted 1000-fold, each for 40 minutes, and the cells thus treated were washed with PBS. Finally, the peroxidase reaction was effected by the method of Graham and Karnovsky with the use of 0.01% $H_2O_2$ and 0.3 mg/ml of 3,3'-diaminobenzidine tetrahydrochloride in PBS. The stained cells were observed under an ordinary light microscope to sort antibodies recognizing respectively the H3N2 subtype-infected MDCK cells and the H10N7 subtype-infected MDCK cells. Next, the cells in the wells where the production of these antibodies had been confirmed were taken out and treated by the limiting dilution thrice to thereby clone the target cells. The hybridoma strain thus cloned was named Hybridoma AI3C, while the monoclonal antibody produced thereby was named monoclonal antibody AI3C.

The tradename of this monoclonal antibody is monoclonal antibody F49 (manufactured by Takara Shuzo Co., Ltd.)

The Hybridoma AI3C was deposited on Nov. 11, 1992 at Fermentation Research Institute, Agency of Industrial Science and Technology (1-3, Higashi 1 chome Tsukuba-shi Ibaraki-ken 305, JAPAN), under accession number FERM P-13275, and on Dec. 27, 1993 this deposit was converted to deposit at National Institute of Bioscience and Human-Technology, Agency of Industrial Science and Technology in accordance with the Budapest Treaty under the accession number FERM BP-4516.

(3) $5\times10^6$/animal of the above-mentioned hybridomas were intraperitoneally administered to Balb/c mice treated with pristane. Ten to 21 days thereafter, the ascites of a mouse having ascites cancer thus induced was sampled and centrifuged at 3000 rpm for 5 minutes to thereby remove solid components and give an ascites fluid. This fluid contained about 5 mg/ml of the monoclonal antibody AI3C (hereinafter referred to simply as AI3C). AI3C was purified with Protein A-Sepharose 4B.

3. Properties of monoclonal antibody:

(1) A 100-fold dilution of the ascites fluid as described in the Reference 1-2-(3) was diluted stepwise and the staining test as described in the above Example 2-(2) was effected to examine the antigen recognizing characteristics of AI3C. The H1N1 subtype strains used included A/PR/8/34, A/Bangkok/10/83, A/Yamagata/120/86, A/Osaka/930/88, A/Suita/1/89 and A1/FM/1/47. The H2N2 subtype strains used included A/Okuda/57, A/Adachi/2/57, A/Kumamoto/1/65, A/Kaizuka/2/65 and A/Izumi/5/65. The H3N2 subtype strains used included A/Aichi/2/68, A/Fukuoka/C29/85, A/Sichuan/2/87, A/Ibaraki/1/90, and A/Kitakyushu/159/93. A/Suita/1/90. Further, B/Nagasaki/1/87 was used as an influenza B virus strain and the strains described in the Reference 1-1 were used.

AI3C recognized all of the H3N2 subtype and A/chicken/Germany"N"/49 but did not recognize the H1N1 subtype strains, H2N2 subtype strains, the influenza virus B strain, and other subtype strains.

(2) The HI activity of the antibody was examined by the following method. The antibody (32-fold dilution) which had been treated with RDE in the same manner as the one described in the above Example 3-(2) was diluted stepwise and mixed with each virus strains (16 HAU) as described in the above Reference 1-1 and 1-3-(1) to effect a reaction at room temperature for 30 minutes. After adding avian erythrocytes and well mixing, the effect of the antibody on the haemagglutination activity of each virus strain was examined. It was found that the hemagglutination activity of none of the virus strains was affected by AI3C.

4. Determination of epitope:

It was determined by immunoprecipitation that the protein recognized by AI3C was HA molecules. Specifically, MDCK cells were infected with an H3N2 subtype strain A2/Aichi/2/68 via adsorption for 30 minutes and then incubated in MEM wherein methionine was replaced with 10 μCi of [$^{35}$S]methionine for 24 hours to thereby label the infected cells. Next, the cells were harvested and suspended again in an RIPA buffer solution [50 mM Tris (pH 7.4), 150 mM NaCl, 1 mM EDTA, 1% Nonidet P-40, 1% deoxycholate and 0.1% SDS]. After removing the insoluble matters by centrifuging, a supernatant was obtained. Then this supernatant was mixed with AI3C and kept at 4° C. for 1 hour. Protein A-Sepharose CL4B beads were added thereto and kept at room temperature for 2 hours to thereby allow the beads to adsorb the immunoprecipitate. These beads were collected, washed 5 times with an RIPA buffer solution and boiled to thereby liberate the protein binding to AI3C. Then this protein was electrophoresed on an SDS-12.5% polyacrylamide gel. The gel was fixed, soaked in a 1M sodium salicylate solution and dried to effect autoradiography. The labeled protein binding to AI3C was thus identified with the HA molecule of A2/Aichi/2/68 based on its electrophoretic pattern. The H1N1 subtype strains, H2N2 subtype strains, other H3N2 subtype strains, and strains described in above Reference 1-1 were also tested in the same manner. It was found that AI3C underwent immunoprecipitation specifically together with all of the H3N2 subtype strains and A/chicken/Germany"N"/49 but showed no avidity on the HA molecule of the other subtypes.

EXAMPLE 6

Construction of the stem region polypeptide:

(1) Synthesis of primers: Primers 27 to 30 were synthesized with a DNA synthesizer, freed from the protective group and purified by ion exchange HPLC (TSK Gel, DEAE-2SW Column). After desalting with Sep-pack C18, about 50 µg portions of DNAs were obtained.

Primers 27 and 28 have the sequences of 5'-terminal of HA gene of H2N2 subtype, and primers 29 and 30 have the complimentary sequences of 3'-terminal of one. The base sequences of primers 27 to 30 are represented respectively by the SEQ ID Nos. 42 to 45.

(2) MDCK cells infected with A/Okuda/57 were harvested and guanidine isothiocyanate was added thereto. The mixture was repeatedly sucked and discharged 5 times with the use of a syringe to thereby dissolve the cells. After the completion of the dissolution, the cell extract was layered over a cesium chloride solution and ultracentrifuged. The precipitate on the bottom of a centrifuging tube was dissolved in a buffer solution, treated with phenol and chloroform, and precipitated from ethanol. The RNA thus recovered was used as a sample of virus genome RNA. Next, cDNAs were synthesized by using the primer 5 and the cDNAs thus synthesized were amplified by the PCR method with the use of the primers 27 and 29. The cDNAs thus amplified were next separated by agarose gel electrophoresis to thereby elute a cDNA band of 1.8 kbp corresponding to the HA gene. This cDNA was further amplified by the PCR method with the use of the primers 28 and 30. To the second amplified fragment of 1.8 kbp was added 20% (w/v) of polyethylene glycol in 60% (v/v) of a 2.5M NaCl solution. After centrifuging, a purified precipitate fraction was obtained.

(3) The base sequence of HA gene for A/Okuda/57 was analyzed by the methods described in example 4-(3)-(b), (d). The base and amino acid sequences of it are represented by the SEQ ID No. 46. In the sequence represented by the SEQ ID No. 46, the sequence of the base Nos. 1 to 5 originates in primer 28, the sequence of base Nos. 6 to 48 is the non-coding regions, the sequence of base Nos. 49 to 93 is the coding region for signal polypeptide, the sequence of base Nos. 94 to 231 is the coding region for the stem region of N-terminal domain of HA molecule, the sequence of base Nos. 232 to 873 is the coding region for the globular head region of HA molecule, the sequence of base Nos. 874 to 1734 is the coding region for the stem region of C-terminal domain of HA molecule, the sequence of base Nos. 1735 to 1775 is the non coding region, and the sequence of base Nos. 1776 to 1783 originates in primer 30.

(4) Construction of the plasmids.

(a) The terminals of the 1.8 kbp DNA fragment prepared in example 6-(2) was treated by T4 DNA polymerase for creating blunt ends. It was ligated with a plasmid pHSG299 (manufactured by Takara Shuzo Co. Ltd., ) digested with restriction enzyme Sinai by T4 DNA ligase. *E. coli* JM109 was transformed with the ligated sample and some kanamycin resistant transformants were gotten. A plasmid pH2-299 which containing HA gene was prepared from one of these transformants. *E. coli* JM109 harboring the plasmid pH2-299 was named *Escherichia coli* JM109/pH2-299 and has been deposited on Feb. 16, 1993 with National Institute of Bioscience and Human-Technology, Agency of Industrial Science and Technology under the accession number FERM P-13431.

(b) A plasmid pEF-BOS/neoA, which is a shuttle vector for mammalian cell and *E. coli*, was constructed by A 2.6 kbp BamHI DNA fragment from pMAMneo-s (manufactured by Clontech Lab. Inc.) inserting into AatII site of a plasmid pEF-BOS [Nucleic Acids Research, 18, 5322 (1990)].

Then the 1.8 kbp NheI DNA fragment from pH2-299 and pEF-BOS/neoA digested with restriction enzyme XbaI were ligated by T4 DNA ligase. *E. coli* JM109 was transformed with the ligated sample and some ampicillin resistant transformants was gotten. A plasmid which containing the HA gene was prepared from one of these transformants and named pEBNaH2. *E. coli* JM109 harboring the plasmid pEBNaH2 was named *Escherichia coli* JM109/pEBNaH2.

(c) Primers 31 and 32, represented respectively by the SEQ ID Nos. 47 and 48, were synthesized by using DNA synthesizer and purified with HPLC (TSK gel, DEAE-2SW column) and Sep-pak C18. The primer 31 has a complementary sequence to the sequence of the base Nos. 207 to 231 in the SEQ ID No. 46. The primer 32 has a sequence to sequence of the base Nos. 874 to 899 (but base No. 876 is changed A to C) in the SEQ ID No. 46. The amplification of 3.8 kbp DNA fragment which is lacking the region coding for the globular head region of HA molecule from pH2-299 was tried by PCR method using these primers.

The PCR reaction was performed with 50 pmol of primer 31, 50 pmol primer 32 and pH2-299 prepared from *Escherichia coli* JM109/pH2-299 (FFRM P-13431) as template. The reaction was performed for 25 cycles with each cycle consisting of 1 minute at 90° C., 2 minutes at 55° C. 3 minutes at 72° C. And a 3.8 kbp fragment was amplified. Then this fragment was phosphorylated by T4 kinase, treated with T4 DNA ploymerase for creating blunt ends, and ligated by T4 DNA ligase to make plasmid. *E. coli* JM109 was transformed with the ligeted palsmid and some kanamycin resistant transformante were gotten. A plasmid prepared from one of these transformante was named p299H2Sn-c, that was containing the HA gene which was lacking the region coding for the globular head region (the base Nos. 232 to 873 in the SEQ ID No. 46) and having the coding region for the stem region of N-terminal domain of HA molecule and C terminal domain of HA molecule joined. A 1.1 kbp DNA fragment containing the gene coding for the stem region polypeptide was prepared from p299H2Sn-c by digestion of restriction enzyme NheI. The base sequence for this fragment and the amino acid sequence of the stem region polypeptide translated from this DNA fragment were represented respectively by the SEQ ID No. 49 and SEQ ID No. 50 in the sequence listing. A plasmid that had the gene coding for the stem region polypeptide was constructed by ligation of the 1.1 kbp NheI fragment from p299H2Sn-c and pEF-BOS/neoA digested with XbaI with T4 DNA ligase. *E. coli* JM109 was transformed with the ligated sample and some ampicillin resistant transformats were gotten. A plasmid containing the gene coding for the stem region polypeptide was named pENH2dH01, and *E. coli* JM109 harboring the plasmid pENH2dH01 was named *Escherichia coli* JM109/pENH2dH01 and has been deposited on Feb. 16, 1993 with National Institute of Bioscience and Human-Technology, Agency of Industrial Science and Tecnology in accordance with the Budapest Treaty under the accession number FERM BP-4190.

(5) Expression of polypeptides:

The plasmid pENH2dH01 containing the gene coding for the stem region polypeptide was prepared from *Escherichia coli* JM109/pENH2dH01 and the plasmid pEBNaH2 containing HA gene was prepared from *Escherichia coli* JM109/pEBNaH2.

Trypsin treated CV-1 cells ($5\times10^6$ cells) were washed with 20 ml 10% FCS-MEM in one time, and 20 ml PBS in two times, and suspended in 1 ml PBS. The 0.8 ml part of it and the plasmid pENH2dH01 (30 mg) were put into a cuvette for Genepulser™ (manufactured by BioRad), and the cuvette was set into Genepulser™. The cells and plasmid were treated in 250 V, 960 mFD by Genepulser™. After the sample was put at 0° C. for 10 minutes, the cells were suspended in 30 ml 10% FCS-MEM and 5 ml each was cultured in a dish (6 cm) for two days.

The CV-1 cells transformed with the plasmid pENH2dH01 were washed with PBS (pH7.4) and fixed with absolute ethanol at room temperature for 10 minutes. Focus staining was done by successive treatment of the cells with C179 (1:1000), rabbit anti-mouse immunoglobulin G serum (1:1000), goat anti-rabbit immnuoglobulin G serum (1:500), and peroxidase-rabbit antiperoxidase (PAP) complex (1:1000). Each treatment was 40 minutes long and was followed by a washing with PBS. The peroxide reaction was developed for about 5 minutes by the methed of Graham and Karnousky in which 0.01% $H_2O_2$ and 0.3 mg of 3,3'-diaminobenzidene tetrahydrochloride per ml in PBS were used.

The CV-1 cells transformed with pENH2dH01 were stained by immunostaining with C179. So the expressed the stem region polypeptide had normal structure of high dimension for the stem region of HA molecule in spite of lacking of the globular head region of HA molecule. As this polypeptide is lacking the globular head region of HA molecule which is apt to become antigenic determinants and to arise antigenic mutation, it will be able to become the antigen that induce the antibodys recognizing the stem region of HA molecule and counteracting both H1N1 subtype and H2N2 subtype influenza viruses, like C179 type antibody. So this stem region polypeptide is useful for the influenza vaccine.

Similarly, the CV-1 cells transformed with pEBNaH2 were stained by immunostaining method with C179, so the expressed polypeptide also had normal structure of high dimension for the stem region of HA molecule.

EXAMPLE 7

Construction of the stem region polypeptide:

(1) Synthesis of primers: Primers 33 to 35 were synthesized with a DNA synthesizer, freed from the protective group and purified by ion exchange HPLC (TSK Gel, DEAE-2SW Column). After desalting with Sep-pack C18, about 50 µg portions of DNAs were obtained.

Primers 33 has the sequences of 5'-terminal of HA gene of H3N2 subtype, and primers 34 and 35 have the complimentary sequences of 3'-terminal of one. The nucleotide sequences of primers 33 to 35 are represented respectively by the SEQ ID Nos. 51 to 53.

(2) MDCK cells infected with A2/Aichi/2/68 were harvested and guanidine isothiocyanate was added thereto. The mixture was repeatedly sucked and discharged 5 times with the use of a syringe to thereby dissolve the cells. After the completion of the dissolution, the cell extract was layered over a cesium chloride solution and ultracentrifuged. The precipitate on the bottom of a centrifuging tube was dissolved in a buffer solution, treated with phenol and chloroform, and precipitated from ethanol. The RNA thus recovered was used as a sample of virus genome RNA. Next, cDNAs were synthesized by using the primer 5 and the cDNAs thus synthesized were amplified by the PCR method with the use of the primers 33 and 34. The cDNAs thus amplified were next separated by agarose gel electrophoresis to thereby elute a cDNA band of 1.8 kbp corresponding to the HA gene. This cDNA was further amplified by the PCR method with the use of the primers 33 and 35. To the second amplified fragment of 1.8 kbp was added 20% (w/v) of polyethylene glycol in 60% (v/v) of a 2.5M NaCl solution. After centrifuging, a purified precipitate fraction was obtained.

(3) The base sequence of HA gene for A2/Aichi/2/68 was analyzed by the methods described in example 4-(3)-(b),(d). The base and amino acid sequences of it are represented by the SEQ ID No. 54 in the sequence listing. In the sequence No. 54, the sequence of the base Nos. 1 to 8 originates in primer 33, the sequence of base Nos. 9 to 36 is the non coding regions, the sequence of base Nos. 37 to 84 is the coding region for signal polypeptide, the sequence of base Nos. 85 to 246 is the coding region for the stem region of N-terminal domain of HA molecule, the sequence of base Nos. 247 to 903 is the coding region for the globular head region of HA molecule, the sequence of base Nos. 904 to 1769 is the coding region for the stem region of C-terminal domain of HA molecule, the sequence of base Nos. 1735 to 1769 is the non coding region, and the sequence of base Nos. 1770 to 1777 originates in primer 35.

(4) Construction of the plasmids:

(a) The terminals of the 1.8 kbp DNA fragment prepared in example 7-(3) was treated by T4 DNA polymerase for creating blunt ends. It was ligated with a plasmid pUC118 (manufactured by Takara Shuzo Co. Ltd., ) digested with HincII by T4 DNA ligase. *E. coli* JM109 was transformed with the ligated sample and some ampicillin resistant transformants were gotten. A plasmid which containing HA gene was prepared from one of these transformants and named pU118H3xxn. *E. coli* JM109 harboring the plasmid pU118H3xxn was named *Escherichia coli* JM109/pU118H3xxn and has been deposited on Mar. 30, 1993 with National Institute of Bioscience and Human-Technology, Agency of Industrial Science and Technology under the accession number FERM P-13567.

(b) Primers 36 and 37, represented respectively by the SEQ ID Nos. 55 and 56, were synthesized by using DNA synthesizer and purified with HPLC (TSK gel, DEAE-2SW column) and Sep-pak C18. The primer 36 has a complementary sequence to the sequence of the base Nos. 227 to 246 in the SEQ ID No. 54. The primer 37 has a sequence to sequence of the base Nos. 904 to 923 in the SEQ ID No. 54. The amplification of 4.3 kbp DNA fragment which was lacking the region coding for the globular head region of HA molecule from pUl18H3xxn was tried by PCR method using these primers. The PCR reaction was performed with 50 pmol of primer 36, 50 pmol primer 37 and pU118H3xxn prepared from *Escherichia coli* JM109/pU118H3xxn (FFRM P-13567) as template. The reaction was performed for 25 cycles with each cycle consisting of 1 minute at 90° C. 2 minutes at 55° c., 3 minutes at 72° c. And a 4.3 kbp fragment was amplified. Then this fragment was phosphorylated by T4 kinase, -treated with T4 DNA ploymerase for creating blunt ends, and ligated by T4 DNA ligase to make plasmid. *E. coli* JM109 was transformed with the ligeted palsmid and some ampicillin resistant transformante were gotten. A plasmid prepared from one of these transformante was named p118H3dH01, that was containing the HA gene which was lacking the region coding for the globular head region (the base Nos. 247 to 903 in the SEQ ID No.54) and having the coding region for the stem region of N-terminal domain of HA molecule and C terminal domain of HA molecule joined. A 1.1 kbp DNA fragment containing the gene coding for the stem region polypeptide was prepared from p118H3dH01 by digestion of NheI and XbaI. The nucleotide sequence for this fragment and the amino acid sequence of the stem region polypeptide translated from this DNA fragment were represented respectively by the SEQ ID No. 57 and SEQ ID No. 58 in the sequence listing. A plasmid that had the gene coding for the stem region polypeptide was constructed by ligation of the 1.1 kbp NheI fragment from p118H3dH01 and pEF-BOS/neoA digested with XbaI with T4 DNA ligase. *E. coli* JM109 was transformed with the ligated sample and some ampicillin resistant transformats were gotten. A plasmid prepared from one of these transfmats was named pENH3dH01 that was containing the gene coding for the stem region polypeptide, and *E. coli*. JM109 harboring the plasmid pENH3dH01 was named *Escherichia coli* JM109/pENH3dH01. *Escherichia coli* JM109/pENH3dH01 was deposited on Mar. 30, 1993 at National Institute of Bioscience and Human-Technology, Agency of Industrial Science and Technology under accession number FERM P-13568, and on Dec. 27, 1993 this deposit was converted to deposit at National Institute of Bioscience and Human-Technology, Agency of Industrial Science and Technology in accordance with the Budapest Treaty under the accession number FERM BP-4518.

(5) Expression of the stem region polypeptide:

The plasmid pENH3dH01 containing the gene coding for the stem region polypeptide was prepared from *Escherichia coli* JM109/pENH3dH01.

Trypsin treated CV-1 cells ($5 \times 10^6$ cells) were washed with 20 ml 10% FCS-MEM in one time, and 20 ml PBS in two times, and suspended in 1 ml PBS. The 0.8 ml part of it and the plasmid pENH3dH01 (30 mg) were put into a cuvette for Genepulser™, and the cuvette was set into Genepulser™. The cells and plasmid were treated in 250 V, 960 mFD by Genepulser™. After the sample was put at 0° C. for 10 minutes, the cells were suspended in 30 ml 10% FCS-MEM and 5 ml each was cultured in a dish (6 cm) for two days.

The CV-1 cells transformed with the plasmid pENH3dH01 were washed with PBS (pH7.4) and fixed with absolute ethanol at room temperature for 10 minutes. Focus staining was done by successive treatment of the cells with AI3C (1:1000), rabbit anti-mouse immunoglobulin G serum (1:1000), goat anti-rabbit immnuoglobulin G serum (1:500), and peroxidase-rabbit anti-peroxidase (PAP) complex (1:1000). Each treatment was 40 minutes long and was followed by a washing with PBS. The peroxide reaction was developed for about 5 minutes by the methed of Graham and Karnousky in which 0.01% $H_2O_2$ and 0.3 mg of 3.3-diaminobenzidene tetrahydrochloride per ml in PBS were used. The CV-1 cells transformed with pENH3dH01 were stained by immunostaining with AI3C. So the expressed the stem region polypeptide peptides had normal structure of high dimension for the stem region of HA molecule of H3N2 subtype in spite of lacking of the globular head region of HA molecule. This polypeptide is lacking the globular head region of HA molecule which is apt to become antigenic determinants and to arise antigenic mutation, it will be able to become the antigen that induce the antibodys recognizing the stem-region of HA molecule of H3N2 subtype influenza viruses, like AI3C type antibody. So this stem region polypeptide is useful for the influenza vaccine.

EXAMPLE 8 preparation of antigen polypeptide:

(1) preparation of HA molecules

Vital particles (40 mg) of A/Yamagata/32/89 prepared in Example 1 were suspended in 27 ml of 5 mM Tris-HCl (pH 8.0). After adding 3 ml of 20% NP-40, the mixture was maintained at 37° C. for 30 minutes. Then it was centrifuged and the supernatant was collected and filtered through a 0.8 μm filter unit (Millex PF: manufactured by Millipore). Subsequently the filtrate was loaded on an ion exchange membrane (memSep DEAE: manufactured by Millipore) and washed with the same buffer. Further, HA molecules were eluted with the same buffer containing 1M of NaCl.

(2) Treatment of HA molecule with proteinase

In an N-ethylmorpholine buffer solution (pH 7.5), the HA molecules (2.6 μg) prepared in the above Example 8-(1) were digested with 4-pmol portions of lysyl endopeptidase (manufactured by Wako Pure Chemical Industries, Ltd.), V8 protease (manufactured by Sigma Chemical Co.) and chymotrypsin (manufactured by Boehringer) at 37° C. for 1 hour.

The HA molecules (2.6 μg) prepared in the above Example 8-(1) were denatured by maintaining at 42° C. in the presence of 2M of urea for 1 hour. Next, these molecules were digested with 4-pmol portions of lysyl endopeptidase, V8 protease, chymotrypsin, subtilisin (manufactured by Boehringer), proteinase K (manufactured by Boehringer), pronase (manufactured by Boebringer) and thermolysin (manufactured by Boehringer) in a 50 mM tris hydrochloride buffer solution (pH 7.6) at 37 C. for 12 hours and then dialyzed against PBS.

A portion of each digestion mixture was collected and the digested fragments were analyzed by the dot-blot method with the use of C179 and SDS polyacrylamide gel electrophoresis.

The dot-blot method was effected in the following manner.

1 μl of the digestion mixture was loaded onto a nitrocellulose filter (manufactured by MSI) and dried. The same procedure was repeated 5 times to thereby load 5 μl of the digestion mixture in total. Then blocking was carried out with the use of Blockace (manufactured by Snow Brand Milk Products Co.). Next, it was reacted with a 500-fold dilution of a C179 solution at room temperature for 1 hour. After washing with a tris hydrochloride buffer solution containing 0.02% of Tween 20, washing was further effected with a tris hydrochloride buffer solution (pH 7.6) for 10 minutes thrice.

Then it was reacted with a 500-fold dilution of an alkaline phosphatase-labeled goat anti-mouse immunoglobulin G solution (manufactured by Orgenics, Ltd.) at room temperature for 1 hour and washed in the same manner as the one described above. Finally, the alkaline phosphatase reaction was performed by using a solution of nitro blue tetrazolium 5-bromo-4-chloro-3-indolyl phosphate in carbon/sodium carbonate (pH 9.0) in the presence of 1 mM of $MgCl_2$.

As a result, it was found out that most of the HA molecules remained undigested when treated with each of these proteases in the absence of urea. The HA molecules, which had been denatured with urea, employed as a substrate were not digested with V8 protease, thermolysin and pronase. When lysyl endopeptidase, chymotrypsin and subtilisin were used, the digestion proceeded excessively and the antigenicity for C179 completely disappeared. When proteinase K was used, on the other hand, it was confirmed that the molecules were digested and polypeptide fragments having an avidity for C179 were formed.

(3) Preparation of stem region polypeptide

To the HA molecules (250 μg/1400 μl) prepared in Example 8-(1) were successively added 100 μl of 1M Tris-HCl (pH 7.6) and 500 μl of 8M urea and the resulting mixture was maintained at 42° C. for 1 hour. To this solution was added 2000 μl of an immobilized Proteinase K gel and maintained at 37° C. for 7 hours under shaking. After centrifuging, the reaction mixture thus obtained was dialyzed against PBS for 12 hours and thus the stem region polypeptide was obtained. The mobilized Proteinase K gel was prepared in the following manner. 4 mg of Proteinase K (manufactured by Boehringer) was dissolved in 1 ml of $H_2O$ and the pH value of the solution was adjusted to 5.0 with 0.1N HCl. After adding 1 ml of ECH-Sepharose (manufactured by Pharmacia) and 1 ml of 0.2M EDC (pH 5.0) thereto, the mixture was maintained at 4° C. for 24 hours. This gel was washed with 10 ml portions of PBS thrice to thereby give the immobilized Proteinase K gel.

(4) Properties of stem region polypeptide

By using the stem region polypeptide of Example 8-(3) as a test sample, the antigenicity for C179 was examined by the ELISA method. Namely, a diluted solution of the stem region polypeptide was added to a microtiter plate (Maxi Sorp; manufactured by Nunc) and immobilized at 37° C. for 90 minutes. Then blocking was effected by using Block Ace (manufactured by Snow Brand Milk Products). Then these cells were continuously reacted with 2 antibodies [10 mg/ml C179 solution diluted 200-fold, and peroxidase-labeled goat anti-mouse immunoglobulin G solution (manufactured by Cappel) diluted 500-fold] each for 90 minutes and the cells thus treated were washed with PBS. Finally, the peroxidase reaction was effected by using 0.03% $H_2O_2$ and 1 mg/ml of o-phenylenediamine dihydrochloride in citric acid/phosphoric acid (pH 5.2). The amount of the antigen was calculated from the absorbance of the reaction mixture at 492 nm. As a standard, HA molecules described in Example 8-(1) were used. As the result of the ELISA method, it has been proved that this stem region polypeptide has an antigenicity comparable to that of HA molecules. The haemagglutination activity (HA value) of the stem region polypeptide was determined in the following manner. On a U-shaped 96-well microtiter plates (Falcon 3911: manufactured by Becton Dickinson Labware), the sample solution was diluted with PBS in two steps. Then the same amount of a 0.5% avian erythrocyte suspension was added thereto and the mixture was stirred well. After reacting at room temperature for 1 hour, agglutination of the erythrocytes was observed. The highest dilution ratio showing agglutination was taken as the HA value.

The HA value of the stem region polypeptide was less than 1/1000 of the HA value of HA molecules.

Thus it has been clarified that the stem region polypeptide prepared by the treatment with the protease has an antigenicity comparable to that of HA molecules and the haemagglutination activity originating in the globular head region has substantially disappeared.

This polypeptide can easily serve as an antigen determinant and the globular head region, which is liable to undergo antigen mutation, has been digested therefrom. Thus it is usable as a vaccine capable of specifically recognizing the stem region of the H1N1 and H2N2 subtypes and inducing an antibody neutralizing the virus.

EXAMPLE 9 preparation of antigen polypeptide:

(1) Preparation of HA molecules

Viral particles (40 mg) of A/Kitakyushu/159/93 prepared in Example 1 were suspended in 27 ml of 5 mM Tris-HCl (pH 8.0). After adding 3 ml of 20% NP-40, the mixture was maintained at 37° C. for 30 minutes. Then it was centrifuged and the supernatant was collected and filtered through a 0.8 μm filter unit (Millex PF: manufactured by Millipore). Subsequently the filtrate was loaded on an ion exchange membrane (memSep DEAE: manufactured by Millipore) and washed with the same buffer. Further, HA molecules were eluted with the same buffer containing 1M of NaCl.

(2) Treatment of HA molecule with proteinase

In an N-ethylmorpholine buffer solution (pH 7.5), the HA molecules (2.6 μg) prepared in the above Example 9-(1) were digested with 4-pmol portions of lysyl endopeptidase (manufactured by Wako Pure Chemical Industries, Ltd.), V8 protease (manufactured by Sigma Chemical Co.) and chymotrypsin (manufactured by Boehringer) at 37° C. for 1 hour.

The HA molecules (2.6 μg) prepared in the above Example 9-(1) were denatured by maintaining at 42° C. in the presence of 2M of urea for 1 hour. Next, these molecules were digested with 4-pmol portions of lysyl endopeptidase, V8 protease, chymotrypsin, subtilisin (manufactured by Boehringer), proteinase K (manufactured by Boehringer), pronase (manufactured by Boehringer) and thermolysin (manufactured by Boehringer) in a 50 mM tris hydrochloride buffer, solution (pH 7.6) at 37° C. for 12 hours and then dialyzed against PBS.

A portion of each digestion mixture was collected and the digested fragments were analyzed by the dot-blot method with the use of AI3C and SDS polyacrylamide gel electrophoresis.

As a result, it was found out that most of the HA molecules remained undigested when treated with each of these proteases in the absence of urea. The HA molecules, which had been denatured with urea, employed as a substrate were not digested with V8 protease, thermolysin and pronase. When lysyl endopeptidase, chymotrypsin and subtilisin were used, the digestion proceeded excessively and the antigenicity for AI3C completely disappeared. When proteinase K was used, on the other hand, it was confirmed that the HA molecules were digested and polypeptide fragments having an avidity for AI3C were formed.

(3) Preparation of stem region polypeptide

To the HA molecules (250 μg/1400 μl) prepared in Example 9-(1) were successively added 100 μl of 1M Tris-HCl (pH 7.6) and 500 μl of 8M urea and the resulting mixture was maintained at 42° C. for 1 hour. To this solution was added 2000 μl of an mobilized Proteinase K gel and maintained at 37° C. for 7 hours under shaking. After centrifuging, the reaction mixture thus obtained was dialyzed against PBS for 12 hours and thus the stem region polypeptide was obtained.

(4) Properties of stem region polypeptide

By using the stem region polypeptide of Example 9-(3) as a test sample, the antigenicity for AI3C was examined by the ELISA method. Namely, a diluted solution of the stem region polypeptide was added to microtiter plate (Maxi Sorp; manufactured by Nunc) and mobilized at 37° C. for 90 minutes. Then blocking was effected by using Block Ace (manufactured by Snow Brand Milk Products). Then these cells were continuously reacted with 2 antibodies [10 mg/ml AI3C solution diluted 200-fold, and peroxidase-labeled goat anti-mouse immunoglobulin G solution (manufactured by Cappel) diluted 500-fold] each for 90 minutes and the cells thus treated were washed with PBS. Finally, the peroxidase reaction was effected by using 0.03% $H_2O_2$ and 1 mg/ml of o-phenylenediamine dihydrochloride in citric acid/phosphoric acid (pH 5.2). The amount of the antigen was calculated from the absorbance of the reaction mixture at 492 am. As a standard, HA molecules described in Example 9-(1) were used. As the result of the ELISA method, it has been proved that this stem region polypeptide has an antigenicity comparable to that of HA molecules. The haemagglutination activity (HA value) of the stem region polypeptide was determined in the following manner. On a U-shaped 96-well microtiter plates (Falcon 3911: manufactured by Becton Dickinson Labware), the sample solution was diluted with PBS in two steps. Then the same amount of a 0.5% arian erythrocyte suspension was added thereto and the mixture was stirred well. After reacting at room temperature for 1 hour, agglutination of the erythrocytes was observed. The highest dilution ratio showing agglutination was taken as the HA value.

The HA value of the stem region polypeptide was less than 1/1000 of the HA value of HA molecules.

Thus it has been clarified that the stem region polypeptide prepared by the treatment with the protease has an antigenicity comparable to that of molecules and the haemagglutination activity originating in the globular head region has substantially disappeared.

This polypeptide can easily serve as an antigen determinant and the globular head region, which is liable to undergo antigen mutation, has been digested therefrom. Thus it is usable as a vaccine capable specifically recognizing the stem region of H3N2 subtype and inducing an antibody neutralizing the virus.

EXAMPLE 10

Preventive effect on influenza virus:

From *Escherichia coli* JM109/pENH2dH01 (FERM BP-4190), a plasmid pENH2dH01 having, integrated thereinto, a gene codes for a polypeptide lacking the globular head region of A/Okuda/57 (H1N1) HA molecule was prepared.

Trypsin treated CV-1 cells ($5 \times 10^6$ cells) were washed with 20 ml 10% FCS-MEM in one time, and 20 ml PBS in two times, and suspended in 1 ml PBS. The 0.8 ml part of it and the plasmid pENH3dH01 (30 mg) were put into a cuvette for Genepulser™, and the cuvette was set into Genepulser™. The cells and plasmid were treated in 250 V, 960 mFD by Genepulser™. After the sample was put at 0° C. for 10 minutes, the cells were suspended in 60 ml 10% FCS-MEM and 5 ml each was cultured in a dish (6 cm).

On the third day of the incubation, the expression of the polypeptide was confirmed by a staining test with the use of C179. Cells in which the polypeptide had been expressed were treated with PBS containing trypsin and then harvested by centrifugation. The cells thus harvested were suspended in PBS and intraperitoneally administered to 10 female BALB/c mice aged 4 weeks as a vaccine in a dose of $1 \times 10^5$/animal. Two weeks thereafter, the second immunization was carried out in the same manner. As a control, CV-1 cells which had not been transformed by pENH2dH01 were used. These control cells were also intraperitoneally administered twice to 10 mice in a dose of $1 \times 10^5$ cells/animal. One week after the final immunization, 25 µl ($8 \times 10^4$ FFU) of A1/FM/1/47 (H1N1) was intranasally administered to the mice. Subsequently, the life or death of the animals was checked everyday.

Figure 4:
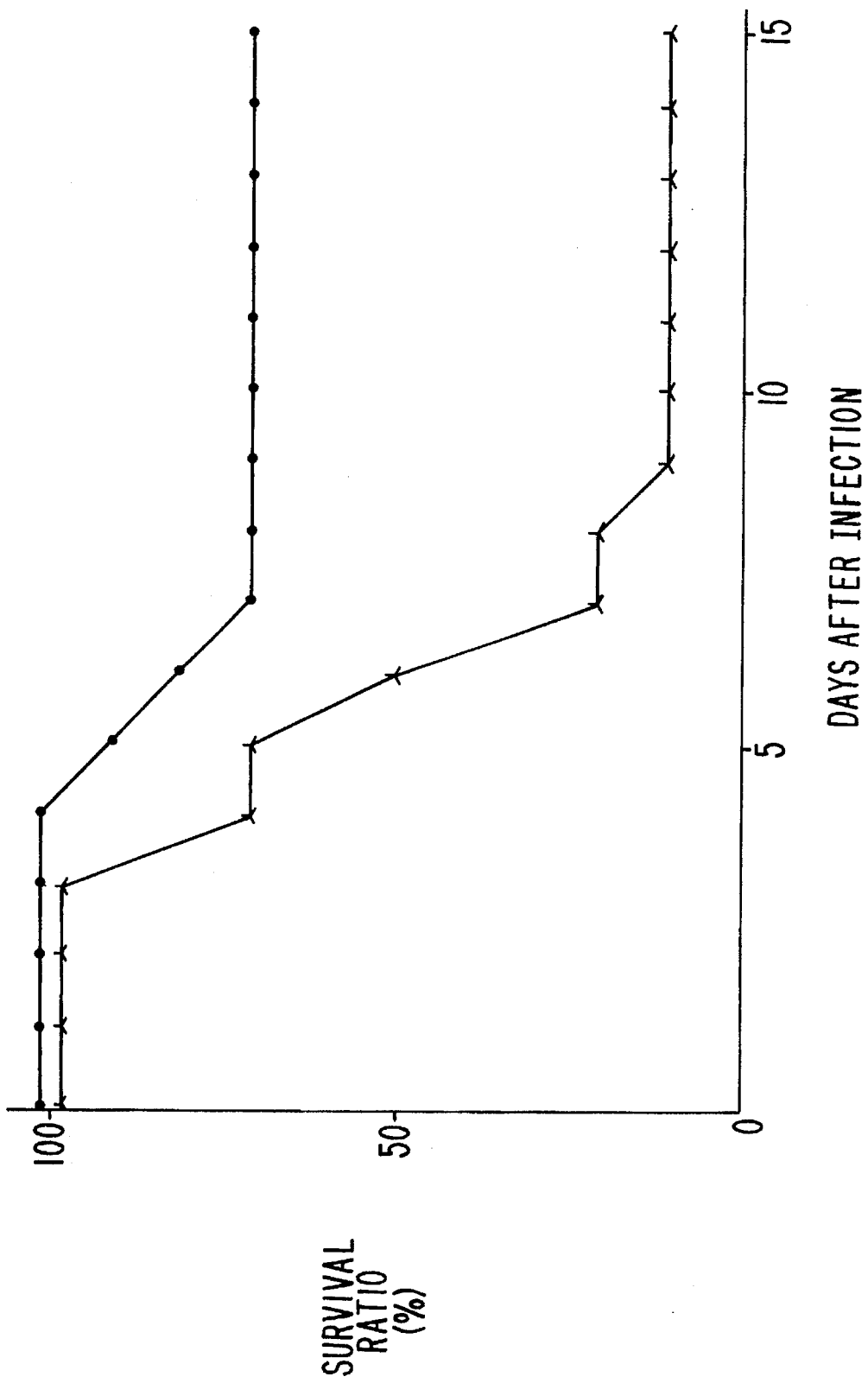
FIG. 4 is a graph showing the survival ratio of a group infected with influenza virus.

FIG. 4 shows the results. As FIG. 4 shows, 7 mice among 10 of the test group (black circle) immunized with the CV-1 cells with the expression of the antigen polypeptide survived 15 days after the inoculation of the highly toxic strain A1/FM/1/47. In contrast, 9 mice among 10 of the control group (black triangle) died.

FIG. 4 shows the survival ratios of the test (antigen polypeptide-administered) group and the control group wherein the ordinate refers to the survival ratio while the abscissa refers to the time (days) after the infection with the virus.

Thus it has been clarified that the antigen polypeptide lacking the globular head region of HA molecules can serve as a vaccine for the virus of the H1N1 subtype, though it per se origins in the H2N2 subtype.

This polypeptide can easily serve as an antigen determinant and the globular head region, which is liable to undergo antigen mutation, has been digested therefrom. Thus it is usable as a vaccine capable of specifically recognizing the stem region of the H1N1 and H2N2 subtypes and inducing an antibody neutralizing the virus.

EXAMPLE 11

Preventive effect on influenza virus:

By using the stem polypeptide described in the Example 8 as a test sample, the preventive effect on the infection with influenza virus was examined. The stem region polypeptide was suspended in PBS and intraperitoneally administered to female Balb/c mice aged 4 weeks in a dose of 10 µg/0.5 ml/animal. The animals were immunized thrice in total by repeating the intraperitoneal administration in the same does at intervals of 1 week. To a control group, PBS alone was administered. Ten days after the final immunization, the animals were intranasally inoculated with 25 µl ($2.0 \times 10^3$ FFU) per animal of A1/FM/1/47 (H1N1) virus. Then the life and death of the animals were observed and changes in the body weight of surviving mice were monitored.

Figure 5:
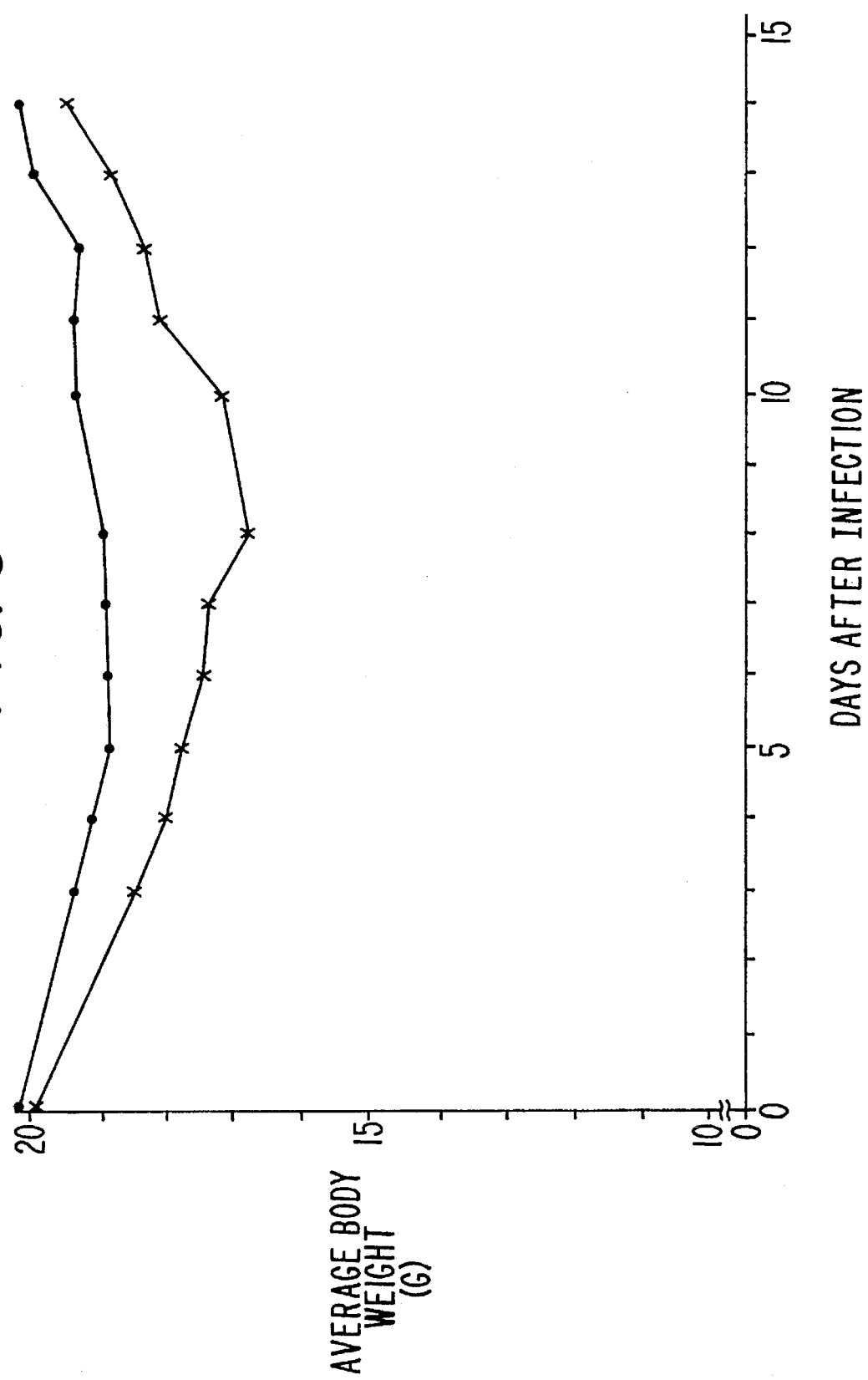
FIG. 5 is a graph showing the average body weight loss of a group infected with influenza virus.

As FIG. 5 shows the average body weight loss of the mice immunized with the stem region polypeptide was significantly lower than that of the control group. As FIG. 6 shows, further, 5 mice among 11 in the control group died within 7 days after the inoculation with the virus, while 8 mice among 10 immunized with the stem region polypeptide survived for 14 days after the inoculation, thus showing a survival ratio 14 days after the inoculation with the virus of 80%.

On the other hand, the survival ratio of the control group 14 days after the inoculation was 55%.

FIG. 5 is a graph showing the body weight changes of the stem region polypeptide-administered group and the control group wherein the ordinate indicates the average body weight of the surviving mice of each group while the abscissa indicates the time (days) after the inoculation with the virus. FIG. 6 is a graph showing the survival ratios of the stem region polypeptide-administered group and the control group wherein the ordinate indicates the survival ratio of each group while the abscissa indicates the time (days) after the inoculation with the virus.

Thus it has been clarified that the antigen polypeptide lacking the globular head region of HA molecules can serve as a vaccine for the influenza virus.

In conclusion, the present invention provides an antibody which is useful in the diagnosis, prevention and treatment of infection with human influenza A virus. The antigen site recognized by this antibody is conserved widely in virus subtypes and capable of inducing a neutralization antibody. Thus a polypeptide containing this site is valuable as a vaccine.

The present invention provides an immunogenic polypeptide capable of producing an antibody, which binds specifically to the stem region in HA molecule of the subtypes of human influenza A virus, and a gene coding for this polypeptide.

Especially, the polypeptide lacking the globular head region of HA molecule can be provided for a huge amount by gene recombination technology and it is very useful for the vaccine prevent from influenza virus because this polypeptide has no control under the antigenic mutation of the globular head region of HA molecule.

We claim:

1. An anti-human influenza virus antibody having the following characteristics:
    (a) specifically binds to the stem region of hemagglutinin of human influenza A virus subtypes H1N1 and H2N2;
    (b) does not specifically bind to the stem region of hemagglutinin of human influenza A virus subtype H3N2;
    (c) has a neutralization activity for human influenza A virus subtypes H1N1 and H2N2; and
    (d) has no neutralization activity for human influenza A virus subtype H3N2.

2. The antibody according to claim 1, having the following characteristics:
    (e) inhibits the membrane fusion activity of human influenza A virus subtypes H1N1 and H2N2; and
    (f) does not inhibit the membrane fusion activity of human influenza A virus subtype H3N2.

3. The antibody according to claim 1, which has the following characteristic:
    (g) does not inhibit the hemagglutination activity of human influenza A virus subtype H1N1, H2N2 or H3N2.

4. The antibody according to claim 1, which is a polyclonal antibody.

5. The antibody according to claim 1, which is a monoclonal antibody.

6. The antibody according to claim 1, which is a chimeric antibody.

7. The antibody according to claim 1, having the following characteristics:
    (h) specifically binds to an epitope defined by the amino acid sequences shown in SEQ ID No. 1 and SEQ ID No. 2;
    (i) does not specifically bind to an epitope defined by the amino acid sequences shown in SEQ ID No. 3 and SEQ ID No. 4.

8. The antibody according to claim 5, which is produced by the hybridoma bearing accession no. FERM BP-4517.

9. A composition comprising the antibody according to claim 1 together with a pharmaceutically acceptable carrier.

10. The hybridoma deposited as FERM BP-4517.

* * * * *

SEQUENCE LISTING ( 1 ) GENERAL INFORMATION:

( i i i ) NUMBER OF SEQUENCES: 58

( 2 ) INFORMATION FOR SEQ ID NO:1:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL:

( i v ) ANTI-SENSE:

( v ) FRAGMENT TYPE: internal fragment ( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:1:

Thr  Gly  Leu  Arg  Asn
1                     5

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:2:

```
Gly Ile Thr Asn Lys Val Asn Ser Val Ile Glu Lys
 1               5                  10
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:

(B) STRAIN:
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (A) LIBRARY:
                    (B) CLONE:

(viii) POSITION IN GENOME:
                    (A) CHROMOSOME/SEGMENT:
                    (B) MAP POSITION:
                    (C) UNITS:

(ix) FEATURE:
                    (A) NAME/KEY:
                    (B) LOCATION:
                    (C) IDENTIFICATION METHOD:
                    (D) OTHER INFORMATION:

(x) PUBLICATION INFORMATION:
                    (A) AUTHORS:
                    (B) TITLE:
                    (C) JOURNAL:
                    (D) VOLUME:
                    (E) ISSUE:
                    (F) PAGES:
                    (G) DATE:
                    (H) DOCUMENT NUMBER:
                    (I) FILING DATE:
                    (J) PUBLICATION DATE:
                    (K) RELEVANT RESIDUES IN SEQ ID NO:

(xi) SEQUENCE DESCRIPTION: SEQ ID NO:3:

Thr  Gly  Met  Arg  Asn
 1                    5

(2) INFORMATION FOR SEQ ID NO:4:

(i) SEQUENCE CHARACTERISTICS:
                    (A) LENGTH: 12 amino acids
                    (B) TYPE: amino acid
                    (C) STRANDEDNESS: single
                    (D) TOPOLOGY: linear (ii) MOLECULE TYPE: peptide (iii) HYPOTHETICAL:

(iv) ANTI-SENSE:

(v) FRAGMENT TYPE: internal fragment (vi) ORIGINAL SOURCE:
                    (A) ORGANISM:
                    (B) STRAIN:
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (A) LIBRARY:
                    (B) CLONE:

(viii) POSITION IN GENOME:
                    (A) CHROMOSOME/SEGMENT:
                    (B) MAP POSITION:
                    (C) UNITS:

(ix) FEATURE:

( A ) NAME/KEY:
                    ( B ) LOCATION: 9
                    ( C ) IDENTIFICATION METHOD:
                    ( D ) OTHER INFORMATION: /note= "Val or Leu"

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:4:

Gln  Ile  Asn  Gly  Lys  Leu  Asn  Arg  Xaa  Ile  Glu  Lys
1                  5                           10

( 2 ) INFORMATION FOR SEQ ID NO:5:

( i ) SEQUENCE CHARACTERISTICS:
                    ( A ) LENGTH: 19 bases
                    ( B ) TYPE: nucleic acid
                    ( C ) STRANDEDNESS: single
                    ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:5:

AGCAAAAGCA GGGGATAAT                                                                                                   19

( 2 ) INFORMATION FOR SEQ ID NO:6:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:6:

AGTAGAAACA AGGGTGTTTT T                                                                                                21

( 2 ) INFORMATION FOR SEQ ID NO:7:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

```
            ( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:7:

TCTTTTCGAG  TACTGTGTCA  ACA                                                      2 3

( 2 ) INFORMATION FOR SEQ ID NO:8:

( i ) SEQUENCE CHARACTERISTICS:
                    ( A ) LENGTH: 23 bases
                    ( B ) TYPE: nucleic acid
                    ( C ) STRANDEDNESS: single
                    ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:
```

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:8:

GCCCCACTAC AATTGGGGAA ATG                              23

(2) INFORMATION FOR SEQ ID NO:9:

(i) SEQUENCE CHARACTERISTICS:
    (A) LENGTH: 24 bases
    (B) TYPE: nucleic acid
    (C) STRANDEDNESS: single
    (D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:9:

TTTTACAGAA ATTTGCTATG GCTG 24

( 2 ) INFORMATION FOR SEQ ID NO:10:

( i ) SEQUENCE CHARACTERISTICS:
           ( A ) LENGTH: 24 bases
           ( B ) TYPE: nucleic acid
           ( C ) STRANDEDNESS: single
           ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
           ( A ) ORGANISM:
           ( B ) STRAIN:
           ( C ) INDIVIDUAL ISOLATE:
           ( D ) DEVELOPMENTAL STAGE:
           ( E ) HAPLOTYPE:
           ( F ) TISSUE TYPE:
           ( G ) CELL TYPE:
           ( H ) CELL LINE:
           ( I ) ORGANELLE:

( v i i ) IMMEDIATE SOURCE:
           ( A ) LIBRARY:
           ( B ) CLONE:

( v i i i ) POSITION IN GENOME:
           ( A ) CHROMOSOME/SEGMENT:
           ( B ) MAP POSITION:
           ( C ) UNITS:

( i x ) FEATURE:
           ( A ) NAME/KEY:
           ( B ) LOCATION:
           ( C ) IDENTIFICATION METHOD:
           ( D ) OTHER INFORMATION:

( x ) PUBLICATION INFORMATION:
           ( A ) AUTHORS:
           ( B ) TITLE:
           ( C ) JOURNAL:
           ( D ) VOLUME:
           ( E ) ISSUE:
           ( F ) PAGES:
           ( G ) DATE:
           ( H ) DOCUMENT NUMBER:
           ( I ) FILING DATE:
           ( J ) PUBLICATION DATE:
           ( K ) RELEVANT RESIDUES IN SEQ ID NO:

( x i ) SEQUENCE DESCRIPTION: SEQ ID NO:10:

ACTCCCCTAT TGTGACTGGG TGTA 24

( 2 ) INFORMATION FOR SEQ ID NO:11:

( i ) SEQUENCE CHARACTERISTICS:
           ( A ) LENGTH: 22 bases
           ( B ) TYPE: nucleic acid
           ( C ) STRANDEDNESS: single
           ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:11:

GGTTATCATC ATCAGAATGA AC                                                                22

(2) INFORMATION FOR SEQ ID NO:12:

(i) SEQUENCE CHARACTERISTICS:
                (A) LENGTH: 24 bases
                (B) TYPE: nucleic acid
                (C) STRANDEDNESS: single
                (D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

( i x ) FEATURE:
          ( A ) NAME/KEY:
          ( B ) LOCATION:
          ( C ) IDENTIFICATION METHOD:
          ( D ) OTHER INFORMATION:

( x ) PUBLICATION INFORMATION:
          ( A ) AUTHORS:
          ( B ) TITLE:
          ( C ) JOURNAL:
          ( D ) VOLUME:
          ( E ) ISSUE:
          ( F ) PAGES:
          ( G ) DATE:
          ( H ) DOCUMENT NUMBER:
          ( I ) FILING DATE:
          ( J ) PUBLICATION DATE:
          ( K ) RELEVANT RESIDUES IN SEQ ID NO:

( x i ) SEQUENCE DESCRIPTION: SEQ ID NO:12:

AGTTCACCTT GTTTGTAATC CCGT                    24

( 2 ) INFORMATION FOR SEQ ID NO:13:

( i ) SEQUENCE CHARACTERISTICS:
               ( A ) LENGTH: 24 bases
               ( B ) TYPE: nucleic acid
               ( C ) STRANDEDNESS: single
               ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
               ( A ) ORGANISM:
               ( B ) STRAIN:
               ( C ) INDIVIDUAL ISOLATE:
               ( D ) DEVELOPMENTAL STAGE:
               ( E ) HAPLOTYPE:
               ( F ) TISSUE TYPE:
               ( G ) CELL TYPE:
               ( H ) CELL LINE:
               ( I ) ORGANELLE:

( v i i ) IMMEDIATE SOURCE:
               ( A ) LIBRARY:
               ( B ) CLONE:

( v i i i ) POSITION IN GENOME:
               ( A ) CHROMOSOME/SEGMENT:
               ( B ) MAP POSITION:
               ( C ) UNITS:

( i x ) FEATURE:
               ( A ) NAME/KEY:
               ( B ) LOCATION:
               ( C ) IDENTIFICATION METHOD:
               ( D ) OTHER INFORMATION:

( x ) PUBLICATION INFORMATION:
               ( A ) AUTHORS:
               ( B ) TITLE:
               ( C ) JOURNAL:
               ( D ) VOLUME:
               ( E ) ISSUE:
               ( F ) PAGES:
               ( G ) DATE:
               ( H ) DOCUMENT NUMBER:
               ( I ) FILING DATE:
               ( J ) PUBLICATION DATE:
               ( K ) RELEVANT RESIDUES IN SEQ ID NO:

( x i ) SEQUENCE DESCRIPTION: SEQ ID NO:13:

```
CCATTTTTTA CTCTTTCCAT GCAT                                                    24
```

( 2 ) INFORMATION FOR SEQ ID NO:14:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:14:

```
ATCTACTCAA CTGTCGCCAG TTCA                                                    24
```

( 2 ) INFORMATION FOR SEQ ID NO:15:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:15:

TTGTGTCGAC CTTCTCTGTG GAA    23

( 2 ) INFORMATION FOR SEQ ID NO:16:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

- ( i x ) FEATURE:
    - ( A ) NAME/KEY:
    - ( B ) LOCATION:
    - ( C ) IDENTIFICATION METHOD:
    - ( D ) OTHER INFORMATION:

- ( x ) PUBLICATION INFORMATION:
    - ( A ) AUTHORS:
    - ( B ) TITLE:
    - ( C ) JOURNAL:
    - ( D ) VOLUME:
    - ( E ) ISSUE:
    - ( F ) PAGES:
    - ( G ) DATE:
    - ( H ) DOCUMENT NUMBER:
    - ( I ) FILING DATE:
    - ( J ) PUBLICATION DATE:
    - ( K ) RELEVANT RESIDUES IN SEQ ID NO:

- ( x i ) SEQUENCE DESCRIPTION: SEQ ID NO:16:

TGTAGCATTG CCGGATGGCT                                    20

( 2 ) INFORMATION FOR SEQ ID NO:17:

- ( i ) SEQUENCE CHARACTERISTICS:
    - ( A ) LENGTH: 23 bases
    - ( B ) TYPE: nucleic acid
    - ( C ) STRANDEDNESS: single
    - ( D ) TOPOLOGY: linear

- ( i i ) MOLECULE TYPE: other nucleic acid (synthetic DNA)

- ( i i i ) HYPOTHETICAL:

- ( i v ) ANTI-SENSE:

- ( v ) FRAGMENT TYPE:

- ( v i ) ORIGINAL SOURCE:
    - ( A ) ORGANISM:
    - ( B ) STRAIN:
    - ( C ) INDIVIDUAL ISOLATE:
    - ( D ) DEVELOPMENTAL STAGE:
    - ( E ) HAPLOTYPE:
    - ( F ) TISSUE TYPE:
    - ( G ) CELL TYPE:
    - ( H ) CELL LINE:
    - ( I ) ORGANELLE:

- ( v i i ) IMMEDIATE SOURCE:
    - ( A ) LIBRARY:
    - ( B ) CLONE:

- ( v i i i ) POSITION IN GENOME:
    - ( A ) CHROMOSOME/SEGMENT:
    - ( B ) MAP POSITION:
    - ( C ) UNITS:

- ( i x ) FEATURE:
    - ( A ) NAME/KEY:
    - ( B ) LOCATION:
    - ( C ) IDENTIFICATION METHOD:
    - ( D ) OTHER INFORMATION:

- ( x ) PUBLICATION INFORMATION:
    - ( A ) AUTHORS:
    - ( B ) TITLE:
    - ( C ) JOURNAL:
    - ( D ) VOLUME:
    - ( E ) ISSUE:
    - ( F ) PAGES:
    - ( G ) DATE:
    - ( H ) DOCUMENT NUMBER:
    - ( I ) FILING DATE:
    - ( J ) PUBLICATION DATE:
    - ( K ) RELEVANT RESIDUES IN SEQ ID NO:

- ( x i ) SEQUENCE DESCRIPTION: SEQ ID NO:17:

ATTATCCGGT TGCCAAAGGA TCG                                                                                                23

( 2 ) INFORMATION FOR SEQ ID NO:18:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:18:

GAGAGCACTG GTAATCTGTT GCA                                                                                                23

( 2 ) INFORMATION FOR SEQ ID NO:19:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

(v i) ORIGINAL SOURCE:
  (A) ORGANISM:
  (B) STRAIN:
  (C) INDIVIDUAL ISOLATE:
  (D) DEVELOPMENTAL STAGE:
  (E) HAPLOTYPE:
  (F) TISSUE TYPE:
  (G) CELL TYPE:
  (H) CELL LINE:
  (I) ORGANELLE:

(v i i) IMMEDIATE SOURCE:
  (A) LIBRARY:
  (B) CLONE:

(v i i i) POSITION IN GENOME:
  (A) CHROMOSOME/SEGMENT:
  (B) MAP POSITION:
  (C) UNITS:

(i x) FEATURE:
  (A) NAME/KEY:
  (B) LOCATION:
  (C) IDENTIFICATION METHOD:
  (D) OTHER INFORMATION:

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO:

(x i) SEQUENCE DESCRIPTION: SEQ ID NO:19:

CCATCAAATG CCTTTTGAGT GGA                                                    23

(2) INFORMATION FOR SEQ ID NO:20:

(i) SEQUENCE CHARACTERISTICS:
    (A) LENGTH: 23 bases
    (B) TYPE: nucleic acid
    (C) STRANDEDNESS: single
    (D) TOPOLOGY: linear (i i) MOLECULE TYPE: other nucleic acid (synthetic DNA)

(i i i) HYPOTHETICAL:

(i v) ANTI-SENSE:

(v) FRAGMENT TYPE:

(v i) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(v i i) IMMEDIATE SOURCE:
    (A) LIBRARY:
    (B) CLONE:

(v i i i) POSITION IN GENOME:
    (A) CHROMOSOME/SEGMENT:
    (B) MAP POSITION:
    (C) UNITS:

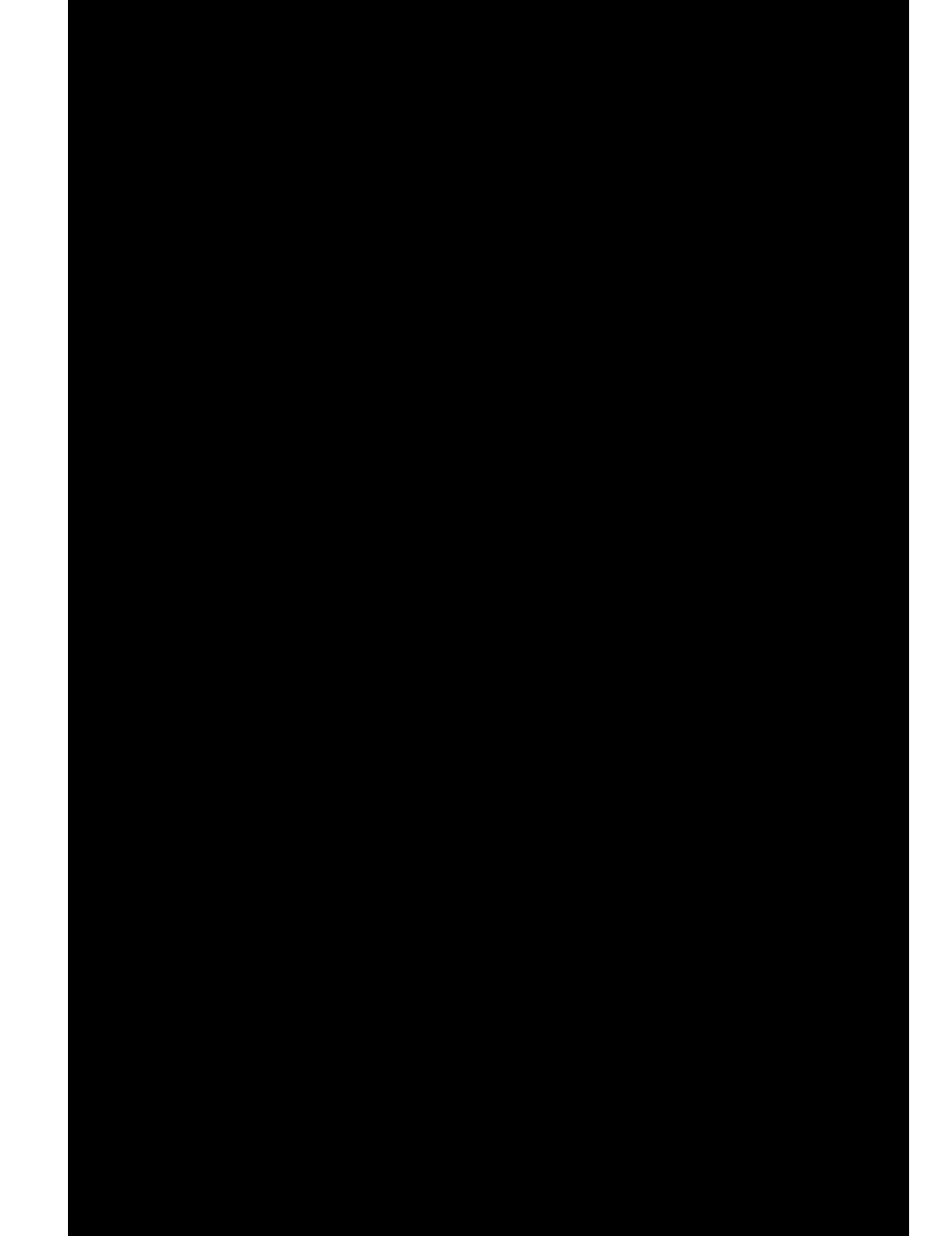

CATGCATTCA TCATCACATT TGTG 24

( 2 ) INFORMATION FOR SEQ ID NO:22:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:22:

CATACTTGGG ATAATCATAC GTC 23

( 2 ) INFORMATION FOR SEQ ID NO:23:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

(v i) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(v i i) IMMEDIATE SOURCE:
    (A) LIBRARY:
    (B) CLONE:

(v i i i) POSITION IN GENOME:
    (A) CHROMOSOME/SEGMENT:
    (B) MAP POSITION:
    (C) UNITS:

(i x) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(x i) SEQUENCE DESCRIPTION: SEQ ID NO:23:

GCCATTTATG CTACAGTAGC AGG    23

(2) INFORMATION FOR SEQ ID NO:24:

(i) SEQUENCE CHARACTERISTICS:
        (A) LENGTH: 24 bases
        (B) TYPE: nucleic acid
        (C) STRANDEDNESS: single
        (D) TOPOLOGY: linear (i i) MOLECULE TYPE: other nucleic acid (synthetic DNA)

(i i i) HYPOTHETICAL:

(i v) ANTI-SENSE:

(v) FRAGMENT TYPE:

(v i) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(v i i) IMMEDIATE SOURCE:
        (A) LIBRARY:
        (B) CLONE:

(v i i i) POSITION IN GENOME:
        (A) CHROMOSOME/SEGMENT:
        (B) MAP POSITION:
        (C) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:24:

GATCAGATTG AAGTGACTAA TGCT       24

( 2 ) INFORMATION FOR SEQ ID NO:25:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:25:

GAATGCATCA CTCCAAATGG AAGC                                                                                              24

(2) INFORMATION FOR SEQ ID NO:26:

(i) SEQUENCE CHARACTERISTICS:
           (A) LENGTH: 23 bases
           (B) TYPE: nucleic acid
           (C) STRANDEDNESS: single
           (D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
           (A) ORGANISM:
           (B) STRAIN:
           (C) INDIVIDUAL ISOLATE:
           (D) DEVELOPMENTAL STAGE:
           (E) HAPLOTYPE:
           (F) TISSUE TYPE:
           (G) CELL TYPE:
           (H) CELL LINE:
           (I) ORGANELLE:

(vii) IMMEDIATE SOURCE:
           (A) LIBRARY:
           (B) CLONE:

(viii) POSITION IN GENOME:
           (A) CHROMOSOME/SEGMENT:
           (B) MAP POSITION:
           (C) UNITS:

(ix) FEATURE:
           (A) NAME/KEY:
           (B) LOCATION:
           (C) IDENTIFICATION METHOD:
           (D) OTHER INFORMATION:

(x) PUBLICATION INFORMATION:
           (A) AUTHORS:
           (B) TITLE:
           (C) JOURNAL:
           (D) VOLUME:
           (E) ISSUE:
           (F) PAGES:
           (G) DATE:
           (H) DOCUMENT NUMBER:
           (I) FILING DATE:
           (J) PUBLICATION DATE:
           (K) RELEVANT RESIDUES IN SEQ ID NO:

(xi) SEQUENCE DESCRIPTION: SEQ ID NO:26:

AGGTCCTGAA TTCTCCCTTC TAC                                                                                              23

(2) INFORMATION FOR SEQ ID NO:27:

(i) SEQUENCE CHARACTERISTICS:
           (A) LENGTH: 1754 base pairs
           (B) TYPE: nucleic acid
           (C) STRANDEDNESS: double
           (D) TOPOLOGY: linear (ii) MOLECULE TYPE: cDNA to genomic RNA (iii) HYPOTHETICAL:

(iv) ANTI-SENSE:

(v) FRAGMENT TYPE:

(  v i  ) ORIGINAL SOURCE:
    ( A ) ORGANISM: A/Suita/1/89
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:27:

| | | | | | | |
|---|---|---|---|---|---|---|
| GGATAATAAA | TACAACCAAA | ATGAAAGCAA | AACTACTAGT | CCTGTTATGT | GCATTTACAG | 60 |
| CTACAGATGC | AGACACAATA | TGTATAGGCT | ACCATGCGAA | CAACTCAACC | GACACTGTTG | 120 |
| ACACAGTACT | TGAGAAGAAC | GTGACAGTGA | CACACTCTGT | CAACCTACTT | GAGGACAGTC | 180 |
| ACAACGGAAA | ACTATGTCGA | CTAAAAGGAA | TAGCCCCACT | ACAATTGGGT | AATTGCAGCA | 240 |
| TTGCCGGATG | GATCTTAGGA | AACCCAGAAT | GCGAATCACT | GTTTTCTAAG | GAATCATGGT | 300 |
| CCTACATTGC | AGAAACACCA | AACTCCGAGA | ATGGAACATG | TTACCCAGGG | TATTTCGCCG | 360 |
| ACTATGAGGA | ACTGAGGGAG | CAATTGAGTT | CAGTATCATC | ATTCGAGAGA | TTCGAAATAT | 420 |
| TCCCCAAAGA | AAGCTCATGG | CCCAACCACA | CCGTAACCAA | AGGAGTAACG | GCATCATGCT | 480 |
| CCCATAATGG | GAAAAGCAGT | TTTTACAGAA | ATTTGCTATG | GCTGACGGGG | AAGAATGGCT | 540 |
| TGTACCCAAA | TCTGAGCAAG | TCCTATGTGA | ACAACAAAGA | GAAAGAAGTC | CTTGTACTAT | 600 |
| GGGGTGTTCA | TCACCCGTCT | AACATAGGGG | ACCAAAGGGC | CATCTATCAT | ACAGAAAATG | 660 |
| CTTATGTCTC | TGTAGTGTCT | TCACATTATA | GCAGGAGATT | CACCCCAGAA | ATAGCAAAAA | 720 |
| GACCCAAAGT | AAGAGGTCAA | GAAGGAAGAA | TTAACTACTA | CTGGACTCTG | CTGGAACCCG | 780 |
| GGGACACAAT | AATATTTGAG | GCAAATGGAA | ATCTAATAGC | GCCATGGTAT | GCTTTCGCAC | 840 |
| TGAGTAGAGG | CTTTGGGTCA | GGAATCATCA | CCTCAAACGC | ATCAATGGAT | GAATGTGACG | 900 |
| CGAAGTGTCA | AACACCCCAG | GGAGCTATAA | ACAGTAGTCT | TCCTTTCCAG | AATGTACACC | 960 |
| CAGTCACAAT | AGGAGAGTGT | CCAAAGTATG | TCAGGAGTAC | AAAATTAAGG | ATGGTTACAG | 1020 |
| GACTAAGGAA | CATCCCATCC | ATTCAATCCA | GAGGTTTGTT | TGGAGCCATT | GCCGGTTTCA | 1080 |
| TTGAAGGGGG | GTGGACTGGA | ATGATAGATG | GATGGTATGG | TTATCATCAT | CAGAATGAAC | 1140 |
| AAGGATCTGG | CTATGCTGCG | GATCAAAAAA | GCACACAAAA | TGCCATTAAC | GGAATTACAA | 1200 |

```
ACAAGGTGAA  TTCTGTAATC  GAGAAAATGA  ACACTCAATT  CACAGCTGTG  GGCAAAGAAT    1260

TCAACAAATT  AGAAAGAAGG  ATGGAATACT  TAAATAAAAA  AGTTGATGAT  GGATTTCTGG    1320

ACATTTGGAC  ATATAATGCA  GAATTGTTGG  TTCTACTGGA  AAATGAAAGG  ACTTTGGATT    1380

TTCATGACTC  AAATGTGAAG  AATCTGTATG  AGAAAGTAAA  AAGCCAATTA  AAGAATAATG    1440

CCAAAGAAAT  AGGATACGGG  TGTTTTGAAT  TCTACCACAA  GTGTAACAAT  GAATGCATGG    1500

AAAGTGTGAA  AAATGGAACT  TATGACTATC  CAAAATATTC  CGAGGAATCA  AAGTTAAACA    1560

GGGAAAAAAT  TGATGGAGTG  AAATTGGAAT  CAATGGGAGT  CTATCAGATT  CTGGCGATCT    1620

ACTCAACTGT  CGCCAGTTCA  CTGGTGCTTT  TGGTCTCCCT  GGGGGCAATC  AGCTTCTGGA    1680

TGTGTTCTAA  TGGGTCTTTG  CAGTGTAGAA  TATGCATCTG  AGACCAGAAT  TTCAGAAATA    1740

TAAGAAAAAA  CACC                                                         1754
```

(2) INFORMATION FOR SEQ ID NO:28:

( i ) SEQUENCE CHARACTERISTICS:
        ( A ) LENGTH: 1728 base pairs
        ( B ) TYPE: nucleic acid
        ( C ) STRANDEDNESS: double
        ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
        ( A ) ORGANISM: A/Izumi/5/65
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:28:

```
ATAGACAACC  AAAAGCATAA  CAATGGCCAT  CATCTATCTC  ATACTCCTGT  TCACAGCAGT      60
```

-continued

| | | | | | | |
|---|---|---|---|---|---|---|
| GAGGGGGGAC | CAGATATGCA | TTGGATACCA | TGCCAATAAT | TCCACAGAAA | AGGTCGACAC | 120 |
| AATTCTAGAG | CGGAATGTCA | CTGTGACTCA | TGCCAAGGAC | ATCCTTGAGA | AGACCCACAA | 180 |
| CGGAAAGCTA | TGCAAACTAA | ACGGAATCCC | TCCACTTGAA | CTAGGGGACT | GTAGCATTGC | 240 |
| CGGATGGCTC | CTTGGAAATC | CAGAATGTGA | TAGGCTTCTA | AGGGTGCCAG | AATGGTCCTA | 300 |
| TATAATGGAG | AAAGAAAACC | CGAGATACAG | TTTATGTTAC | CCAGGCAACT | TCAATGACTA | 360 |
| TGAAGAATTG | AAACATCTCC | TCAGCAGCGT | AAAACATTTC | GAGAAAGTAA | AGATTCTGCC | 420 |
| CAAAGATAGA | TGGACACAGC | ATACAACAAC | TGGAGGTTCA | AAGGCCTGCG | CAGTGTCAGG | 480 |
| TAAACCATCA | TTCTTCAGGA | ACATGGTCTG | GCTGACAAAG | AAAGGACCAA | ATTATCCGGT | 540 |
| TGCCAAAGGA | TCGTACAACA | ATACGAGCGG | AGAGCAAATG | CTAATAATTT | GGGGAGTGCA | 600 |
| CCATCCTAAT | GATGAGGCAG | AACAAAGAGC | ATTGTACCAG | GAAGTGGGAA | CCTATGTTTC | 660 |
| CGCAAGCACA | TCAACATTGA | ACAAAAGGTC | AATCCCTGAA | ATAGCAGCAA | GGCCTAAAGT | 720 |
| GAATGGACTA | GGAAGTAGAA | TGGAATTCTC | TTGGACCCTC | TTGGATGTGT | GGGACACCAT | 780 |
| AAATTTTGAG | AGCACTGGTA | ATCTAGTTGC | ACCAGAGTAT | GGATTCAAAA | TATCGAAAAG | 840 |
| AGGTAGTTCA | GGGATCATGA | AGACAGAAGG | AACACTTGGG | AACTGTGAGA | CCAAATGCCA | 900 |
| AACTCCTTTG | GGAGCAATAA | ATACAACACT | ACCTTTTCAC | AATGTCCACC | CACTGACAAT | 960 |
| AGGTGAATGC | CCCAAATATG | TAAAATCGGA | GAAATTGGTC | TTAGCAACAG | GACTAAGGAA | 1020 |
| TGTTCCCCAG | ATTGAATCAA | GAGGATTGTT | TGGGGCAATA | GCTGGCTTTA | TAGAAGGAGG | 1080 |
| ATGGCAAGGA | ATGGTTGATG | GTTGGTATGG | ATACCATCAC | AGCAATGACC | AGGGATCAGG | 1140 |
| GTATGCAGCA | GACAAAGAAT | CCACTCAAAA | GGCATTTGAT | GGAATCACCA | ACAAGGTAAA | 1200 |
| TTCTGTGATT | GAAAAGATGA | ACACCCAATT | TGAAGCTGTT | GGGAAAGAAT | TCAATAATTT | 1260 |
| AGAGAAAAGA | CTGGAGAACT | TGAACAAAAA | GATGGAAGAC | GGGTTTCTAG | ATGTGTGGAC | 1320 |
| ATACAATGCT | GAGCTTCTAG | TTCTGATGGA | AAATGAGAGG | ACACTTGACT | TCCATGATTC | 1380 |
| TAATGTCAAG | AACCTGTATG | ATAAAGTCAG | AATGCAGCTG | AGAGACAACG | TCAAAGAACT | 1440 |
| AGGAAATGGA | TGTTTTGAAT | TTTATCACAA | ATGTGACGAT | GAATGCATGA | ATAGTGTGAA | 1500 |
| AAACGGGACG | TATGATTATC | CCAAGTATGA | AGAAGAATCT | AAACTAAATA | GAAATGAAAT | 1560 |
| CAAAGGGGTA | AAATTGAGCA | GCATGGGGGT | TTACCAAATT | CTTGCCATTT | ATGCTACAGT | 1620 |
| TGCAGGTTCT | CTGTCACTGG | CAATCATGAT | GGCTGGGATC | TCTTTCTGGA | TGTGCTCCAA | 1680 |
| CGGGTCTCTG | CAGTGCAGAA | TCTGCATATG | ATTGTAATTT | ATTTTATA | | 1728 |

( 2 ) INFORMATION FOR SEQ ID NO:29:

( i ) SEQUENCE CHARACTERISTICS:
        ( A ) LENGTH: 442 base pairs
        ( B ) TYPE: nucleic acid
        ( C ) STRANDEDNESS: double
        ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
        ( A ) ORGANISM: A/PR/8/34
        ( B ) STRAIN:
        ( C ) INDIVIDUAL ISOLATE:
        ( D ) DEVELOPMENTAL STAGE:
        ( E ) HAPLOTYPE:

(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:29:

```
CCTTTCCAGA ATATACACCC AGTCACAATA GGAGAGTGCC CAAAATACGT CAGGAGTGCC      60
AAATTGAGGA TGGTTACAGG ACTAAGGAAC ATCCCGTCCA TTCAATCCAG AGGTCTATTT     120
GGAGCCATTG CCGGTTTTAT TGAAGGGGGA TGGACTGGAA TGATAGATGG ATGGTATGGT     180
TATCATCATC AGAATGAACA GGGATCAGGC TATGCAGCGG ATCAAAAAG CACACAAAAT      240
GCCATTAACG GGATTACAAA CAAGGTGAAC TCTGTTATCG AGAAAATGAA CACTCAATTC     300
ACAGCTGTGG GTAAAGAATT CAACAAATTA GAAAAAGGA TGGAAAATTT AAATAAAAAA     360
GTTGATGATG GATTTCTGGA CATTTGGACA TATAATGCAG AATTGTTAGT TCTACTGGAA     420
AATGAAAGGA CTCTGGATTT CC                                             442
```

(2) INFORMATION FOR SEQ ID NO:30:

(i) SEQUENCE CHARACTERISTICS:
(A) LENGTH: 424 base pairs
(B) TYPE: nucleic acid
(C) STRANDEDNESS: double
(D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
(A) ORGANISM: A/Bangkok/10/83
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:30:

| | | | | | | |
|---|---|---|---|---|---|---|
| CCTTTCCAGA | ATGTACACCC | AGTCACAATA | GGAGAGTGCC | CAAAGTACGT | CAGGAGTACA | 60 |
| AAATTAAGGA | TGGTTACAGG | ACTAAGGAAC | ATCCCATCCA | TTCAATCCAG | AGGTTTGTTT | 120 |
| GGAGCCATTG | CCGGTTTCAT | TGAAGGGGGA | TGGACTGGAA | TGATAGATGG | ATGGTATCGT | 180 |
| TATCATCATC | AGAATGAACA | AGGATCTGGC | TATGCTGCGG | ATCAAAAAG | CACACAAAAT | 240 |
| GCCATTAACG | GGATTACAAA | CAAGGTGAAC | TCTGTAATCG | AGAAAATGAA | CACTCAATTC | 300 |
| ACAGCTGTGG | GTAAAGAATT | CAACAAATTA | GAAAAAAGGA | TGGAAAACTT | AAATAAAAAA | 360 |
| GTTGATGATG | GATTTCTGGA | CATTTGGACA | TATAATGCAG | AATTGTTGGT | TCTACTGGAA | 420 |
| AATG | | | | | | 424 |

(2) INFORMATION FOR SEQ ID NO:31:

(i) SEQUENCE CHARACTERISTICS:
(A) LENGTH: 424 base pairs
(B) TYPE: nucleic acid
(C) STRANDEDNESS: double
(D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
(A) ORGANISM: A/Yamagata/120/86
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:

( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:31:

| | | | | | | |
|---|---|---|---|---|---|---|
| CCTTTCCAGA | ATGTACACCC | AGTCACAATA | GGAGAGTGCC | CAAAGTATGT | CAGGAGTACA | 60 |
| AAATTAAGGA | TGGTTACAGG | ACTAAGGAAC | ATCCCATCCA | TTCAATCCAG | AGGTTTGTTT | 120 |
| GGAGCCATTG | CCGGTTTCAT | TGAAGGGGGG | TGGACTGGAA | TGATAGATGG | ATGGTATGGT | 180 |
| TATCATCATC | AGAATGAACA | AGGATCTGGC | TATGCTGCGG | ATCAAAAAAG | CACACAAAAT | 240 |
| GCCATTAACG | GGATTACAAA | CAAGGTGAAT | TCTGTAATCG | AGAAAATGAA | CACTCAATTC | 300 |
| ACAGCTGTGG | GCAAAGAATT | CAACAAATTA | GAAAGAAGGA | TGGAAAACTT | AAATAAAAAA | 360 |
| GTTGATGATG | GATTTCTGGA | CATTTGGACA | TATAATGCAG | AATTGTTGGT | CCTACTGGAA | 420 |
| AATG | | | | | | 424 |

( 2 ) INFORMATION FOR SEQ ID NO:32:

( i ) SEQUENCE CHARACTERISTICS:
        ( A ) LENGTH: 429 base pairs
        ( B ) TYPE: nucleic acid
        ( C ) STRANDEDNESS: double
        ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
        ( A ) ORGANISM: A/Osaka/930/88
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:

( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:32:

```
CCTTTCCAGA ATGTACACCC AGTCACAATA GGAGAGTGCC CAAAGTATGT CAGGAGTACA      60

AAATTAAGGA TGGTTACAGG ACTAAGGAAC ATCCCATCCA TTCAATCCAG AGGTTTGTTT     120

GGAGCCATTG CCGGTTTCAT AGAAGGGGGG TGGACTGGAA TGATAGATGG ATGGTATGGT     180

TATCATCATC AGAATGAACA AGGATCTGGC TATGCTGCGG ATCAAAAAG CACACAAAAT      240

GCCATTAACG GAATTACAAA CAAGGTGAAT TCTGTAATCG AGAAAATGAA CACTCAATTC     300

ACAGCTGTGG GCAAAGAATT CAACAAATTA GAAGAAGGA TGGAAAACTT AAATAAAAAA      360

GTTGATGATG GATTTCTGGA CATTTGGACA TATAATGCAG AATTGTTGGT TCTACTGGAA     420

AATGAAAGG                                                            429
```

( 2 ) INFORMATION FOR SEQ ID NO:33:

( i ) SEQUENCE CHARACTERISTICS:
        ( A ) LENGTH: 400 base pairs
        ( B ) TYPE: nucleic acid
        ( C ) STRANDEDNESS: double
        ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
        ( A ) ORGANISM: A/Okuda/57
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:

(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:33:

| | | | | | | |
|---|---|---|---|---|---|---|
| GCAATAAATA | CAACATTACC | TTTTCACAAT | GTCCACCCAC | TGACAATAGG | TGAGTGCCCC | 60 |
| AAATATGTAA | AATCGGAGAA | GTTGGTCTTA | GCAACAGGAC | TAAGGAATGT | TCCCCAGATT | 120 |
| GAATCAAGAG | GATTGTTTGG | GGCAATAGCT | GGTTTATAG | AAGGAGGATG | GCAAGGAATG | 180 |
| GTTGACGGTT | GGTATGGATA | CCATCACAGC | AATGACCAGG | GATCAGGGTA | TGCAGCAGAC | 240 |
| AAAGAATCCA | CTCAAAAGGC | ATTTGATGGA | ATCACCAACA | AGGTAAATTC | TGTGATTGAA | 300 |
| AAGATAAACA | CCCAATTTGA | AGCTGTTGGG | AAAGAATTCG | GTAACTTAGA | GAAAAGACTG | 360 |
| GAGAACTTGA | ACAAAAAGAT | GGAAGACGGG | TTTCTAGATG | | | 400 |

(2) INFORMATION FOR SEQ ID NO:34:

(i) SEQUENCE CHARACTERISTICS:
        (A) LENGTH: 409 base pairs
        (B) TYPE: nucleic acid
        (C) STRANDEDNESS: double
        (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
        (A) ORGANISM: A/Adachi/2/57
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

( x i ) SEQUENCE DESCRIPTION: SEQ ID NO:34:

| | | | | | | |
|---|---|---|---|---|---|---|
| CGCCTTGGAG | CAATAAATAC | AACATTGCCT | TTTCACAATG | TCCACCCACT | GACAATAGGT | 60 |
| GAGTGCCCCA | AATATGTAAA | ATCGGAGAAG | TTGGTCTTAG | CAACAGGACT | AAGGAATGTT | 120 |
| CCCCAGATTG | AATCAAGAGG | ATTGTTTGGG | GCAATAGCTG | GTTTTATAGA | AGGAGGATGG | 180 |
| CAAGGAATGG | TTGATGGTTG | GTATGGATAC | CATCACAGCA | ATGACCAGGG | ATCAGGGTAT | 240 |
| GCAGCAGACA | AAGAATCCAC | TCAAAAGGCA | TTTGATGGAA | TCACCAACAA | GGTAAATTCT | 300 |
| GTGATTGAAA | AGATGAACAC | CCAATTTGAA | GCTGTTGGGA | AAGAATTCGG | TAACTTAGAG | 360 |
| AGAAGACTGG | AGAACTTGAA | CAAAAGATG | GAAGACGGGT | TTCTAGATG | | 409 |

( 2 ) INFORMATION FOR SEQ ID NO:35:

( i ) SEQUENCE CHARACTERISTICS:
        ( A ) LENGTH: 410 base pairs
        ( B ) TYPE: nucleic acid
        ( C ) STRANDEDNESS: double
        ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
        ( A ) ORGANISM: A/Kumamoto/1/65
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:35:

| | | | | | | |
|---|---|---|---|---|---|---|
| CTCCTTTGGA | GCAATAAATA | CAACATTACC | TTTTCACAAT | GTCCACCCAC | TGACAATAGG | 60 |
| TGAATGCCCC | AAATATGTAA | AATCGGAGAA | ACTGGTCTTA | GCAACAGGAC | TAAGGAATGT | 120 |
| TCCCCAGATT | GAATCAAGAG | GATTGTTTGG | GGCAATAGCT | GGCTTTGTAG | AAGGAGGATG | 180 |

| | | | | | |
|---|---|---|---|---|---|
| GCAAGGAATG | ATTGATGGTT | GGTATGGATA | CCATCACAGC | AATGATCAGG | GATCAGGGTT | 240
| TGCAGCAGAC | AAAGAATCCA | CTCAAAAGGC | ATTTGATGGA | ATCACCAACA | AGGTAAATTC | 300
| TGTGATTGAA | AAGATGAACA | CCCAATTTGA | AGCTGTTGGG | AAAGAATTCA | ATAATTTAGA | 360
| GAAAAGACTG | GAGAACTTGA | ACAAAAGGAT | GGAAGACGGG | TTTCTAGATG | | 410

(2) INFORMATION FOR SEQ ID NO:36:

(i) SEQUENCE CHARACTERISTICS:
        (A) LENGTH: 394 base pairs
        (B) TYPE: nucleic acid
        (C) STRANDEDNESS: double
        (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
        (A) ORGANISM: A/Kaizuka/2/65
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:36:

| | | | | | |
|---|---|---|---|---|---|
| AATACAACAC | TACCTTTTCA | CAATGTCCAC | CCACTGACAA | TAGGTGAATG | CCCCAAATAT | 60
| GTAAAATCGG | AGAAATTGGT | CTTAGCAACA | GGACTAAGGA | ATGTTCCCCA | GATTGAATCA | 120
| AGAGGATTGT | TTGGGGCAAT | AGCTGGCTTT | ATAGAAGGAG | GATGGCAAGG | AATGGTTGAT | 180
| GGTTGGTATG | GATACCATCA | CAGCAATGAC | CAGGGATCAG | GGTATGCAGC | AGACAAAGAA | 240
| TCCACTCAAA | AGGCATTTGA | TGGAATCACC | AACAAGGTAA | ATTCTGTGAT | TGAAAAGATG | 300
| AACACCCAAT | TTGAAGCTGT | TGGGAAAGAA | TTCAATAATT | TAGAGAAAAG | ACTGGAGAAC | 360
| TTGAACAAAA | AGATGGAAGA | CGGGTTTCTA | GATG | | | 394

( 2 ) INFORMATION FOR SEQ ID NO:37:

( i ) SEQUENCE CHARACTERISTICS:
    ( A ) LENGTH: 329 base pairs
    ( B ) TYPE: nucleic acid
    ( C ) STRANDEDNESS: double
    ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
    ( A ) ORGANISM: A2/Aichi/2/68
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:37:

```
ATGACAAGCC CTTTCAAAAC GTAAACAAGA TCACATATGG AGCATGCCCC AAGTATGTTA    60

AGCAAAACAC CCTGAAGTTG GCAACAGGGA TGCGGAATGT ACCAGAGAAA CAAACTAGAG   120

GCCTATTCGG CGCAATAGCA GGTTTCATAG AAAATGGTTG GGAGGGAATG ATAGACGGTT   180

GGTACGGTTT CAGGCATCAA AATTCTGAGG GCACAGGACA AGCAGCAGAT CTTAAAAGCA   240

CTCAAGCAGC CATCGACCAA ATCAATGGGA AATTGAACAG GGTAATCGAG AAGACGAACG   300

AGAAATTCCA TCAAATCGAA AAGGAATTC                                    329
```

( 2 ) INFORMATION FOR SEQ ID NO:38:

( i ) SEQUENCE CHARACTERISTICS:
    ( A ) LENGTH: 334 base pairs
    ( B ) TYPE: nucleic acid
    ( C ) STRANDEDNESS: double
    ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
- ( A ) ORGANISM: A/Fukuoka/C29/85
- ( B ) STRAIN:
- ( C ) INDIVIDUAL ISOLATE:
- ( D ) DEVELOPMENTAL STAGE:
- ( E ) HAPLOTYPE:
- ( F ) TISSUE TYPE:
- ( G ) CELL TYPE:
- ( H ) CELL LINE:
- ( I ) ORGANELLE:

( v i i ) IMMEDIATE SOURCE:
- ( A ) LIBRARY:
- ( B ) CLONE:

( v i i i ) POSITION IN GENOME:
- ( A ) CHROMOSOME/SEGMENT:
- ( B ) MAP POSITION:
- ( C ) UNITS:

( i x ) FEATURE:
- ( A ) NAME/KEY:
- ( B ) LOCATION:
- ( C ) IDENTIFICATION METHOD:
- ( D ) OTHER INFORMATION:

( x ) PUBLICATION INFORMATION:
- ( A ) AUTHORS:
- ( B ) TITLE:
- ( C ) JOURNAL:
- ( D ) VOLUME:
- ( E ) ISSUE:
- ( F ) PAGES:
- ( G ) DATE:
- ( H ) DOCUMENT NUMBER:
- ( I ) FILING DATE:
- ( J ) PUBLICATION DATE:
- ( K ) RELEVANT RESIDUES IN SEQ ID NO:

( x i ) SEQUENCE DESCRIPTION: SEQ ID NO:38:

```
ATGACAAACC CTTTCAAAAT GTAAACAAGA TCACATATGG GGCATGTCCC AGGTATGTTA      60
AGCAAAACAC TCTGAAATTG GCAACAGGGA TGCGGAATGT ACCAGAGAAA CAAACTAGAG     120
GCATATTCGG CGCAATAGCA GGTTTCATAG AAAATGGTTG GGAGGGAATG GTAGACGGTT     180
GGTACGGTTT CAGGCATCAA AATTCTGAGG CACAGGACA AGCAGCAGAT CTTAAAAGCA      240
CTCAAGCAGC AATCGACCAA ATCAACGGGA AACTGAATAG GTTAATCGAG AAGACGAACG     300
AGAAATTCCA TCAAATCGAA AAGGAATTCT CAGA                                 334
```

( 2 ) INFORMATION FOR SEQ ID NO:39:

( i ) SEQUENCE CHARACTERISTICS:
- ( A ) LENGTH: 329 base pairs
- ( B ) TYPE: nucleic acid
- ( C ) STRANDEDNESS: double
- ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
- ( A ) ORGANISM: A/Sichuan/2/87

( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:39:

```
ATGACAAACC  CTTTCAAAAT  GTAAACAAGA  TCACATATGG  GGCATGTCCC  AGATATGTTA      60

AGCAAAACAC  TCTGAAATTG  GCAACAGGGA  TGCGGAATGT  ACCAGAGAAA  CAAACTAGAG     120

GCATATTCGG  CGCAATAGCA  GGTTTCATAG  AAAATGGTTG  GGAGGGAATG  GTAGACGGCT     180

GGTACGGTTT  CAGGCATCAA  AATTCTGAGG  GCACAGGACA  AGCAGCAGAT  CTTAAAAGCA     240

CTCAAGCAGC  AATCGACCAA  ATCAACGGGA  AACTGAATAG  GTTAATCGAG  AAGACGAACG     300

AGAAATTCCA  TCAAACCGAA  AAGGAATTC                                         329
```

( 2 ) INFORMATION FOR SEQ ID NO:40:

( i ) SEQUENCE CHARACTERISTICS:
          ( A ) LENGTH: 334 base pairs
          ( B ) TYPE: nucleic acid
          ( C ) STRANDEDNESS: double
          ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
          ( A ) ORGANISM: A/Ibaraki/1/90
          ( B ) STRAIN:
          ( C ) INDIVIDUAL ISOLATE:
          ( D ) DEVELOPMENTAL STAGE:
          ( E ) HAPLOTYPE:
          ( F ) TISSUE TYPE:
          ( G ) CELL TYPE:
          ( H ) CELL LINE:
          ( I ) ORGANELLE:

( v i i ) IMMEDIATE SOURCE:

(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:40:

| | | | | | |
|---|---|---|---|---|---|
| ATGACAAACC | CTTTCAAAAT | ATAAACAGGA | TCACATATGG | GGCATGTCCC | AGATATGTTA | 60
| AGCAAAACAC | TCTGAAATTG | GCAACAGGGA | TGCGGAATGT | ACCAGAGAAA | CAAACTAGAG | 120
| GCATATTCGG | CGCAATCGCA | GGTTTCATAG | AAAATGGTTG | GGAGGGAATG | GTAGACGGTT | 180
| GGTACGGTTT | CAGGCATCAA | AATTCTGAGG | GCACAGGACA | AGCAGCAGAT | CTTAAAAGCA | 240
| CTCAAGCAGC | AATCGACCAA | ATCAACGGGA | AACTGAATAG | GTTAATCGAG | AAGACGAACG | 300
| AGAAATTCCA | TCAAATCGAA | AAGGAATTCT | CAGA | | | 334

(2) INFORMATION FOR SEQ ID NO:41:

(i) SEQUENCE CHARACTERISTICS:
(A) LENGTH: 329 base pairs
(B) TYPE: nucleic acid
(C) STRANDEDNESS: double
(D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
(A) ORGANISM: A/Suita/1/90
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:

(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:41:

| | | | | | | |
|---|---|---|---|---|---|---|
| ATGACAAACC | CTTTCAAAAT | GTAAACAGGA | TCACATATGG | GGCATGTCCC | AGATATGTTA | 60 |
| AGCAAAACAC | TCTGAAATTG | GCAACAGGGA | TGCGGAATGT | ACCAGAAAAA | CAAACTAGGG | 120 |
| GCATATTCGG | CGCAATCGCA | GGTTTCATAG | AAAATGGTTG | GGAGGGAATG | GTAGACGGTT | 180 |
| GGTACGGTTT | CAGGCATCAA | AACTCTGAGG | GCACAGGACA | AGCAGCAGAT | CTTAAAAGCA | 240 |
| CTCAAGCAGC | AATCGACCAA | ATCAACGGGA | AACTGAATAG | GTTAATCGAG | AAGACGAACG | 300 |
| AGAAATTCCA | TCAAACCGAA | AAGGAATTC | | | | 329 |

(2) INFORMATION FOR SEQ ID NO:42:

(i) SEQUENCE CHARACTERISTICS:
(A) LENGTH: 30 bases
(B) TYPE: nucleic acid
(C) STRANDEDNESS: single
(D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:

( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:42:

GATCTAGAAG CAAAAGCAGG GGTTATACCA 30

( 2 ) INFORMATION FOR SEQ ID NO:43:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( v i i ) IMMEDIATE SOURCE:
( A ) LIBRARY:
( B ) CLONE:

( v i i i ) POSITION IN GENOME:
( A ) CHROMOSOME/SEGMENT:
( B ) MAP POSITION:
( C ) UNITS:

( i x ) FEATURE:
( A ) NAME/KEY:
( B ) LOCATION:
( C ) IDENTIFICATION METHOD:
( D ) OTHER INFORMATION:

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:43:

CGGCTAGCAA AAGCAGGGGT TATACCATAG 30

( 2 ) INFORMATION FOR SEQ ID NO:44:

( i ) SEQUENCE CHARACTERISTICS:
( A ) LENGTH: 29 bases
( B ) TYPE: nucleic acid
( C ) STRANDEDNESS: single
( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
   ( A ) ORGANISM:
   ( B ) STRAIN:
   ( C ) INDIVIDUAL ISOLATE:
   ( D ) DEVELOPMENTAL STAGE:
   ( E ) HAPLOTYPE:
   ( F ) TISSUE TYPE:
   ( G ) CELL TYPE:
   ( H ) CELL LINE:
   ( I ) ORGANELLE:

( v i i ) IMMEDIATE SOURCE:
   ( A ) LIBRARY:
   ( B ) CLONE:

( v i i i ) POSITION IN GENOME:
   ( A ) CHROMOSOME/SEGMENT:
   ( B ) MAP POSITION:
   ( C ) UNITS:

( i x ) FEATURE:
   ( A ) NAME/KEY:
   ( B ) LOCATION:
   ( C ) IDENTIFICATION METHOD:
   ( D ) OTHER INFORMATION:

( x ) PUBLICATION INFORMATION:
   ( A ) AUTHORS:
   ( B ) TITLE:
   ( C ) JOURNAL:
   ( D ) VOLUME:
   ( E ) ISSUE:
   ( F ) PAGES:
   ( G ) DATE:
   ( H ) DOCUMENT NUMBER:
   ( I ) FILING DATE:
   ( J ) PUBLICATION DATE:
   ( K ) RELEVANT RESIDUES IN SEQ ID NO:

( x i ) SEQUENCE DESCRIPTION: SEQ ID NO:44:

ACAGATCTAG TAGAAACAAG GGTGTTTTT   29

( 2 ) INFORMATION FOR SEQ ID NO:45:

( i ) SEQUENCE CHARACTERISTICS:
   ( A ) LENGTH: 30 bases
   ( B ) TYPE: nucleic acid
   ( C ) STRANDEDNESS: single
   ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
   ( A ) ORGANISM:
   ( B ) STRAIN:
   ( C ) INDIVIDUAL ISOLATE:
   ( D ) DEVELOPMENTAL STAGE:
   ( E ) HAPLOTYPE:
   ( F ) TISSUE TYPE:
   ( G ) CELL TYPE:
   ( H ) CELL LINE:
   ( I ) ORGANELLE:

( v i i ) IMMEDIATE SOURCE:

(A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:45:

CGGCTAGCAG AAACAAGGGT GTTTTTAATT                                30

(2) INFORMATION FOR SEQ ID NO:46:

(i) SEQUENCE CHARACTERISTICS:
                (A) LENGTH: 1783 base pairs
                (B) TYPE: nucleic acid
                (C) STRANDEDNESS: double
                (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
                (A) ORGANISM: A/Okuda/57
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:

(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:46:

| | | | | | | | | | | | | | | | |
|---|---|---|---|---|---|---|---|---|---|---|---|---|---|---|---|
| CGGCTAGCAA | | | AAGCAGGGGT | | | TATACCATAG | | | AAAACCAAAA | | | GCAAAACA | | | 48 |
| ATG | GCC | ATC | ATT | TAT | CTC | ATT | CTC | CTG | TTC | ACA | GCA | GTG | AGA | GGG | 93 |
| Met | Ala | Ile | Ile | Tyr | Leu | Ile | Leu | Leu | Phe | Thr | Ala | Val | Arg | Gly | |
| -15 | | | | -10 | | | | | -5 | | | | | | |
| GAC | CAG | ATA | TGC | ATT | GGA | TAC | CAT | GCC | AAT | AAT | TCC | ACA | GAG | AAG | 138 |
| Asp | Gln | Ile | Cys | Ile | Gly | Tyr | His | Ala | Asn | Asn | Ser | Thr | Glu | Lys | |
| 1 | | | | 5 | | | | | 10 | | | | | 15 | |
| GTC | GAC | ACA | ATT | CTA | GAG | CGG | AAC | GTC | ACT | GTG | ACT | CAT | GCC | AAG | 183 |
| Val | Asp | Thr | Ile | Leu | Glu | Arg | Asn | Val | Thr | Val | Thr | His | Ala | Lys | |
| | | | | 20 | | | | | 25 | | | | | 30 | |
| GAC | ATC | CTT | GAG | AAG | ACC | CAT | AAC | GGA | AAG | TTA | TGC | AAA | CTA | AAC | 228 |
| Asp | Ile | Leu | Glu | Lys | Thr | His | Asn | Gly | Lys | Leu | Cys | Lys | Leu | Asn | |
| | | | | 35 | | | | | 40 | | | | | 45 | |
| GGA | ATC | CCT | CCA | CTT | GAA | CTA | GGG | GAC | TGT | AGC | ATT | GCC | GGA | TGG | 273 |
| Gly | Ile | Pro | Pro | Leu | Glu | Leu | Gly | Asp | Cys | Ser | Ile | Ala | Gly | Trp | |
| | | | | 50 | | | | | 55 | | | | | 60 | |
| CTC | CTT | GGA | AAT | CCA | AAA | TGT | GAT | AGG | CTT | CTA | AGT | GTG | CCA | GAA | 318 |
| Leu | Leu | Gly | Asn | Pro | Lys | Cys | Asp | Arg | Leu | Leu | Ser | Val | Pro | Glu | |
| | | | | 65 | | | | | 70 | | | | | 75 | |
| CGG | TCC | TAT | ATA | TTG | GAG | AAA | GAA | AAC | CCG | AGA | GAC | GGT | TTG | TGT | 363 |
| Arg | Ser | Tyr | Ile | Leu | Glu | Lys | Glu | Asn | Pro | Arg | Asp | Gly | Leu | Cys | |
| | | | | 80 | | | | | 85 | | | | | 90 | |
| TAT | CCA | GGC | AGC | TTC | AAT | GAT | TAT | GAA | GAA | TTG | AAA | CAT | CTC | CTC | 408 |
| Tyr | Pro | Gly | Ser | Phe | Asn | Asp | Tyr | Glu | Glu | Leu | Lys | His | Leu | Leu | |
| | | | | 95 | | | | | 100 | | | | | 105 | |
| AGC | AGC | GTG | AAA | CAT | TTC | GAG | AAA | GTA | AAG | ATT | CTG | CCC | AAA | GAT | 453 |
| Ser | Ser | Val | Lys | His | Phe | Glu | Lys | Val | Lys | Ile | Leu | Pro | Lys | Asp | |
| | | | | 110 | | | | | 115 | | | | | 120 | |
| AGA | TGG | ACA | CAG | CAT | ACA | ACA | ACT | GGA | GGT | TCA | CGG | GCC | TGC | GCG | 498 |
| Arg | Trp | Thr | Gln | His | Thr | Thr | Thr | Gly | Gly | Ser | Arg | Ala | Cys | Ala | |
| | | | | 125 | | | | | 130 | | | | | 135 | |
| GTG | TCT | GGT | AAT | CCA | TCA | TTT | TTC | AGG | AAC | ATG | GTC | TGG | CTG | ACA | 543 |
| Val | Ser | Gly | Asn | Pro | Ser | Phe | Phe | Arg | Asn | Met | Val | Trp | Leu | Thr | |
| | | | | 140 | | | | | 145 | | | | | 150 | |
| AAG | GAA | GGA | TCA | GAT | TAT | CCG | GTT | GCC | AAA | GGA | TCG | TAC | AAC | AAT | 588 |
| Lys | Glu | Gly | Ser | Asp | Tyr | Pro | Val | Ala | Lys | Gly | Ser | Tyr | Asn | Asn | |
| | | | | 155 | | | | | 160 | | | | | 165 | |
| ACA | AGC | GGA | GAA | CAA | ATG | CTA | ATA | ATT | TGG | GGG | GTG | CAC | CAT | CCC | 633 |
| Thr | Ser | Gly | Glu | Gln | Met | Leu | Ile | Ile | Trp | Gly | Val | His | His | Pro | |
| | | | | 170 | | | | | 175 | | | | | 180 | |
| ATT | GAT | GAG | ACA | GAA | CAA | AGA | ACA | TTG | TAC | CAG | AAT | GTG | GGA | ACC | 678 |
| Ile | Asp | Glu | Thr | Glu | Gln | Arg | Thr | Leu | Tyr | Gln | Asn | Val | Gly | Thr | |
| | | | | 185 | | | | | 190 | | | | | 195 | |
| TAT | GTT | TCC | GTA | GGC | ACA | TCA | ACA | TTG | AAC | AAA | AGG | TCA | ACC | CCA | 723 |
| Tyr | Val | Ser | Val | Gly | Thr | Ser | Thr | Leu | Asn | Lys | Arg | Ser | Thr | Pro | |
| | | | | 200 | | | | | 205 | | | | | 210 | |
| GAA | ATA | GCA | ACA | AGG | CCT | AAA | GTG | AAT | GGA | CAA | GGA | GGT | AGA | ATG | 768 |
| Glu | Ile | Ala | Thr | Arg | Pro | Lys | Val | Asn | Gly | Gln | Gly | Gly | Arg | Met | |
| | | | | 215 | | | | | 220 | | | | | 225 | |
| GAA | TTC | TCT | TGG | ACC | CTC | TTG | GAT | ATG | TGG | GAC | ACC | ATA | AAT | TTT | 813 |
| Glu | Phe | Ser | Trp | Thr | Leu | Leu | Asp | Met | Trp | Asp | Thr | Ile | Asn | Phe | |
| | | | | 230 | | | | | 235 | | | | | 240 | |
| GAG | AGT | ACT | GGT | AAT | CTA | ATT | GCA | CCA | GAG | TAT | GGA | TTC | AAA | ATA | 858 |

|     |     |     |     |     |     |     |     |     |     |     |     |     |     |     |     |     |
|---|---|---|---|---|---|---|---|---|---|---|---|---|---|---|---|---|
| Glu | Ser | Thr | Gly | Asn<br>245 | Leu | Ile | Ala | Pro | Glu<br>250 | Tyr | Gly | Phe | Lys | Ile<br>255 | | |
| TCG | AAA | AGA | GGT | AGT | TCA | GGG | ATC | ATG | AAA | ACA | GAA | GGA | ACA | CTT | | 903 |
| Ser | Lys | Arg | Gly | Ser<br>260 | Ser | Gly | Ile | Met | Lys<br>265 | Thr | Glu | Gly | Thr | Leu<br>270 | | |
| GAG | AAC | TGT | GAG | ACC | AAA | TGC | CAA | ACT | CCT | TTG | GGA | GCA | ATA | AAT | | 948 |
| Glu | Asn | Cys | Glu | Thr<br>275 | Lys | Cys | Gln | Thr | Pro<br>280 | Leu | Gly | Ala | Ile | Asn<br>285 | | |
| ACA | ACA | TTA | CCT | TTT | CAC | AAT | GTC | CAC | CCA | CTG | ACA | ATA | GGT | GAG | | 993 |
| Thr | Thr | Leu | Pro | Phe<br>290 | His | Asn | Val | His | Pro<br>295 | Leu | Thr | Ile | Gly | Glu<br>300 | | |
| TGC | CCC | AAA | TAT | GTA | AAA | TCG | GAG | AAG | TTG | GTC | TTA | GCA | ACA | GGA | | 1038 |
| Cys | Pro | Lys | Tyr | Val<br>305 | Lys | Ser | Glu | Lys | Leu<br>310 | Val | Leu | Ala | Thr | Gly<br>315 | | |
| CTA | AGG | AAT | GTT | CCC | CAG | ATT | GAA | TCA | AGA | GGA | TTG | TTT | GGG | GCA | | 1083 |
| Leu | Arg | Asn | Val | Pro<br>320 | Gln | Ile | Glu | Ser | Arg<br>325 | Gly | Leu | Phe | Gly | Ala<br>330 | | |
| ATA | GCT | GGT | TTT | ATA | GAA | GGA | GGA | TGG | CAA | GGA | ATG | GTT | GAC | GGT | | 1128 |
| Ile | Ala | Gly | Phe | Ile<br>335 | Glu | Gly | Gly | Trp | Gln<br>330 | Gly | Met | Val | Asp | Gly<br>345 | | |
| TGG | TAT | GGA | TAC | CAT | CAC | AGC | AAT | GAC | CAG | GGA | TCA | GGG | TAT | GCA | | 1173 |
| Trp | Tyr | Gly | Tyr | His<br>350 | His | Ser | Asn | Asp | Gln<br>355 | Gly | Ser | Gly | Tyr | Ala<br>360 | | |
| GCA | GAC | AAA | GAA | TCC | ACT | CAA | AAG | GCA | TTT | GAT | GGA | ATC | ACC | AAC | | 1218 |
| Ala | Asp | Lys | Glu | Ser<br>365 | Thr | Gln | Lys | Ala | Phe<br>370 | Asp | Gly | Ile | Thr | Asn<br>375 | | |
| AAG | GTA | AAT | TCT | GTG | ATT | GAA | AAG | ATA | AAC | ACC | CAA | TTT | GAA | GCT | | 1263 |
| Lys | Val | Asn | Ser | Val<br>380 | Ile | Glu | Lys | Ile | Asn<br>385 | Thr | Gln | Phe | Glu | Ala<br>390 | | |
| GTT | GGG | AAA | GAA | TTC | GGT | AAC | TTA | GAG | AAA | AGA | CTG | GAG | AAC | TTG | | 1308 |
| Val | Gly | Lys | Glu | Phe<br>395 | Gly | Asn | Leu | Glu | Lys<br>400 | Arg | Leu | Glu | Asn | Leu<br>405 | | |
| AAC | AAA | AAG | ATG | GAA | GAC | GGG | TTT | CTA | GAT | GTG | TGG | ACA | TAC | AAT | | 1353 |
| Asn | Lys | Lys | Met | Glu<br>410 | Asp | Gly | Phe | Leu | Asp<br>415 | Val | Trp | Thr | Tyr | Asn<br>420 | | |
| GCT | GAG | CTT | TTA | GTT | CTG | ATG | GAA | AAT | GAG | AGG | ACA | CTT | GAC | TTT | | 1398 |
| Ala | Glu | Leu | Leu | Val<br>425 | Leu | Met | Glu | Asn | Glu<br>430 | Arg | Thr | Leu | Asp | Phe<br>435 | | |
| CAT | GAT | TCT | AAT | GTC | AAG | AAT | CTG | TAT | AGT | AAA | GTC | AGA | ATG | CAG | | 1443 |
| His | Asp | Ser | Asn | Val<br>440 | Lys | Asn | Leu | Tyr | Ser<br>445 | Lys | Val | Arg | Met | Gln<br>450 | | |
| CTG | AGA | GAC | AAC | GTC | AAA | GAA | CTA | GGA | AAT | GGA | TGT | TTT | GAA | TTT | | 1488 |
| Leu | Arg | Asp | Asn | Val<br>455 | Lys | Glu | Leu | Gly | Asn<br>460 | Gly | Cys | Phe | Glu | Phe<br>465 | | |
| TAT | CAC | AAA | TGT | GAT | GAT | GAA | TGC | ATG | AAT | AGT | GTG | AAA | AAC | GGG | | 1533 |
| Tyr | His | Lys | Cys | Asp<br>470 | Asp | Glu | Cys | Met | Asn<br>475 | Ser | Val | Lys | Asn | Gly<br>480 | | |
| ACA | TAT | GAT | TAT | CCC | AAG | TAT | GAA | GAA | GAG | TCT | AAA | CTA | AAT | AGA | | 1578 |
| Thr | Tyr | Asp | Tyr | Pro<br>495 | Lys | Tyr | Glu | Glu | Glu<br>500 | Ser | Lys | Leu | Asn | Arg<br>505 | | |
| AAT | GAA | ATC | AAA | GGG | GTA | AAA | TTG | AGC | AGC | ATG | GGG | GTT | TAT | CAA | | 1623 |
| Asn | Glu | Ile | Lys | Gly<br>510 | Val | Lys | Leu | Ser | Ser<br>515 | Met | Gly | Val | Tyr | Gln<br>520 | | |
| ATC | CTT | GCC | ATT | TAT | GCT | ACA | GTA | GCA | GGT | TCT | ATG | TCA | CTG | GCA | | 1668 |
| Ile | Leu | Ala | Ile | Tyr<br>525 | Ala | Thr | Val | Ala | Gly<br>530 | Ser | Met | Ser | Leu | Ala<br>535 | | |
| ATC | ATG | ATG | GCT | GGG | ATC | TCT | TTC | TGG | GTG | TGC | TCC | AAC | GGG | TCT | | 1713 |
| Ile | Met | Met | Ala | Gly<br>540 | Ile | Ser | Phe | Trp | Val<br>545 | Cys | Ser | Asn | Gly | Ser<br>550 | | |
| CTG | CAG | TGC | AGG | ATC | TGC | ATA | TGATTATAAG | TCATTTTATA | ATTAAAAACA | | | | | | | 1764 |

Leu Gln Cys Arg Ile Cys Ile
555

CCCTTGTTTC TGCTAGCCG                                                                    1783

(2) INFORMATION FOR SEQ ID NO:47:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:47:

TCCGTTTAGT TTGCATAACT TTCCG                                                              25

(2) INFORMATION FOR SEQ ID NO:48:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: other nucleic acid (synthetic DNA)

(iii) HYPOTHETICAL:

(iv) ANTI-SENSE:

```
        ( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:48:

TCCGGGATCA TGAAAACAGA AGGAAC                                                                      2 6

( 2 ) INFORMATION FOR SEQ ID NO:49:

( i ) SEQUENCE CHARACTERISTICS:
                ( A ) LENGTH: 1135 base pairs
                ( B ) TYPE: nucleic acid
                ( C ) STRANDEDNESS: double
                ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
                ( A ) ORGANISM: A/Okuda/57
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
```

(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:49:

| | | | | | | |
|---|---|---|---|---|---|---|
| CTAGCAAAAG | CAGGGGTTAT | ACCATAGAAA | ACCAAAAGCA | AAACAATGGC | CATCATTTAT | 60 |
| CTCATTCTCC | TGTTCACAGC | AGTGAGAGGG | GACCAGATAT | GCATTGGATA | CCATGCCAAT | 120 |
| AATTCCACAG | AGAAGGTCGA | CACAATTCTA | GAGCGGAACG | TCACTGTGAC | TCATGCCAAG | 180 |
| GACATCCTTG | AGAAGACCCA | TAACGGAAAG | TTATGCAAAC | TAAACGGATC | CGGGATCATG | 240 |
| AAAACAGAAG | GAACACTTGA | GAACTGTGAG | ACCAAATGCC | AAACTCCTTT | GGGAGCAATA | 300 |
| AATACAACAT | TACCTTTTCA | CAATGTCCAC | CCACTGACAA | TAGGTGAGTG | CCCCAAATAT | 360 |
| GTAAAATCGG | AGAAGTTGGT | CTTAGCAACA | GGACTAAGGA | ATGTTCCCCA | GATTGAATCA | 420 |
| AGAGGATTGT | TTGGGGCAAT | AGCTGGTTTT | ATAGAAGGAG | GATGGCAAGG | AATGGTTGAC | 480 |
| GGTTGGTATG | GATACCATCA | CAGCAATGAC | CAGGGATCAG | GGTATGCAGC | AGACAAAGAA | 540 |
| TCCACTCAAA | AGGCATTTGA | TGGAATCACC | AACAAGGTAA | ATTCTGTGAT | TGAAAAGATA | 600 |
| AACACCCAAT | TTGAAGCTGT | TGGGAAAGAA | TTCGGTAACT | TAGAGAAAAG | ACTGGAGAAC | 660 |
| TTGAACAAAA | AGATGGAAGA | CGGGTTTCTA | GATGTGTGGA | CATACAATGC | TGAGCTTTTA | 720 |
| GTTCTGATGG | AAAATGAGAG | GACACTTGAC | TTTCATGATT | CTAATGTCAA | GAATCTGTAT | 780 |
| AGTAAAGTCA | GAATGCAGCT | GAGAGACAAC | GTCAAAGAAC | TAGGAAATGG | ATGTTTTGAA | 840 |
| TTTTATCACA | AATGTGATGA | TGAATGCATG | AATAGTGTGA | AAAACGGGAC | ATATGATTAT | 900 |
| CCCAAGTATG | AAGAAGAGTC | TAAACTAAAT | AGAAATGAAA | TCAAAGGGGT | AAAATTGAGC | 960 |
| AGCATGGGGG | TTTATCAAAT | CCTTGCCATT | TATGCTACAG | TAGCAGGTTC | TATGTCACTG | 1020 |
| GCAATCATGA | TGGCTGGGAT | CTCTTTCTGG | GTGTGCTCCA | ACGGGTCTCT | GCAGTGCAGG | 1080 |
| ATCTGCATAT | GATTATAAGT | CATTTTATAA | TTAAAAACAC | CCTTGTTTCT | GCTAG | 1135 |

(2) INFORMATION FOR SEQ ID NO:50:

(i) SEQUENCE CHARACTERISTICS:
(A) LENGTH: 348 amino acids
(B) TYPE: amino acid
(C) STRANDEDNESS: single
(D) TOPOLOGY: linear (ii) MOLECULE TYPE: peptide (iii) HYPOTHETICAL:

(iv) ANTI-SENSE:

(v) FRAGMENT TYPE:

(vi) ORIGINAL SOURCE:
(A) ORGANISM:

(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:50:

| | | | | | | | | | | | | | | |
|---|---|---|---|---|---|---|---|---|---|---|---|---|---|---|
| Met | Ala | Ile | Ile | Tyr | Leu | Ile | Leu | Leu | Phe | Thr | Ala | Val | Arg | Gly |
| -15 | | | | -10 | | | | | -5 | | | | | |
| Asp | Gln | Ile | Cys | Ile | Gly | Tyr | His | Ala | Asn | Asn | Ser | Thr | Glu | Lys |
| 1 | | | | 5 | | | | | 10 | | | | | 15 |
| Val | Asp | Thr | Ile | Leu | Glu | Arg | Asn | Val | Thr | Val | Thr | His | Ala | Lys |
| | | | | 20 | | | | | 25 | | | | | 30 |
| Asp | Ile | Leu | Glu | Lys | Thr | His | Asn | Gly | Lys | Leu | Cys | Lys | Leu | Asn |
| | | | | 35 | | | | | 40 | | | | | 45 |
| Gly | Ser | Gly | Ile | Met | Lys | Thr | Glu | Gly | Thr | Leu | Glu | Asn | Cys | Glu |
| | | | | 50 | | | | | 55 | | | | | 60 |
| Thr | Lys | Cys | Gln | Thr | Pro | Leu | Gly | Ala | Ile | Asn | Thr | Thr | Leu | Pro |
| | | | | 65 | | | | | 70 | | | | | 75 |
| Phe | His | Asn | Val | His | Pro | Leu | Thr | Ile | Gly | Glu | Cys | Pro | Lys | Tyr |
| | | | | 80 | | | | | 85 | | | | | 90 |
| Val | Lys | Ser | Glu | Lys | Leu | Val | Leu | Ala | Thr | Gly | Leu | Arg | Asn | Val |
| | | | | 95 | | | | | 100 | | | | | 105 |
| Pro | Gln | Ile | Glu | Ser | Arg | Gly | Leu | Phe | Gly | Ala | Ile | Ala | Gly | Phe |
| | | | | 110 | | | | | 115 | | | | | 120 |
| Ile | Glu | Gly | Gly | Trp | Gln | Gly | Met | Val | Asp | Gly | Trp | Tyr | Gly | Tyr |
| | | | | 125 | | | | | 130 | | | | | 135 |
| His | His | Ser | Asn | Asp | Gln | Gly | Ser | Gly | Tyr | Ala | Ala | Asp | Lys | Glu |
| | | | | 140 | | | | | 145 | | | | | 150 |
| Ser | Thr | Gln | Lys | Ala | Phe | Asp | Gly | Ile | Thr | Asn | Lys | Val | Asn | Ser |
| | | | | 155 | | | | | 160 | | | | | 165 |
| Val | Ile | Glu | Lys | Ile | Asn | Thr | Gln | Phe | Glu | Ala | Val | Gly | Lys | Glu |
| | | | | 170 | | | | | 175 | | | | | 180 |
| Phe | Gly | Asn | Leu | Glu | Lys | Arg | Leu | Glu | Asn | Leu | Asn | Lys | Lys | Met |
| | | | | 185 | | | | | 190 | | | | | 195 |

| | | | | | | | | | | | | | | |
|---|---|---|---|---|---|---|---|---|---|---|---|---|---|---|
| Glu | Asp | Gly | Phe | Leu<br>200 | Asp | Val | Trp | Thr | Tyr<br>205 | Asn | Ala | Glu | Leu | Leu<br>210 |
| Val | Leu | Met | Glu | Asn<br>215 | Glu | Arg | Thr | Leu | Asp<br>220 | Phe | His | Asp | Ser | Asn<br>225 |
| Val | Lys | Asn | Leu | Tyr<br>230 | Ser | Lys | Val | Arg | Met<br>235 | Gln | Leu | Arg | Asp | Asn<br>240 |
| Val | Lys | Glu | Leu | Gly<br>245 | Asn | Gly | Cys | Phe | Glu<br>250 | Phe | Tyr | His | Lys | Cys<br>255 |
| Asp | Asp | Glu | Cys | Met<br>260 | Asn | Ser | Val | Lys | Asn<br>265 | Gly | Thr | Tyr | Asp | Tyr<br>270 |
| Pro | Lys | Tyr | Glu | Glu<br>275 | Glu | Ser | Lys | Leu | Asn<br>280 | Arg | Asn | Glu | Ile | Lys<br>285 |
| Gly | Val | Lys | Leu | Ser<br>290 | Ser | Met | Gly | Val | Tyr<br>295 | Gln | Ile | Leu | Ala | Ile<br>300 |
| Tyr | Ala | Thr | Val | Ala<br>305 | Gly | Ser | Met | Ser | Leu<br>310 | Ala | Ile | Met | Met | Ala<br>315 |
| Gly | Ile | Ser | Phe | Trp<br>320 | Val | Cys | Ser | Asn | Gly<br>325 | Ser | Leu | Gln | Cys | Arg<br>330 |
| Ile | Cys | Ile | | | | | | | | | | | | |

( 2 ) INFORMATION FOR SEQ ID NO:51:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:

(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:51:

GATCTAGAAG CAAAGCAGGG GATAATTCTA 30

(2) INFORMATION FOR SEQ ID NO:52:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:52:

ACAGATCTAG TAGAAACAAG GGTGTTTTT 29

(2) INFORMATION FOR SEQ ID NO:53:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:53:

CGGCTAGCAG AAACAAGGGT GTTTTAATT 30

( 2 ) INFORMATION FOR SEQ ID NO:54:

( i ) SEQUENCE CHARACTERISTICS:
    ( A ) LENGTH: 1777 base pairs
    ( B ) TYPE: nucleic acid
    ( C ) STRANDEDNESS: double
    ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

( v i ) ORIGINAL SOURCE:
    ( A ) ORGANISM: A2/Aichi/2/68
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:

( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:54:

```
GATCTAGAAG CAAAGCAGGG GATAATTCTA TTAATC                                    36

ATG AAG ACC ATC ATT GCT TTG AGC TAC ATT TTC TGT CTG GCT CTC                81
Met Lys Thr Ile Ile Ala Leu Ser Tyr Ile Phe Cys Leu Ala Leu
-15              -10                      -5

GGC CAA GAC CTT CCA GGA AAT GAC AAC AGC ACA GCA ACG CTG TGC               126
Gly Gln Asp Leu Pro Gly Asn Asp Asn Ser Thr Ala Thr Leu Cys
      1             5                   10

CTG GGA CAT CAT GCG GTG CCA AAC GGA ACA CTA GTG AAA ACA ATC               171
Leu Gly His His Ala Val Pro Asn Gly Thr Leu Val Lys Thr Ile
 15              20                      25

ACA GAT GAT CAG ATT GAA GTG ACT AAT GCT ACT GAG CTA GTT CAG               216
Thr Asp Asp Gln Ile Glu Val Thr Asn Ala Thr Glu Leu Val Gln
 30              35                      40

AGC TCC TCA ACG GGG AAA ATA TGC AAC AAT CCT CAT CGA ATC CTT               261
Ser Ser Ser Thr Gly Lys Ile Cys Asn Asn Pro His Arg Ile Leu
 45              50                      55

GAT GGA ATA GAC TGC ACA CTG ATA GAT GCT CTA TTG GGG GAC CCT               306
Asp Gly Ile Asp Cys Thr Leu Ile Asp Ala Leu Leu Gly Asp Pro
 60              65                      70

CAT TGT GAT GTT TTT CAA AAT GAG ACA TGG GAC CTT TTC GTT GAA               351
His Cys Asp Val Phe Gln Asn Glu Thr Trp Asp Leu Phe Val Glu
 75              80                      85

CGC AGC AAA GCT TTC AGC AAC TGT TAC CCT TAT GAT GTG CCA GAT               396
Arg Ser Lys Ala Phe Ser Asn Cys Tyr Pro Tyr Asp Val Pro Asp
 90              95                     100

TAT GCC TCC CTT AGG TCA CTA GTT GCC TCG TCA GGC ACT CTG GAG               441
Tyr Ala Ser Leu Arg Ser Leu Val Ala Ser Ser Gly Thr Leu Glu
105             110                     115

TTT ATC ACT GAG GGT TTC ACT TGG ACT GGG GTC ACT CAG AAT GGG               486
Phe Ile Thr Glu Gly Phe Thr Trp Thr Gly Val Thr Gln Asn Gly
120             125                     130

GGA AGC AAT GCT TGC AAA AGG GGA CCT GGT AGC GGT TTT TTC AGT               531
Gly Ser Asn Ala Cys Lys Arg Gly Pro Gly Ser Gly Phe Phe Ser
135             140                     145

AGA CTG AAC TGG TTG ACC AAA TCA GGA AGC ACA TAT CCA GTG CTG               576
Arg Leu Asn Trp Leu Thr Lys Ser Gly Ser Thr Tyr Pro Val Leu
150             155                     160

AAC GTG ACT ATG CCA AAC AAT GAC AAT TTT GAC AAA CTA TAC ATT               621
Asn Val Thr Met Pro Asn Asn Asp Asn Phe Asp Lys Leu Tyr Ile
```

|     |     |     |     |     |     |     |     |     |     |     |     |     |     |     |      |
|-----|-----|-----|-----|-----|-----|-----|-----|-----|-----|-----|-----|-----|-----|-----|------|
| 165 |     |     |     |     | 170 |     |     |     |     | 175 |     |     |     |     |      |
| TGG | GGG | ATT | CAC | CAC | CCG | AGC | ACG | AAC | CAA | GAA | CAA | ACC | AGC | CTG | 666  |
| Trp | Gly | Ile | His | His | Pro | Ser | Thr | Asn | Gln | Glu | Gln | Thr | Ser | Leu |      |
| 180 |     |     |     |     | 185 |     |     |     |     | 190 |     |     |     |     |      |
| TAT | GTT | CAA | GCA | TCA | GGG | AGA | GTC | ACA | GTC | TCT | ACC | AGG | AGA | AGC | 711  |
| Tyr | Val | Gln | Ala | Ser | Gly | Arg | Val | Thr | Val | Ser | Thr | Arg | Arg | Ser |      |
| 195 |     |     |     |     | 200 |     |     |     |     | 205 |     |     |     |     |      |
| CAG | CAA | ACT | ATA | ATC | CCG | AAT | ATC | GGG | TCC | AGA | CCC | TGG | GTA | AGG | 756  |
| Gln | Gln | Thr | Ile | Ile | Pro | Asn | Ile | Gly | Ser | Arg | Pro | Trp | Val | Arg |      |
| 210 |     |     |     |     | 215 |     |     |     |     | 220 |     |     |     |     |      |
| GGT | CTG | TCT | AGT | AGA | ATA | AGC | ATC | TAT | TGG | ACA | ATA | GTT | AAG | CCG | 801  |
| Gly | Leu | Ser | Ser | Arg | Ile | Ser | Ile | Tyr | Trp | Thr | Ile | Val | Lys | Pro |      |
| 225 |     |     |     |     | 230 |     |     |     |     | 235 |     |     |     |     |      |
| GGA | GAC | GTA | CTG | GTA | ATT | AAT | AGT | AAT | GGG | AAC | CTA | ATC | GCT | CCT | 846  |
| Gly | Asp | Val | Leu | Val | Ile | Asn | Ser | Asn | Gly | Asn | Leu | Ile | Ala | Pro |      |
| 240 |     |     |     |     | 245 |     |     |     |     | 250 |     |     |     |     |      |
| CGG | GGT | TAT | TTC | AAA | ATG | CGC | ACT | GGG | AAA | AGC | TCA | ATA | ATG | AGG | 891  |
| Arg | Gly | Tyr | Phe | Lys | Met | Arg | Thr | Gly | Lys | Ser | Ser | Ile | Met | Arg |      |
| 255 |     |     |     |     | 260 |     |     |     |     | 265 |     |     |     |     |      |
| TCA | GAT | GCA | CCT | ATT | GAT | ACC | TGT | ATT | TCT | GAA | TGC | ATC | ACT | CCA | 936  |
| Ser | Asp | Ala | Pro | Ile | Asp | Thr | Cys | Ile | Ser | Glu | Cys | Ile | Thr | Pro |      |
| 270 |     |     |     |     | 275 |     |     |     |     | 280 |     |     |     |     |      |
| AAT | GGA | AGC | ATT | CCC | AAT | GAC | AAG | CCC | TTT | CAA | AAC | GTA | AAC | AAG | 981  |
| Asn | Gly | Ser | Ile | Pro | Asn | Asp | Lys | Pro | Phe | Gln | Asn | Val | Asn | Lys |      |
| 285 |     |     |     |     | 290 |     |     |     |     | 295 |     |     |     |     |      |
| ATC | ACA | TAT | GGA | GCA | TGC | CCC | AAG | TAT | GTT | AAG | CAA | AAC | ACC | CTG | 1026 |
| Ile | Thr | Tyr | Gly | Ala | Cys | Pro | Lys | Tyr | Val | Lys | Gln | Asn | Thr | Leu |      |
| 300 |     |     |     |     | 305 |     |     |     |     | 310 |     |     |     |     |      |
| AAG | TTG | GCA | ACA | GGG | ATG | CGG | AAT | GTA | CCA | GAG | AAA | CAA | ACT | AGA | 1071 |
| Lys | Leu | Ala | Thr | Gly | Met | Arg | Asn | Val | Pro | Glu | Lys | Gln | Thr | Arg |      |
| 315 |     |     |     |     | 320 |     |     |     |     | 325 |     |     |     |     |      |
| GGC | CTA | TTC | GGC | GCA | ATA | GCA | GGT | TTC | ATA | GAA | AAT | GGT | TGG | GAG | 1116 |
| Gly | Leu | Phe | Gly | Ala | Ile | Ala | Gly | Phe | Ile | Glu | Asn | Gly | Trp | Glu |      |
| 330 |     |     |     |     | 335 |     |     |     |     | 340 |     |     |     |     |      |
| GGA | ATG | ATA | GAC | GGT | TGG | TAC | GGT | TTC | AGG | CAT | CAA | AAT | TCT | GAG | 1161 |
| Gly | Met | Ile | Asp | Gly | Trp | Tyr | Gly | Phe | Arg | His | Gln | Asn | Ser | Glu |      |
| 345 |     |     |     |     | 350 |     |     |     |     | 355 |     |     |     |     |      |
| GGC | ACA | GGA | CAA | GCA | GCA | GAT | CTT | AAA | AGC | ACT | CAA | GCA | GCC | ATC | 1206 |
| Gly | Thr | Gly | Gln | Ala | Ala | Asp | Leu | Lys | Ser | Thr | Gln | Ala | Ala | Ile |      |
| 360 |     |     |     |     | 365 |     |     |     |     | 370 |     |     |     |     |      |
| GAC | CAA | ATC | AAT | GGG | AAA | TTG | AAC | AGG | GTA | ATC | GAG | AAG | ACG | AAC | 1251 |
| Asp | Gln | Ile | Asn | Gly | Lys | Leu | Asn | Arg | Val | Ile | Glu | Lys | Thr | Asn |      |
| 375 |     |     |     |     | 380 |     |     |     |     | 385 |     |     |     |     |      |
| GAG | AAA | TTC | CAT | CAA | ATC | GAA | AAG | GAA | TTC | TCA | GAA | GTA | GAA | GGG | 1296 |
| Glu | Lys | Phe | His | Gln | Ile | Glu | Lys | Glu | Phe | Ser | Glu | Val | Glu | Gly |      |
| 390 |     |     |     |     | 395 |     |     |     |     | 400 |     |     |     |     |      |
| AGA | ATT | CAG | GAC | CTC | GAG | AAA | TAC | GTT | GAA | GAC | ACT | AAA | ATA | GAT | 1341 |
| Arg | Ile | Gln | Asp | Leu | Glu | Lys | Tyr | Val | Glu | Asp | Thr | Lys | Ile | Asp |      |
| 405 |     |     |     |     | 410 |     |     |     |     | 415 |     |     |     |     |      |
| CTC | TGG | TCT | TAC | AAT | GCG | GAG | CTT | CTT | GTC | GCT | CTG | GAG | AAT | CAA | 1386 |
| Leu | Trp | Ser | Tyr | Asn | Ala | Glu | Leu | Leu | Val | Ala | Leu | Glu | Asn | Gln |      |
| 420 |     |     |     |     | 425 |     |     |     |     | 430 |     |     |     |     |      |
| CAT | ACA | ATT | GAC | CTG | ACT | GAC | TCG | GAA | ATG | AAC | AAG | CTG | TTT | GAA | 1431 |
| His | Thr | Ile | Asp | Leu | Thr | Asp | Ser | Glu | Met | Asn | Lys | Leu | Phe | Glu |      |
| 435 |     |     |     |     | 440 |     |     |     |     | 445 |     |     |     |     |      |
| AAA | ACA | AGG | AGG | CAA | CTG | AGG | GAA | AAT | GCT | GAA | GAG | ATG | GGC | AAT | 1476 |
| Lys | Thr | Arg | Arg | Gln | Leu | Arg | Glu | Asn | Ala | Glu | Glu | Met | Gly | Asn |      |
| 450 |     |     |     |     | 455 |     |     |     |     | 460 |     |     |     |     |      |
| GGT | TGC | TTC | AAA | ATA | TAC | CAC | AAA | TGT | GAC | AAC | GCT | TGC | ATA | GAG | 1521 |
| Gly | Cys | Phe | Lys | Ile | Tyr | His | Lys | Cys | Asp | Asn | Ala | Cys | Ile | Glu |      |

|     |     |     |     | 465 |     |     |     |     | 470 |     |     |     |     | 475 |     |     |     |      |
|-----|-----|-----|-----|-----|-----|-----|-----|-----|-----|-----|-----|-----|-----|-----|-----|-----|-----|------|

```
            465                           470                         475
TCA  ATC  AGA  AAT  GGT  ACT  TAT  GAC  CAT  GAT  GTA  TAC  AGA  GAC  GAA        1566
Ser  Ile  Arg  Asn  Gly  Thr  Tyr  Asp  His  Asp  Val  Tyr  Arg  Asp  Glu
480                 485                           490

GCA  TTA  AAC  AAC  CGG  TTT  CAG  ATC  AAA  GGT  GTT  GAA  CTG  AAG  TCT        1611
Ala  Leu  Asn  Asn  Arg  Phe  Gln  Ile  Lys  Gly  Val  Glu  Leu  Lys  Ser
495                 500                           505

GGA  TAC  AAA  GAC  TGG  ATC  CTG  TGG  ATT  TCC  TTT  GCC  ATA  TCA  TGC        1656
Gly  Tyr  Lys  Asp  Trp  Ile  Leu  Trp  Ile  Ser  Phe  Ala  Ile  Ser  Cys
510                 515                           520

TTT  TTG  CTT  TGT  GTT  GTT  TTG  CTG  GGG  TTC  ATC  ATG  TGG  GCC  TGC        1701
Phe  Leu  Leu  Cys  Val  Val  Leu  Leu  Gly  Phe  Ile  Met  Trp  Ala  Cys
525                 530                           535

CAG  AGA  GGC  AAC  ATT  AGG  TGC  AAC  ATT  TGC  ATT  TGAGTGTATT  AGTAATTAAA    1754
Gln  Arg  Gly  Asn  Ile  Arg  Cys  Asn  Ile  Cys  Ile
40                  545                      550

AACACCCTTG  TTTCTGCTAG  CCG                                                       1777
```

( 2 ) INFORMATION FOR SEQ ID NO:55:

( i ) SEQUENCE CHARACTERISTICS:
           ( A ) LENGTH: 20 bases
           ( B ) TYPE: nucleic acid
           ( C ) STRANDEDNESS: single
           ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
           ( A ) ORGANISM:
           ( B ) STRAIN:
           ( C ) INDIVIDUAL ISOLATE:
           ( D ) DEVELOPMENTAL STAGE:
           ( E ) HAPLOTYPE:
           ( F ) TISSUE TYPE:
           ( G ) CELL TYPE:
           ( H ) CELL LINE:
           ( I ) ORGANELLE:

( v i i ) IMMEDIATE SOURCE:
           ( A ) LIBRARY:
           ( B ) CLONE:

( v i i i ) POSITION IN GENOME:
           ( A ) CHROMOSOME/SEGMENT:
           ( B ) MAP POSITION:
           ( C ) UNITS:

( i x ) FEATURE:
           ( A ) NAME/KEY:
           ( B ) LOCATION:
           ( C ) IDENTIFICATION METHOD:
           ( D ) OTHER INFORMATION:

( x ) PUBLICATION INFORMATION:
           ( A ) AUTHORS:
           ( B ) TITLE:
           ( C ) JOURNAL:
           ( D ) VOLUME:
           ( E ) ISSUE:
           ( F ) PAGES:
           ( G ) DATE:
           ( H ) DOCUMENT NUMBER:
           ( I ) FILING DATE:
           ( J ) PUBLICATION DATE:
           ( K ) RELEVANT RESIDUES IN SEQ ID NO:

( x i ) SEQUENCE DESCRIPTION: SEQ ID NO:55:

ATTGTTGCAT ATTTTCCCCG 20

( 2 ) INFORMATION FOR SEQ ID NO:56:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: other nucleic acid (synthetic DNA)

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:56:

ATTGATACCT GTATTTCTGA 20

( 2 ) INFORMATION FOR SEQ ID NO:57:

( i ) SEQUENCE CHARACTERISTICS:
        ( A ) LENGTH: 1110 base pairs
        ( B ) TYPE: nucleic acid
        ( C ) STRANDEDNESS: double
        ( D ) TOPOLOGY: linear ( i i ) MOLECULE TYPE: cDNA to genomic RNA ( i i i ) HYPOTHETICAL:

( i v ) ANTI-SENSE:

( v ) FRAGMENT TYPE:

(v i) ORIGINAL SOURCE:
    (A) ORGANISM: A2/Aichi/2/68
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(v i i) IMMEDIATE SOURCE:
    (A) LIBRARY:
    (B) CLONE:

(v i i i) POSITION IN GENOME:
    (A) CHROMOSOME/SEGMENT:
    (B) MAP POSITION:
    (C) UNITS:

(i x) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(x i) SEQUENCE DESCRIPTION: SEQ ID NO:57:

```
CTAGAAGCAA AGCAGGGGAT AATTCTATTA ATCATGAAGA CCATCATTGC TTTGAGCTAC      60
ATTTTCTGTC TGGCTCTCGG CCAAGACCTT CCAGGAAATG ACAACAGCAC AGCAACGCTG     120
TGCCTGGGAC ATCATGCGGT GCCAAACGGA ACACTAGTGA AAACAATCAC AGATGATCAG     180
ATTGAAGTGA CTAATGCTAC TGAGCTAGTT CAGAGCTCCT CAACGGGGAA AATATGCAAC     240
AATATTGATA CCTGTATTTC TGAATGCATC ACTCCAAATG GAAGCATTCC CAATGACAAG     300
CCCTTTCAAA ACGTAAACAA GATCACATAT GGAGCATGCC CCAAGTATGT TAAGCAAAAC     360
ACCCTGAAGT TGGCAACAGG GATGCGGAAT GTACCAGAGA ACAAACTAG AGGCCTATTC      420
GGCGCAATAG CAGGTTTCAT AGAAAATGGT TGGGAGGGAA TGATAGACGG TTGGTACGGT     480
TTCAGGCATC AAAATTCTGA GGGCACAGGA CAAGCAGCAG ATCTTAAAAG CACTCAAGCA     540
GCCATCGACC AAATCAATGG GAAATTGAAC AGGGTAATCG AGAAGACGAA CGAGAAATTC     600
CATCAAATCG AAAAGGAATT CTCAGAAGTA GAAGGGAGAA TTCAGGACCT CGAGAAATAC     660
GTTGAAGACA CTAAAATAGA TCTCTGGTCT TACAATGCGG AGCTTCTTGT CGCTCTGGAG     720
AATCAACATA CAATTGACCT GACTGACTCG GAAATGAACA AGCTGTTTGA AAAACAAGG     780
AGGCAACTGA GGGAAAATGC TGAAGAGATG GGCAATGGTT GCTTCAAAAT ATACCACAAA     840
TGTGACAACG CTTGCATAGA GTCAATCAGA AATGGTACTT ATGACCATGA TGTATACAGA     900
GACGAAGCAT TAAACAACCG GTTTCAGATC AAAGGTGTTG AACTGAAGTC TGGATACAAA     960
GACTGGATCC TGTGGATTTC CTTTGCCATA TCATGCTTTT TGCTTTGTGT TGTTTTGCTG    1020
GGGTTCATCA TGTGGGCCTG CCAGAGAGGC AACATTAGGT GCAACATTTG CATTTGAGTG    1080
TATTAGTAAT TAAAAACACC CTTGTTTCTG                                    1110
```

( 2 ) INFORMATION FOR SEQ ID NO:58:

( i ) SEQUENCE CHARACTERISTICS:
        ( A ) LENGTH: 347 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:58:

```
Met  Lys  Thr  Ile  Ile  Ala  Leu  Ser  Tyr  Ile  Phe  Cys  Leu  Ala  Leu
     -15                 -10                           -5

Gly  Gln  Asp  Leu  Pro  Gly  Asn  Asp  Asn  Ser  Thr  Ala  Thr  Leu  Cys
      1                  5                       10

Leu  Gly  His  His  Ala  Val  Pro  Asn  Gly  Thr  Leu  Val  Lys  Thr  Ile
     15                 20                       25

Thr  Asp  Asp  Gln  Ile  Glu  Val  Thr  Asn  Ala  Thr  Glu  Leu  Val  Gln
     30                 35                       40

Ser  Ser  Ser  Thr  Gly  Lys  Ile  Cys  Asn  Asn  Ile  Asp  Thr  Cys  Ile
     45                 50                       55

Ser  Glu  Cys  Ile  Thr  Pro  Asn  Gly  Ser  Ile  Pro  Asn  Asp  Lys  Pro
     60                 65                       70

Phe  Gln  Asn  Val  Asn  Lys  Ile  Thr  Tyr  Gly  Ala  Cys  Pro  Lys  Tyr
     75                 80                       85

Val  Lys  Gln  Asn  Thr  Leu  Lys  Leu  Ala  Thr  Gly  Met  Arg  Asn  Val
```

-continued

```
              90                        95                         100

Pro   Glu   Lys   Gln   Thr   Arg   Gly   Leu   Phe   Gly   Ala   Ile   Ala   Gly   Phe
105                             110                         115

Ile   Glu   Asn   Gly   Trp   Glu   Gly   Met   Ile   Asp   Gly   Trp   Tyr   Gly   Phe
120                             125                         130

Arg   His   Gln   Asn   Ser   Glu   Gly   Thr   Gly   Gln   Ala   Ala   Asp   Leu   Lys
135                             140                         145

Ser   Thr   Gln   Ala   Ala   Ile   Asp   Gln   Ile   Asn   Gly   Lys   Leu   Asn   Arg
150                             155                         160

Val   Ile   Glu   Lys   Thr   Asn   Glu   Lys   Phe   His   Gln   Ile   Glu   Lys   Glu
165                             170                         175

Phe   Ser   Glu   Val   Glu   Gly   Arg   Ile   Gln   Asp   Leu   Glu   Lys   Tyr   Val
180                             185                         190

Glu   Asp   Thr   Lys   Ile   Asp   Leu   Trp   Ser   Tyr   Asn   Ala   Glu   Leu   Leu
195                             200                         205

Val   Ala   Leu   Glu   Asn   Gln   His   Thr   Ile   Asp   Leu   Thr   Asp   Ser   Glu
210                             215                         220

Met   Asn   Lys   Leu   Phe   Glu   Lys   Thr   Arg   Arg   Gln   Leu   Arg   Glu   Asn
225                             230                         235

Ala   Glu   Glu   Met   Gly   Asn   Gly   Cys   Phe   Lys   Ile   Tyr   His   Lys   Cys
240                             245                         250

Asp   Asn   Ala   Cys   Ile   Glu   Ser   Ile   Arg   Asn   Gly   Thr   Tyr   Asp   His
255                             260                         265

Asp   Val   Tyr   Arg   Asp   Glu   Ala   Leu   Asn   Asn   Arg   Phe   Gln   Ile   Lys
270                             275                         280

Gly   Val   Glu   Leu   Lys   Ser   Gly   Tyr   Lys   Asp   Trp   Ile   Leu   Trp   Ile
285                             290                         295

Ser   Phe   Ala   Ile   Ser   Cys   Phe   Leu   Leu   Cys   Val   Val   Leu   Leu   Gly
300                             305                         310

Phe   Ile   Met   Trp   Ala   Cys   Gln   Arg   Gly   Asn   Ile   Arg   Cys   Asn   Ile
315                             320                         325

Cys   Ile
330
```